US012673923B2

(12) United States Patent
Park et al.

(10) Patent No.: US 12,673,923 B2
(45) Date of Patent: Jul. 7, 2026

(54) ORGANIC COMPOUND AND AN ORGANIC ELECTROLUMINESCENT DEVICE USING THE SAME

(71) Applicant: SOLUS ADVANCED MATERIALS CO., LTD., Iksan-si (KR)

(72) Inventors: Woojae Park, Yongin-si (KR); Minsik Eum, Yongin-si (KR); Jaeyi Sim, Yongin-si (KR); Jeongkeun Park, Yongin-si (KR); Hyosuk Son, Yongin-si (KR); Yonghwan Lee, Yongin-si (KR); Songie Han, Yongin-si (KR)

(73) Assignee: SOLUS ADVANCED MATERIALS CO., LTD., Iksan-si (KR)

( * ) Notice: Subject to any disclaimer, the term of this patent is extended or adjusted under 35 U.S.C. 154(b) by 1043 days.

(21) Appl. No.: 17/778,565

(22) PCT Filed: Nov. 19, 2020

(86) PCT No.: PCT/KR2020/016316
§ 371 (c)(1),
(2) Date: May 20, 2022

(87) PCT Pub. No.: WO2021/101255
PCT Pub. Date: May 27, 2021

(65) Prior Publication Data

US 2023/0045312 A1 Feb. 9, 2023

(30) Foreign Application Priority Data

Nov. 21, 2019 (KR) ........................ 10-2019-0150373

(51) Int. Cl.
*C07D 239/26* (2006.01)
*H10K 50/16* (2023.01)
*H10K 85/60* (2023.01)

(52) U.S. Cl.
CPC ........... *C07D 239/26* (2013.01); *H10K 50/16* (2023.02); *H10K 85/654* (2023.02)

(58) Field of Classification Search
CPC ..... C07D 239/26; H10K 50/16; H10K 85/654
See application file for complete search history.

(56) References Cited

U.S. PATENT DOCUMENTS

2017/0373255 A1 12/2017 Lee et al.
2020/0168805 A1* 5/2020 Park ..................... C07D 403/10

FOREIGN PATENT DOCUMENTS

CN 107108504 A 8/2017
CN 112236879 A 1/2021
(Continued)

OTHER PUBLICATIONS

Machine-generated English-language translation of WO-2016105141-A2.*
(Continued)

*Primary Examiner* — Vu A Nguyen
(74) *Attorney, Agent, or Firm* — Sughrue Mion, PLLC

(57) ABSTRACT

The present invention relates to a novel organic compound and an organic electroluminescent device using the same and, more specifically, to: an organic compound having excellent heat resistance, carrier transport capability, luminescence capability, electron injection/transport capability, electrochemical stability, and the like; and an organic electroluminescent device which, by including the compound in one or more organic layers, has improved characteristics such as improved luminous efficiency, driving voltage, and lifespan.

11 Claims, 2 Drawing Sheets

(56) References Cited

FOREIGN PATENT DOCUMENTS

| | | | | |
|---|---|---|---|---|
| JP | 2018-507174 A | | 3/2018 | |
| JP | 2019-513133 A | | 5/2019 | |
| KR | 10-1537500 B1 | | 7/2015 | |
| KR | 10-2016-0078237 A | | 7/2016 | |
| KR | 10-2016-0078251 A | | 7/2016 | |
| KR | 10-2017-0086211 A | | 7/2017 | |
| KR | 10-2018-0000621 A | | 1/2018 | |
| KR | 10-2019-0009994 A | | 1/2019 | |
| KR | 10-2020-0026754 A | | 3/2020 | |
| WO | WO-2016105141 A2 | * | 6/2016 | ........... H10K 85/631 |
| WO | WO-2019017616 A1 | * | 1/2019 | ........... C07D 403/10 |

OTHER PUBLICATIONS

International Search Report for PCT/KR2020/016316 dated, Mar. 8, 2021 (PCT/ISA/210).

Partial Supplementary European Search Report dated Aug. 22, 2023 in European Application No. 20890077.9.

* cited by examiner

ORGANIC COMPOUND AND AN ORGANIC ELECTROLUMINESCENT DEVICE USING THE SAME

CROSS REFERENCE TO RELATED APPLICATIONS

This application is a National Stage of International Application No. PCT/KR2020/016316 filed Nov. 19, 2020, claiming priority based on Korean Patent Application No. 10-2019-0150373 filed Nov. 21, 2019.

TECHNICAL FIELD

The present invention relates to a novel organic compound and an organic electroluminescent device using the same, and more particularly, to an organic compound having excellent heat resistance, carrier transport capability, luminescence capability, electron injection/transport capability, electrochemical stability, and the like; and an organic electroluminescent device which, by including the organic compound in one or more organic layers, has improved characteristics such as improved luminous efficiency, driving voltage, and lifespan.

BACKGROUND ART

In organic electroluminescent devices (hereinafter, "organic EL devices"), upon application of voltage between two electrodes, holes are injected from an anode (e.g., positive electrode) to an organic layer and electrons are injected from a cathode (e.g., negative electrode) to the organic layer. Injected holes and electrons meet each other to form excitons, and light emission occurs when the excitons fall to a ground state. In such a case, materials used for the organic layer may be classified into, for example, light-emitting materials, hole injection materials, hole transport materials, electron transport materials and electron injection materials according to their function.

Light-emitting materials may be classified into blue, green and red light-emitting materials according to their emission colors, and further into yellow and orange light-emitting materials for realizing better natural colors. In addition, a host/dopant system may be employed in the light-emitting material to increase color purity and luminous efficiency through energy transition.

Dopant materials may be classified into fluorescent dopants using organic materials and phosphorescent dopants using metal complex compounds which include heavy atoms such as Ir and Pt. In such a case, the developed phosphorescent materials may improve the luminous efficiency theoretically up to four times as compared to fluorescent materials, so studies are being conducted on phosphorescent dopants as well as phosphorescent host materials.

To date, NPB, BCP and $Alq_3$, for example, are widely known as materials used in the hole injection layer, the hole transport layer, the hole blocking layer and the electron transport layer, and anthracene derivatives have been reported as light-emitting materials. Particularly, metal complex compounds including Ir, such as Firpic, $Ir(ppy)_3$, (acac)$Ir(btp)_2$, which are known to have advantages in terms of efficiency improvement among light-emitting materials, are used as blue, green and red phosphorescent dopant materials, and 4,4-dicarbazolylbiphenyl (CBP) is used as a phosphorescent host material.

However, although conventional organic layer materials are advantageous in terms of luminescence properties, they have low glass transition temperatures, thus having poor thermal stability, and thus they do not exhibit satisfactory lifespan characteristics for organic EL devices. Accordingly, there is a demand for organic layer materials that are excellent in performance.

DETAILED DESCRIPTION OF THE INVENTION

Technical Objectives

The present invention is directed to an organic layer material of an organic electroluminescent device that is excellent in heat resistance, carrier transport ability, light-emitting ability, electrochemical stability, and the like, and specifically, to a novel organic compound applicable as an electron transport layer material.

In addition, the present invention is also directed to an organic electroluminescent device including the aforementioned novel organic compound, thereby having low driving voltage, high luminous efficiency, and improved lifespan.

Technical Solution to the Problem

In order to achieve the above objectiveness, the present invention provides an organic compound represented by the following Chemical Formula 1 or 2:

[Chemical Formula 1]

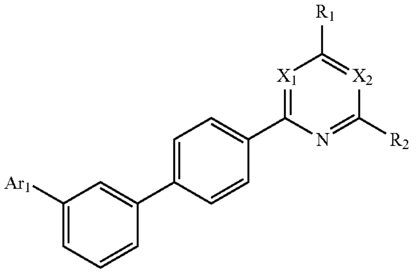

[Chemical Formula 2]

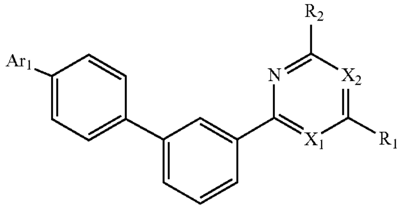

(in Chemical Formulas 1 and 2, $X_1$ and $X_2$ are different from each other and are $CR_3$ or N, wherein one of $X_1$ and $X_2$ is N and the other is $CR_3$, $R_1$ and $R_2$ are the same as or different from each other, each independently being selected from: a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphin oxide group, and a $C_6$ to $C_{60}$ arylamine group, $Ar_1$ is a substituent represented by any one of the following Chemical Formulas F1 to F6:

F1

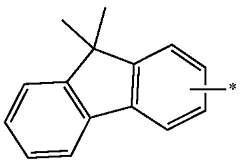

F2

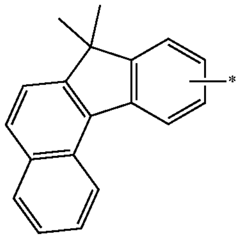

F3

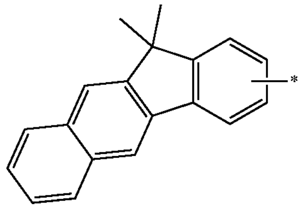

F4

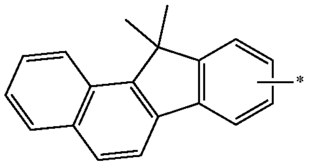

F5

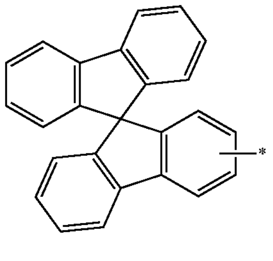

F6

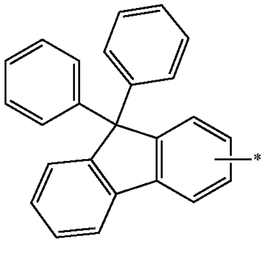

$R_3$ is selected from: hydrogen, deuterium, halogen, a cyano group, a $C_1$ to $C_{40}$ alkyl group, a $C_6$ to $C_{60}$ aryl group, a heteroaryl group having 5 to 60 nuclear atoms, the alkenyl group, the alkynyl group, the cycloalkyl group, the heterocycloalkyl group, the alkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ and $R_2$, and the alkyl group, the aryl group, and the heteroaryl group of $R_3$ are each independently substituted or unsubstituted with one or more substituents of: deuterium, halogen, a cyano group, a nitro group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and when the substituents are plural in number, the substituents are the same as or different from each other).

In addition, the present invention provides an electroluminescent device comprising: an anode, a cathode, and one or more organic layer disposed between the anode and the cathode, wherein at least one of the one or more organic layer comprises the compound.

Effects of the Invention

The compound of the present invention is excellent in terms of heat resistance, carrier transport capability, luminescence capability, electrochemical stability, and the like, and thus may be applicable as an organic layer material of an organic electroluminescent device. In particular, when the compound of the present invention is used as at least one of an electron transport layer material or an electron transport auxiliary layer material, an organic electroluminescent device having excellent light-emitting performance, low driving voltage, high efficiency and long lifespan characteristics as compared to conventional materials may be manufactured, and it is possible to manufacture a full color display panel with improved performance and lifespan.

REFERENCE NUMERAL

Figure 1:
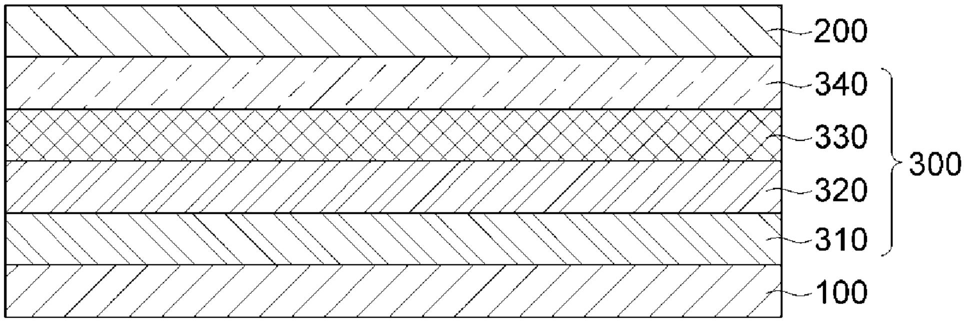
FIG. 1 is a cross-sectional view schematically illustrating an organic electroluminescent ("EL") device according to a first embodiment of the present invention.

100: Anode, 200: Cathode,
300: Organic layer, 310: Hole injection layer,
320: Hole transport layer, 330: Light-emitting layer,
340: Electron transport layer, 350: Electron injection layer,
360: Electron transport auxiliary layer

DETAILED DESCRIPTION OF THE INVENTION

Hereinafter, the present invention will be described in detail.

<Organic Compound>

The present invention provides a compound that may be used as a high-efficiency electron transport layer material having excellent heat resistance, carrier transport ability, light-emitting ability, electrochemical stability, and the like.

Specifically, in the compound according to the present invention, a pyrimidine moiety and a fluorene moiety or a benzofluorene moiety are bonded through a biphenylene group which is a linker to form a basic skeleton, and these are bonded to a meta-para position or a para-meta position and represented by Chemical Formula 1 or 2. Accordingly, the compound of the present invention has a plate-like structure, while having asymmetry with respect to a major axis (e.g., long axis) of the molecule, and thus it is excellent in terms of heat resistance, carrier transport ability, light-emitting ability, electrochemical stability, and the like. When the compound of Chemical Formula 1 or 2 is applied to an organic electroluminescent ("EL") device, the organic EL device may have a low driving voltage, high luminous efficiency and current efficiency, and a long lifespan.

In the above Chemical Formula 1 or 2, $X_1$ and $X_2$ are different from each other and are $CR_3$ or N, where one of $X_1$ and $X_2$ is N and the other is $CR_3$. Accordingly, the compound of the present invention contains a pyrimidine moiety which is an electron withdrawing group (EWG) having high electron absorptivity.

$R_3$ is selected from: hydrogen, deuterium, halogen, a cyano group, a $C_1$ to $C_{40}$ alkyl group, a $C_6$ to $C_{60}$ aryl group, and a heteroaryl group having 5 to 60 nuclear atoms.

According to an embodiment, $X_1$ may be $CR_3$, and $X_2$ may be N. In such a case, $R_3$ may be selected from: hydrogen, deuterium, halogen, a cyano group and a $C_1$ to $C_{40}$ alkyl group and may specifically be hydrogen or deuterium.

In the above Chemical Formula 1 or 2, $R_1$ and $R_2$ may be the same as or different from each other, each independently being selected from: a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphin oxide group, and a $C_6$ to $C_{60}$ arylamine group, and specifically selected from: a $C_1$ to $C_{40}$ alkyl group, a $C_6$ to $C_{60}$ aryl group, and a heteroaryl group having 5 to 60 nuclear atoms.

According to an embodiment, $R_1$ and $R_2$ may be different from each other and may each independently be selected from: a $C_1$ to $C_{40}$ alkyl group, a $C_6$ to $C_{60}$ aryl group, and a heteroaryl group having 5 to 60 nuclear atoms. Specifically, $R_1$ and $R_2$ may be different from each other and may be a $C_6$ to $C_{60}$ aryl group.

According to another embodiment, $R_1$ and $R_2$ may be different from each other, and any one of $R_1$ and $R_2$ may be a biphenyl group or a terphenyl group, and the other may be a phenyl group.

In the above Chemical Formula 1 or 2, $Ar_1$ is a substituent represented by any one of the following Chemical Formulas F1 to F6.

F1

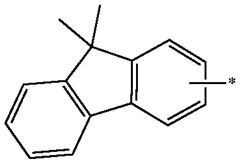

F2

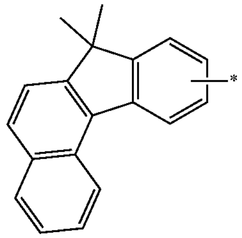

F3

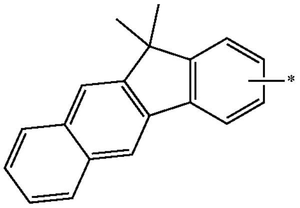

F4

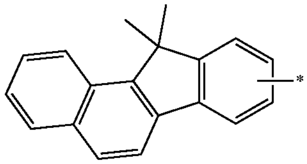

F5

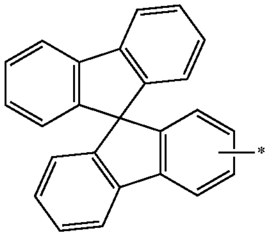

F6

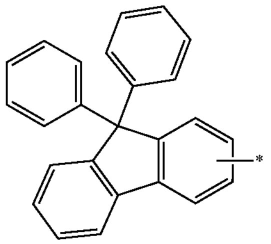

The substituents of the Chemical Formulas F1 to F6 are substituents which have electron donor group (EDG) characteristics with large electron donating properties, and by bonding with a pyrimidine moiety, which is an electron withdrawing group (EWG) having high electron absorptivity, through a biphenylene group which is a linker group, the entire molecule has a bipolar characteristic, and thus a bonding force between holes and electrons is high.

In an embodiment, $Ar_1$ may be a substituent represented by Chemical Formula F1.

In the above Chemical Formula 1 or 2, the alkenyl group, the alkynyl group, the cycloalkyl group, the heterocycloalkyl group, the alkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ and $R_2$, and the alkyl group, the aryl group, and the heteroaryl group of $R_3$ may each independently be substituted or unsubstituted with one or more substituents selected from: deuterium, halogen, a cyano group, a nitro group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, a $C_6$ to $C_{60}$ arylamine group, and specifically selected from: deuterium, halogen, a cyano group, a nitro group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, and a heteroaryl group having 5 to 60 nuclear atoms. In such a case, when the substituents are plural in number, the substituents may the same as or different from each other.

The compound represented by Chemical Formula 1 or 2 according to the present invention may be embodied as a compound represented by Chemical Formula 3 or 4 below, but embodiments are not limited thereto.

[Chemical Formula 3]

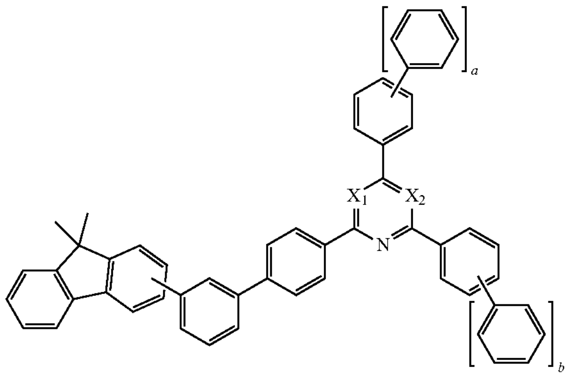

[Chemical Formula 4]

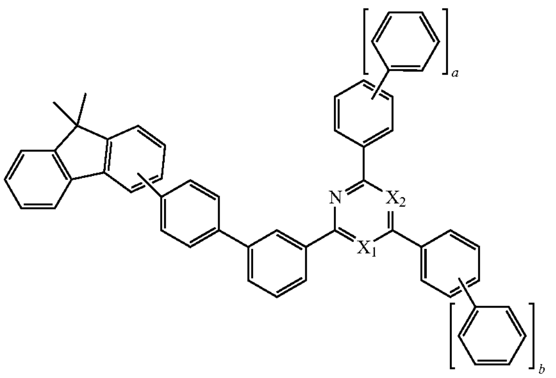

(In Chemical Formulas 3 and 4, $X_1$ and $X_2$ are as defined in Chemical Formulas 1 and 2, respectively, and a and b are each 0 or 1, provided that a+b=1).

The compound represented by Chemical Formula 1 or 2 according to the present invention described above may be embodied as the following Compounds 1 to 250. However, the compound represented by Chemical Formula 1 or 2 according to the present invention is not limited by those exemplified below.

1

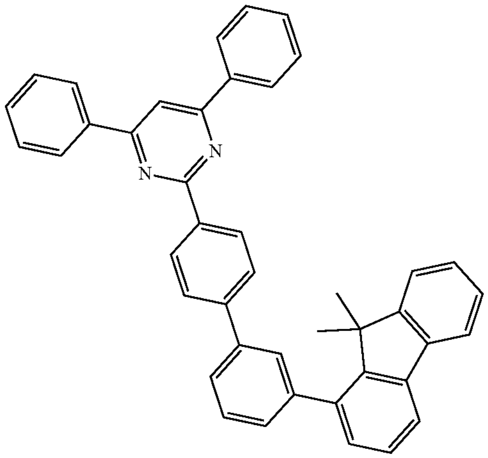

2

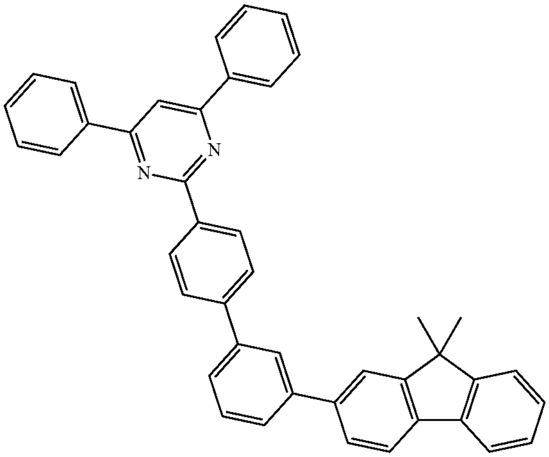

-continued
3
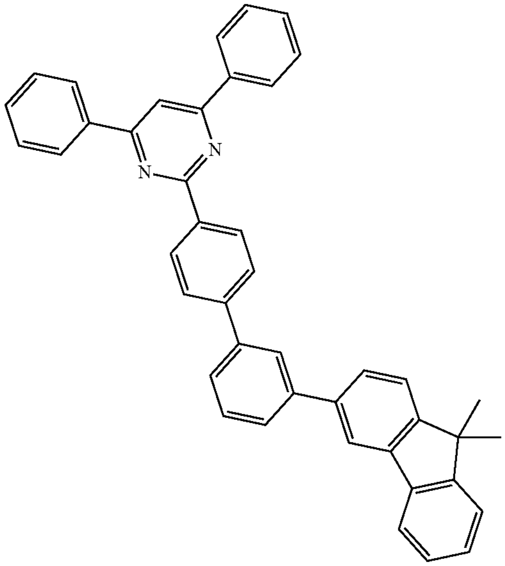
4
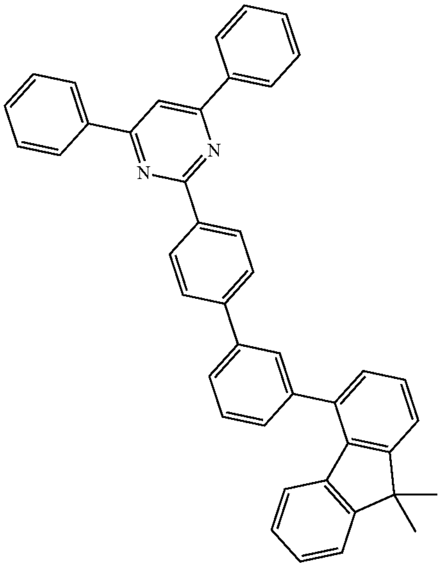
5
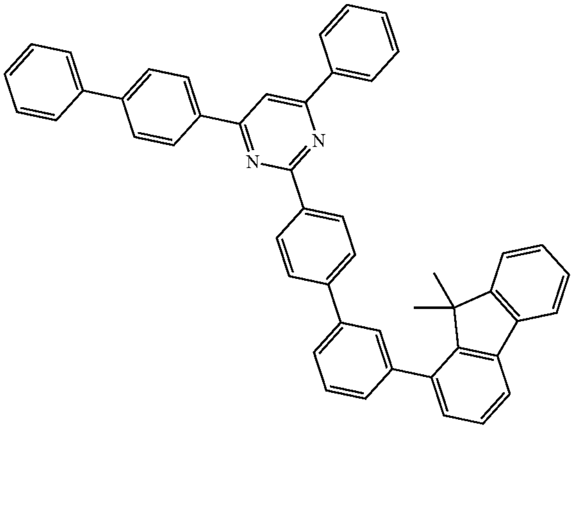
-continued
6
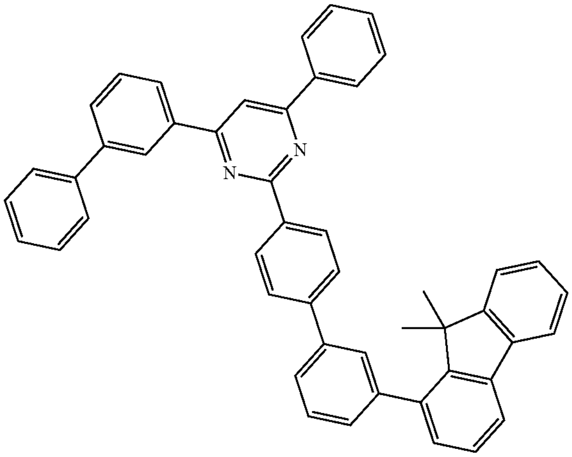
7
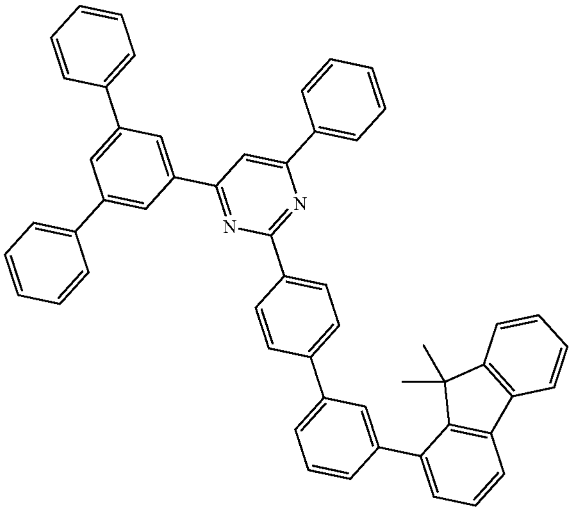
8
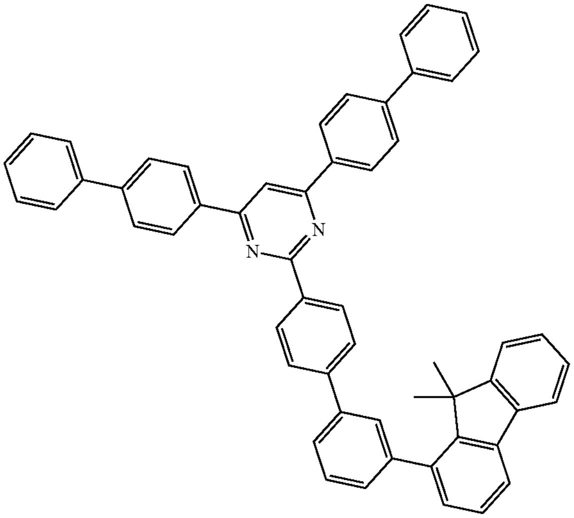

-continued
9
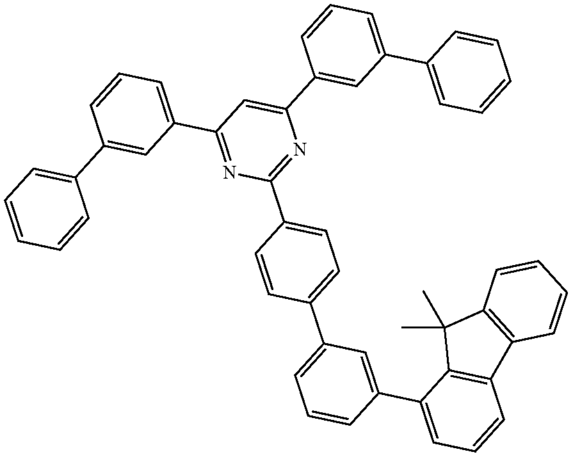
10
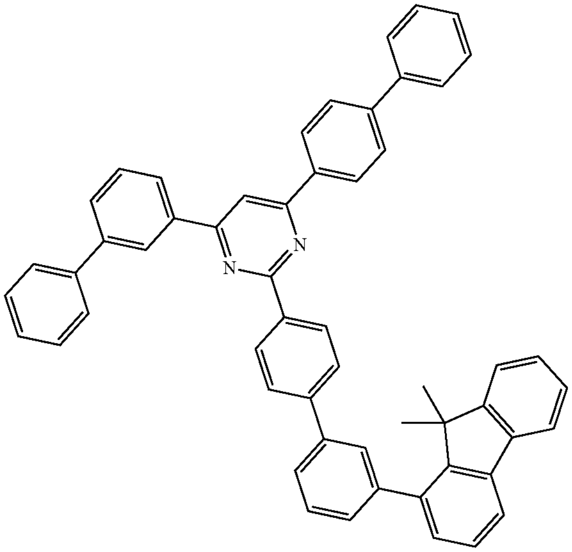
11
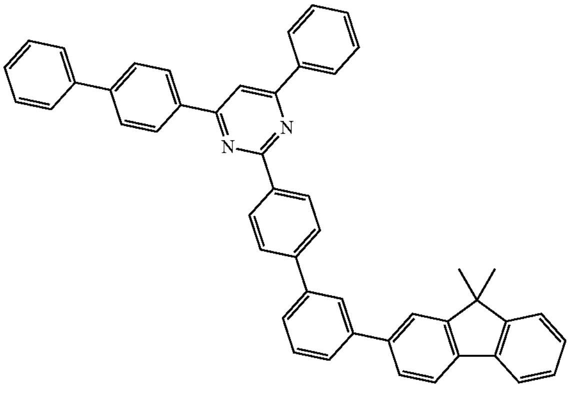
-continued
12
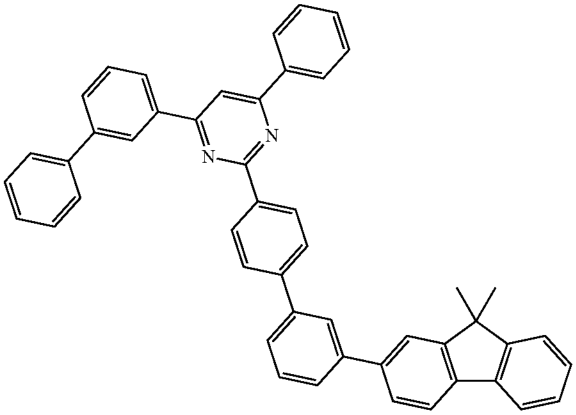
13
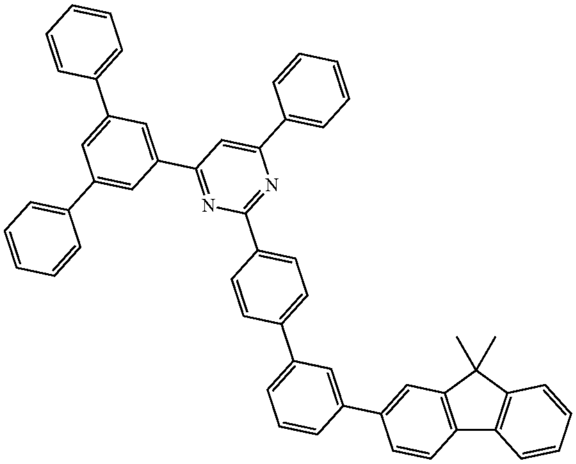
14
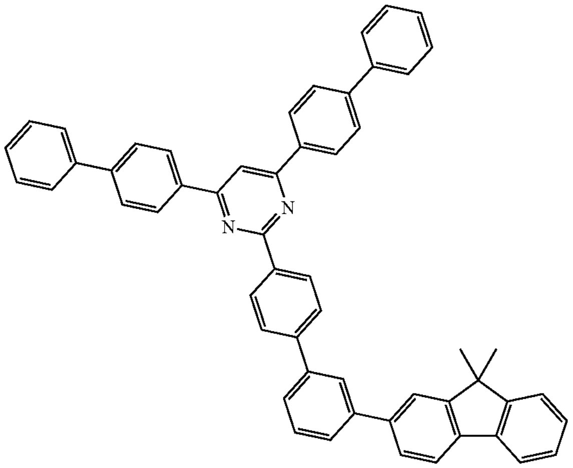

-continued
15
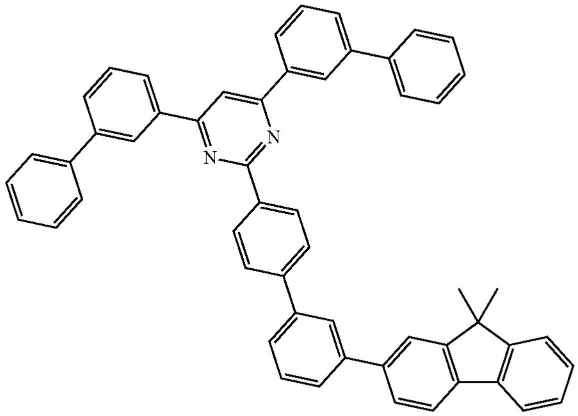
16
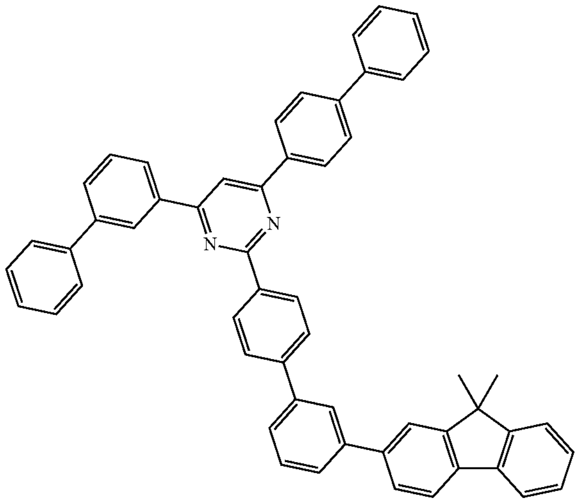
17
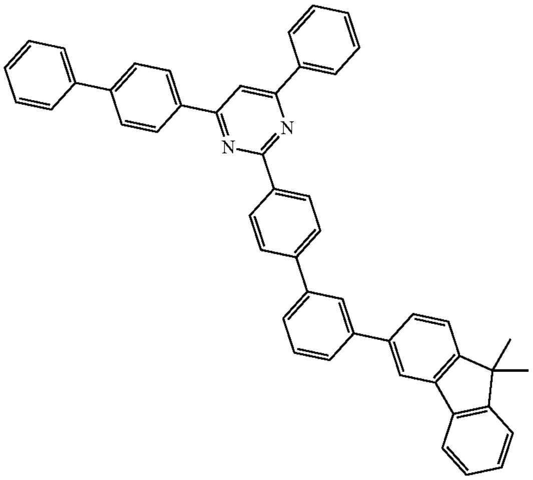
-continued
18
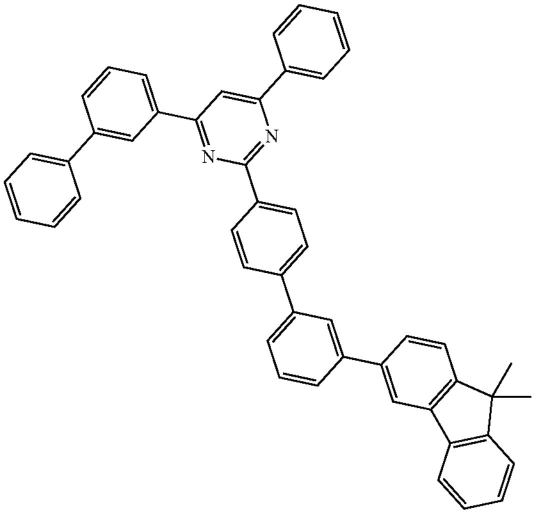
19
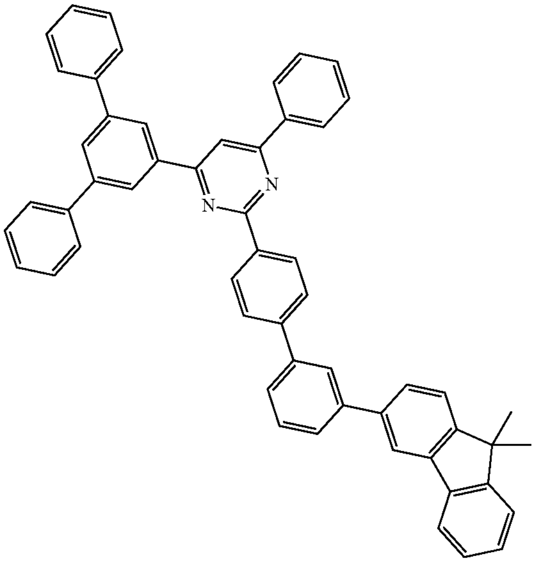

-continued
20
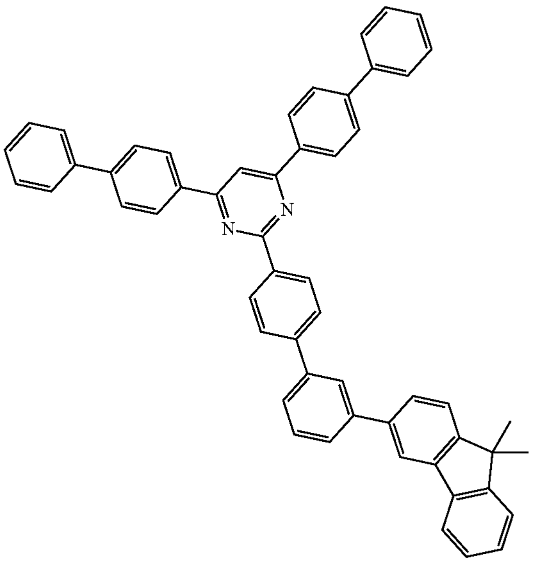
21
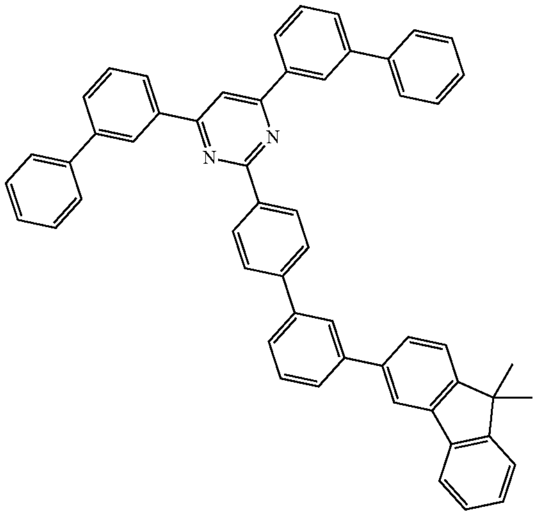
-continued
22
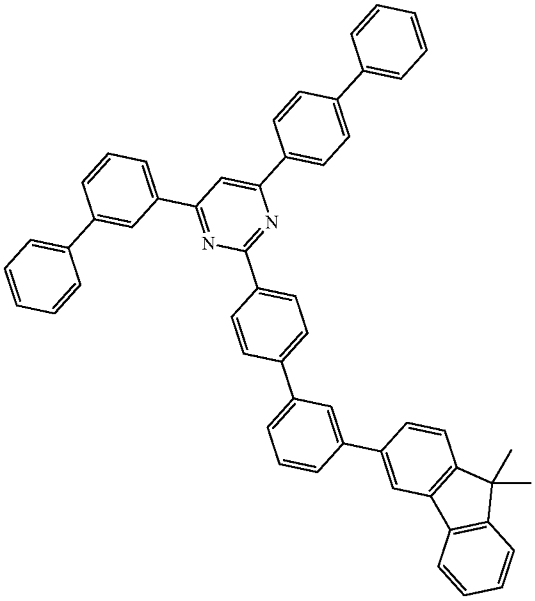
23
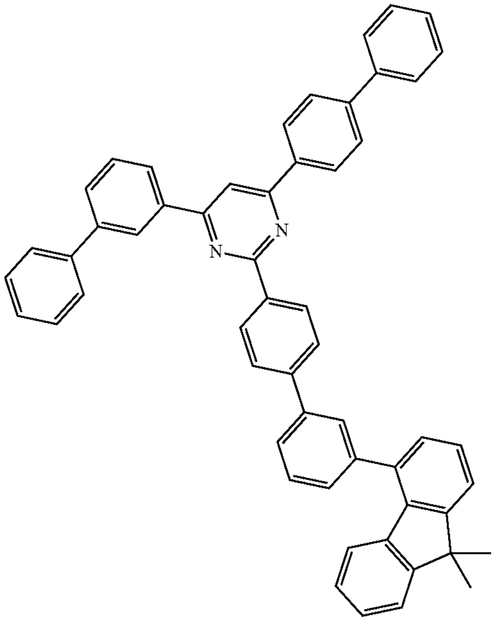

-continued
24
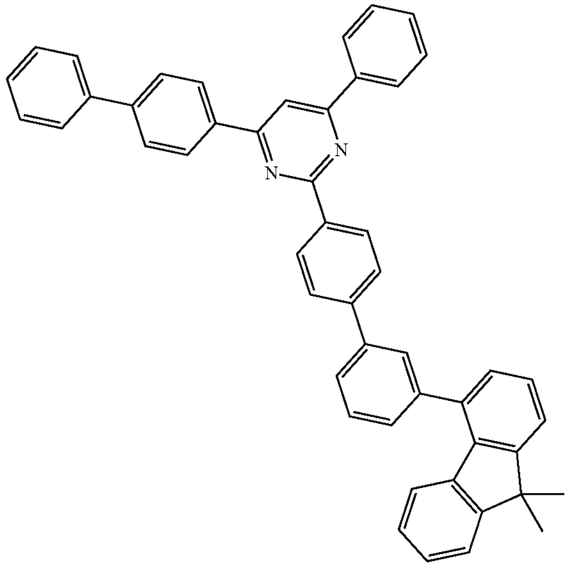
25
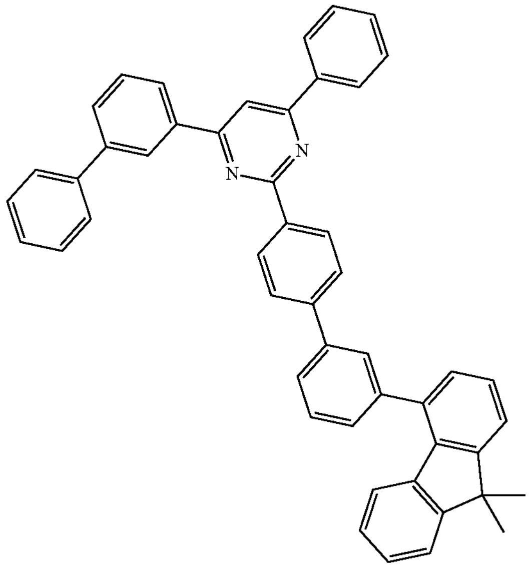
26
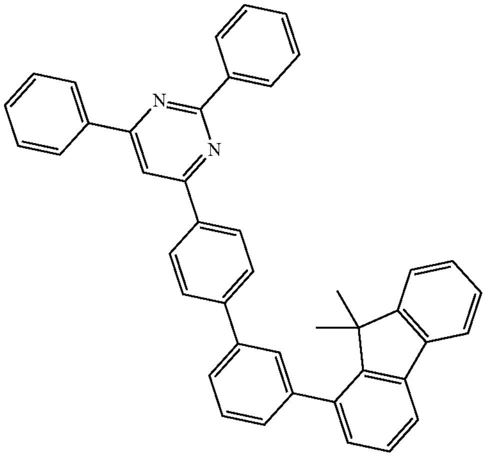
-continued
27
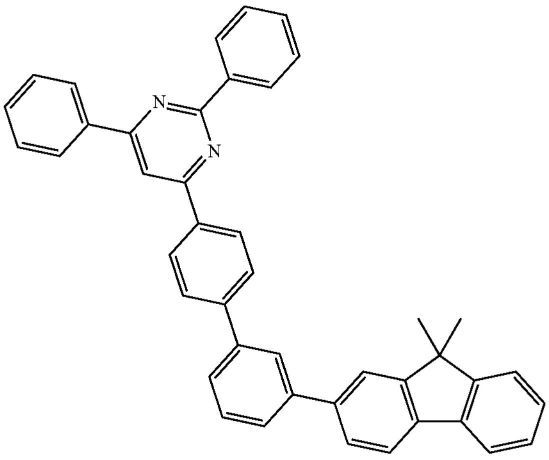
28
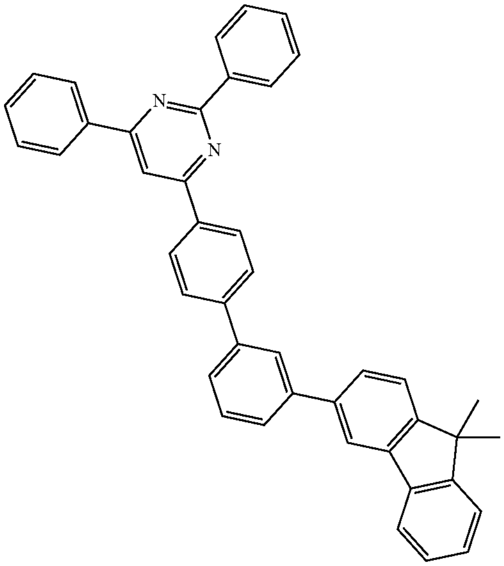
29
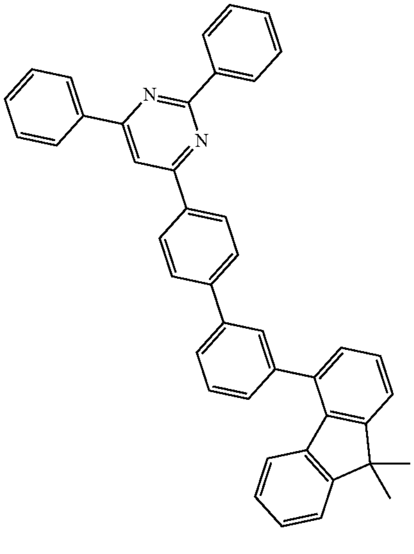

-continued
30
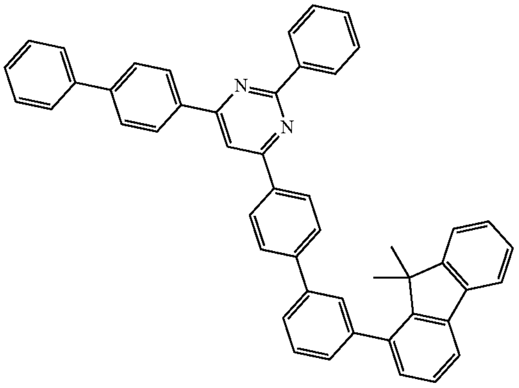
31
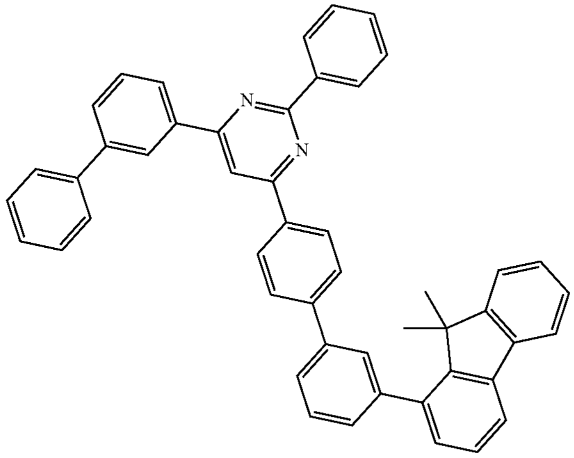
32
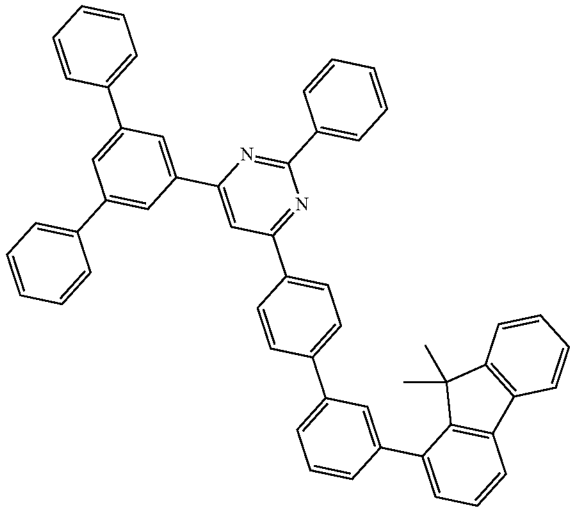
-continued
33
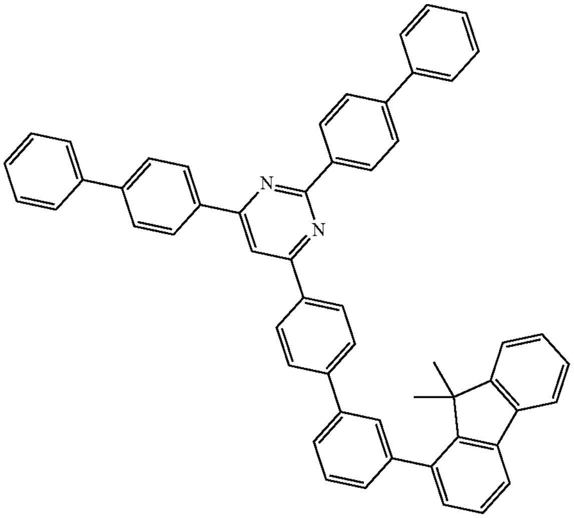
34
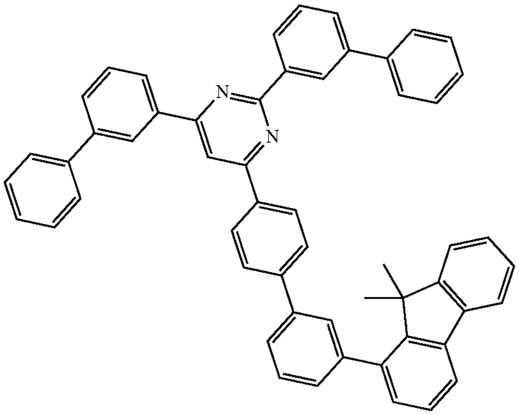
35
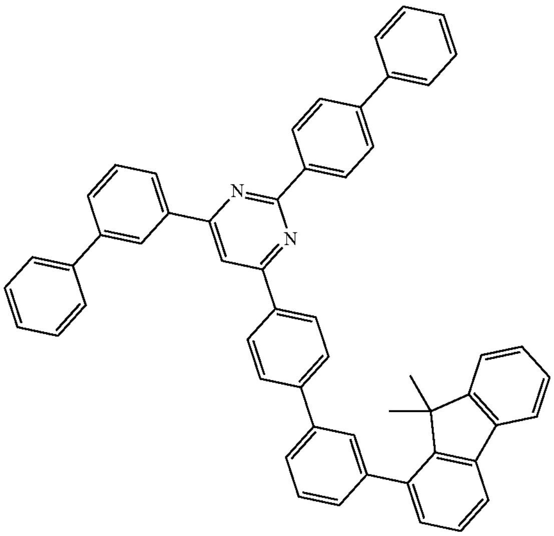

-continued
36
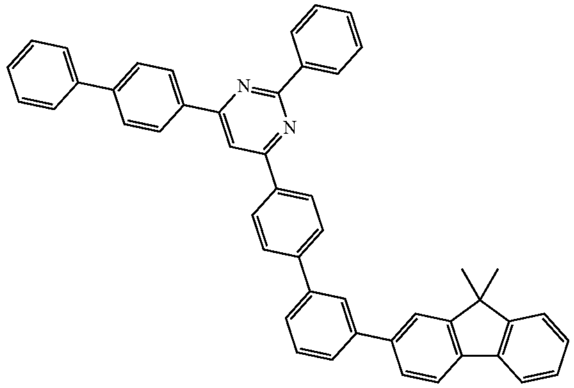
37
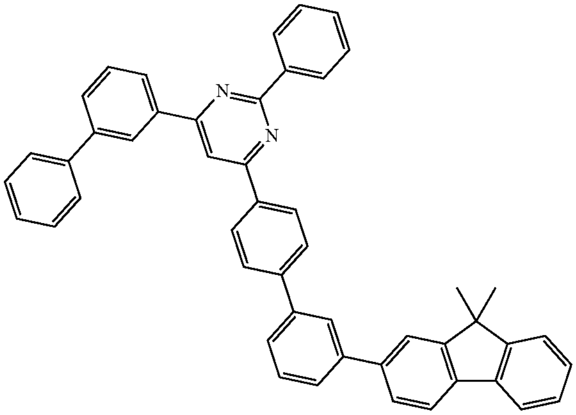
38
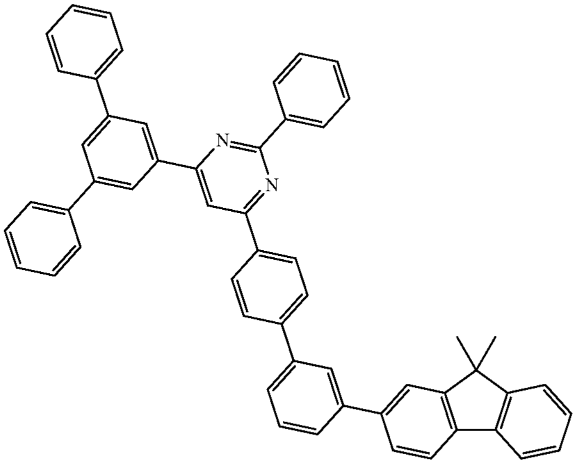
-continued
39
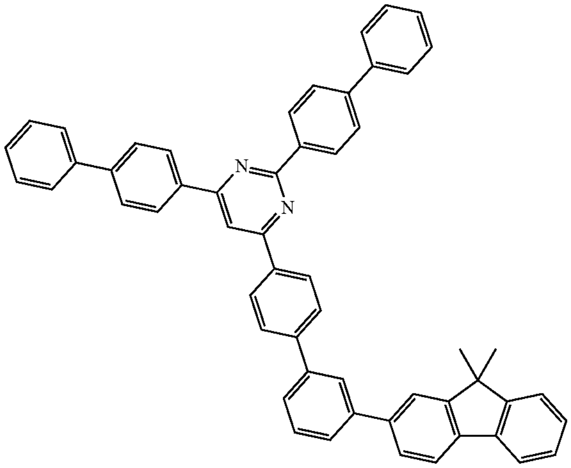
40
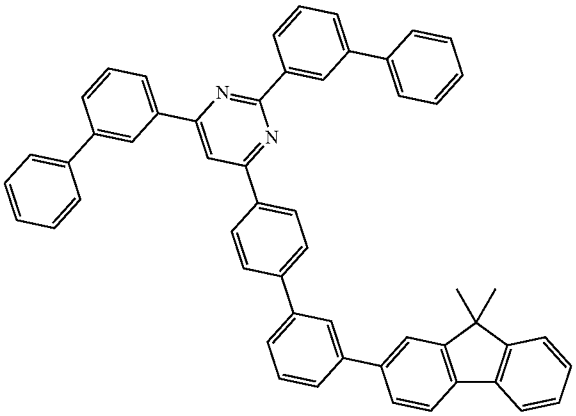
41
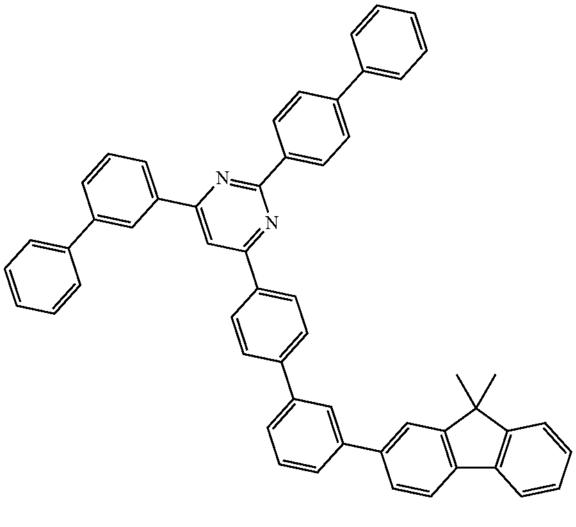

-continued
42
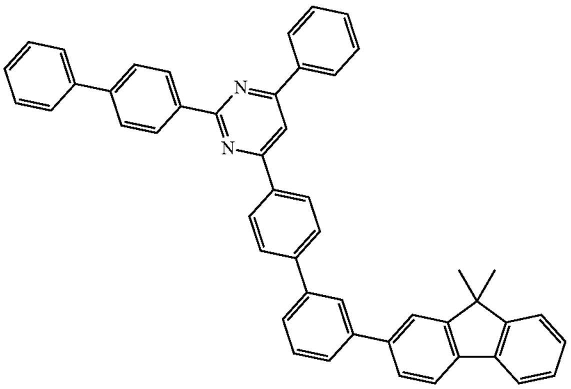
43
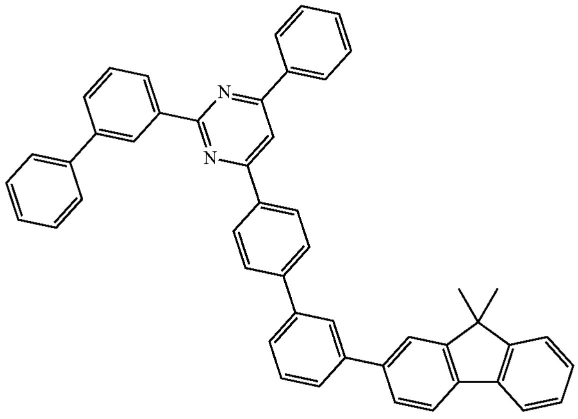
44
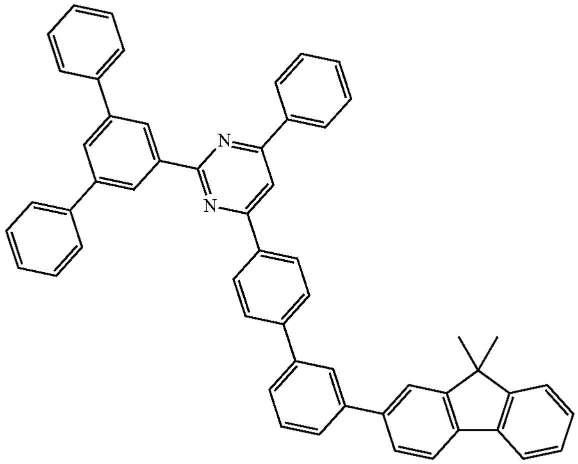
-continued
45
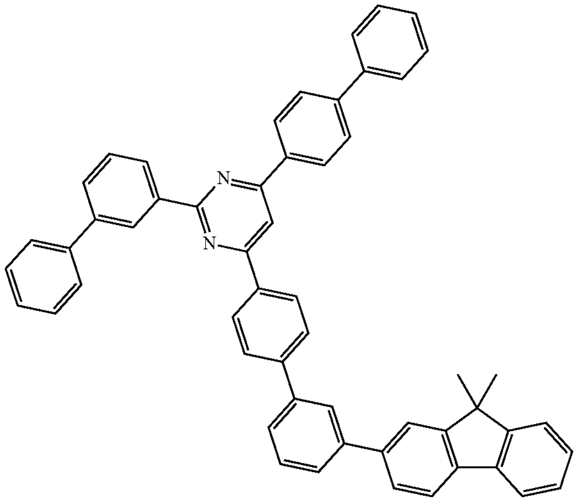
46
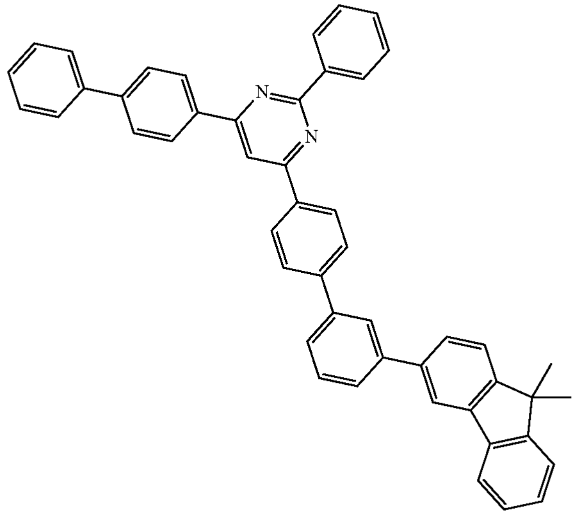
47
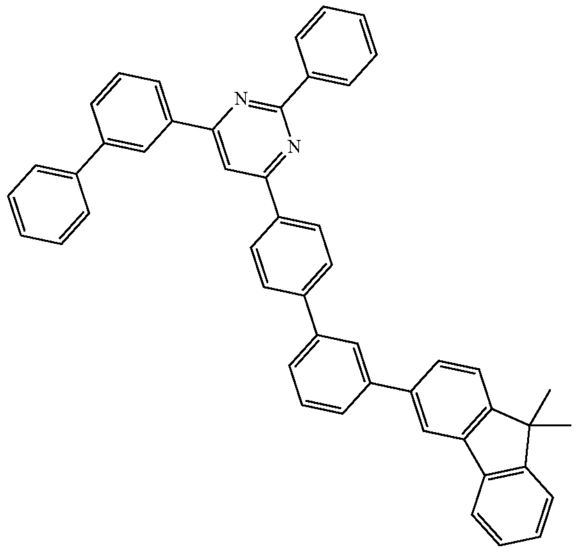

-continued
48
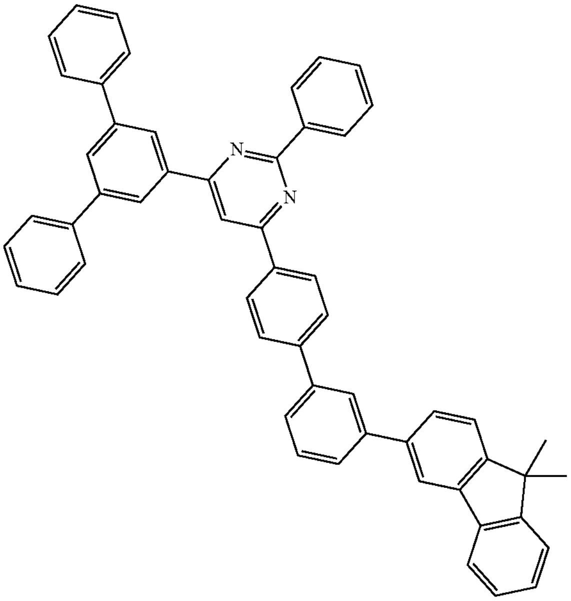
49
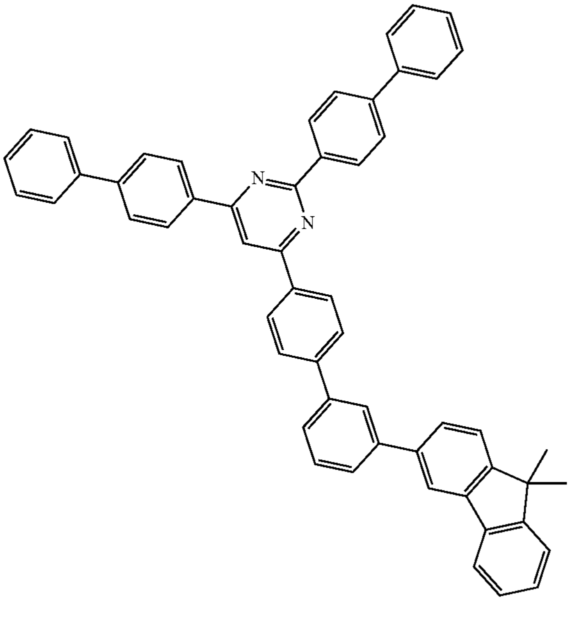
-continued
50
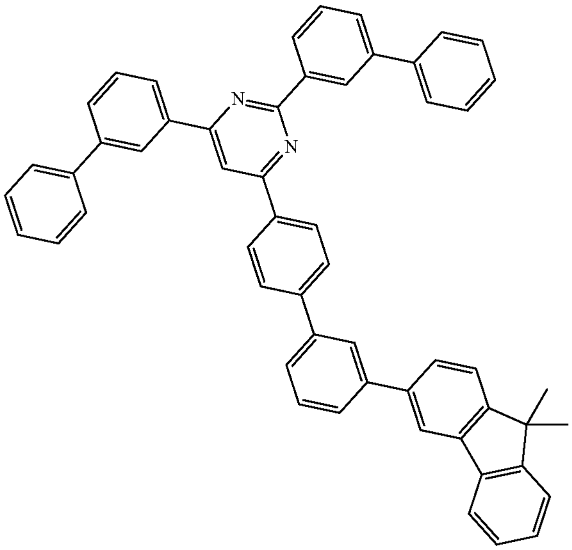
51
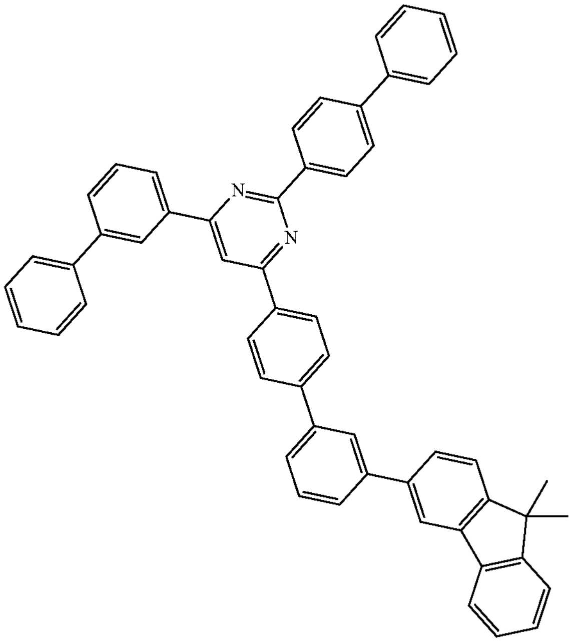

-continued
52
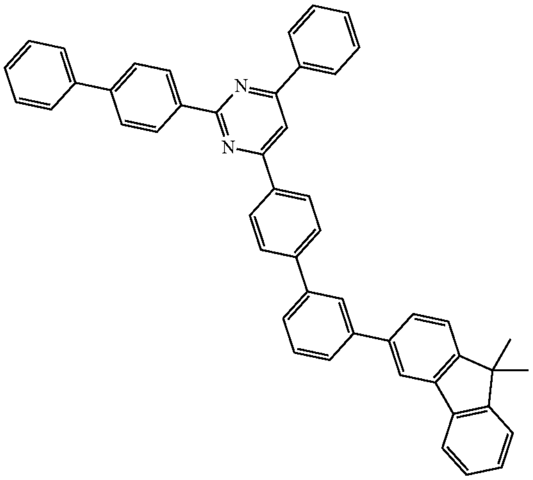
53
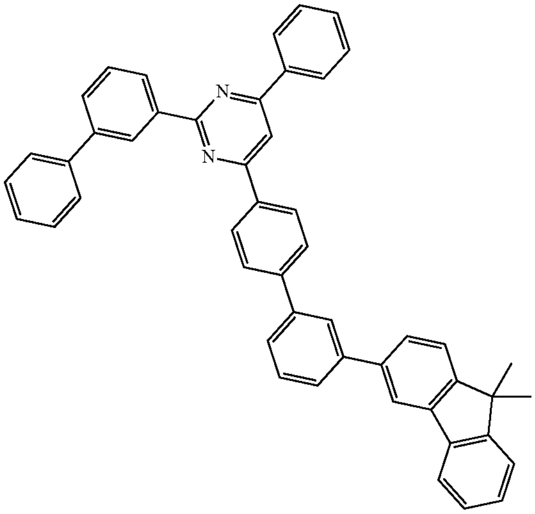
54
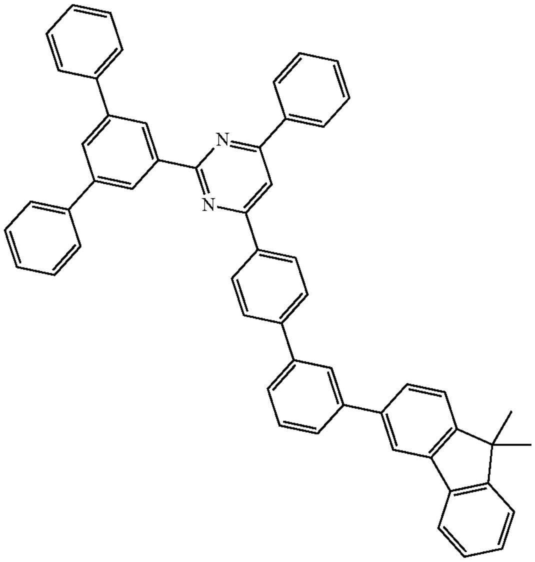
-continued
55
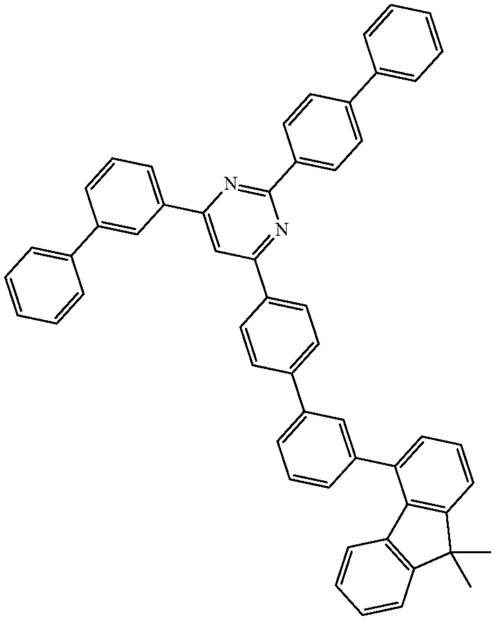
56
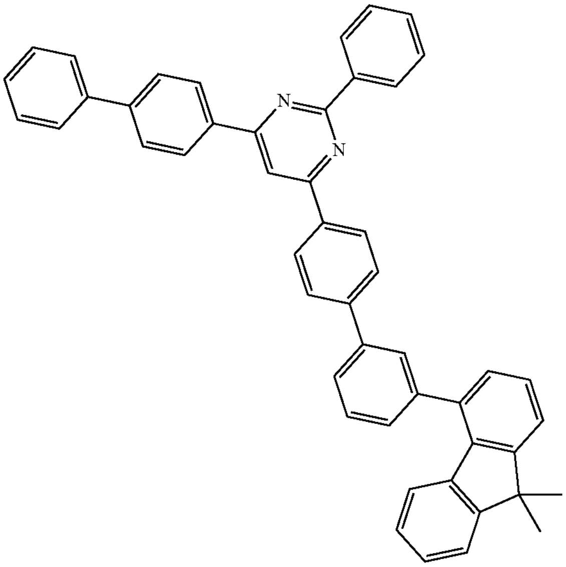

-continued
57
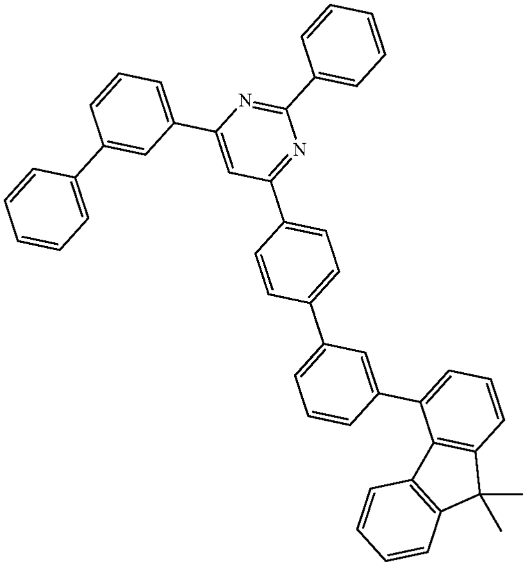
58
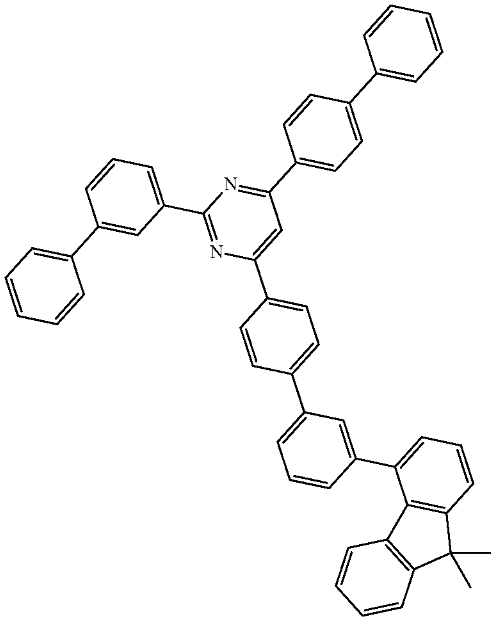
-continued
59
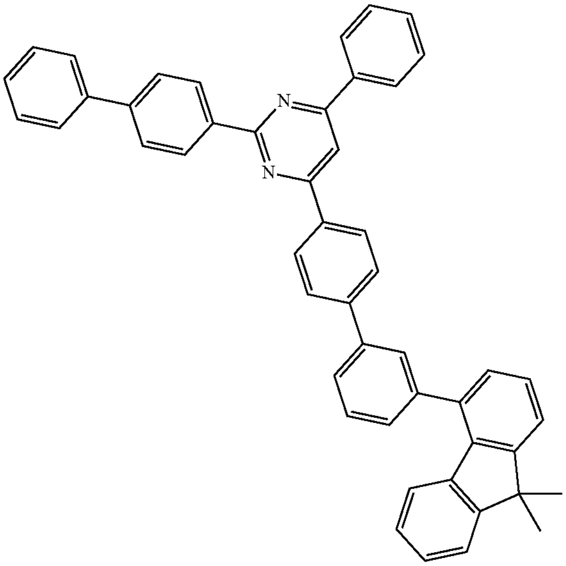
60
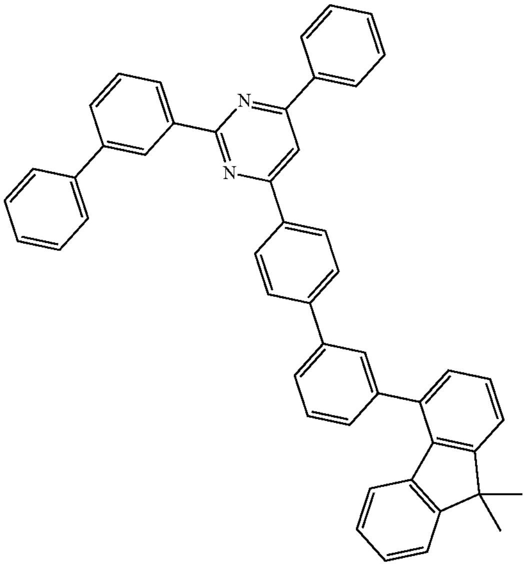
61
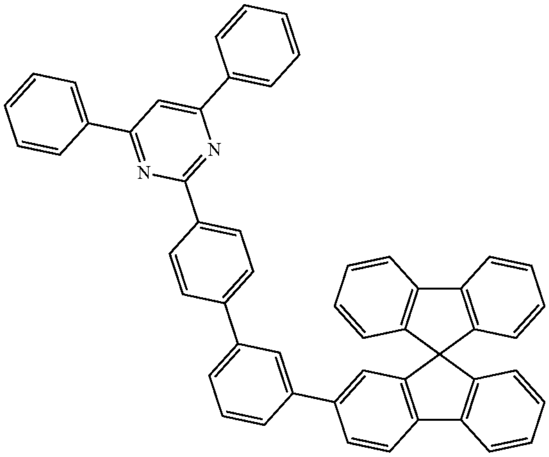

-continued
62
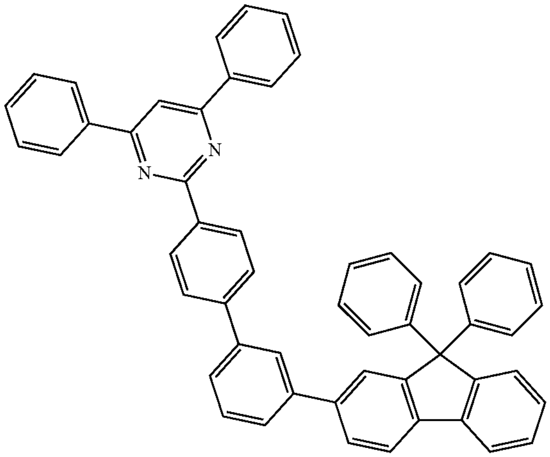
63
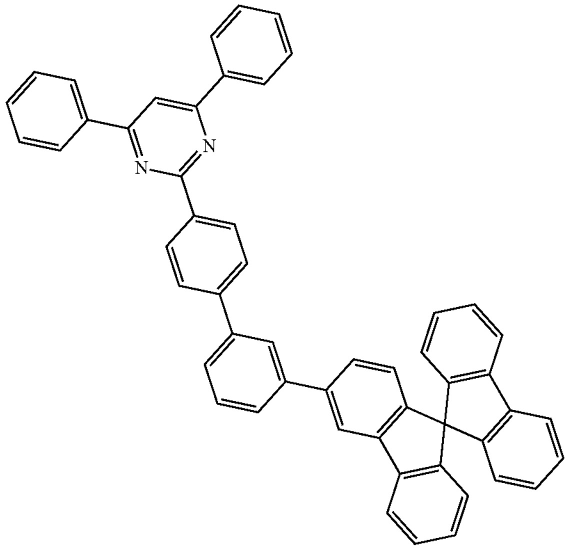
64
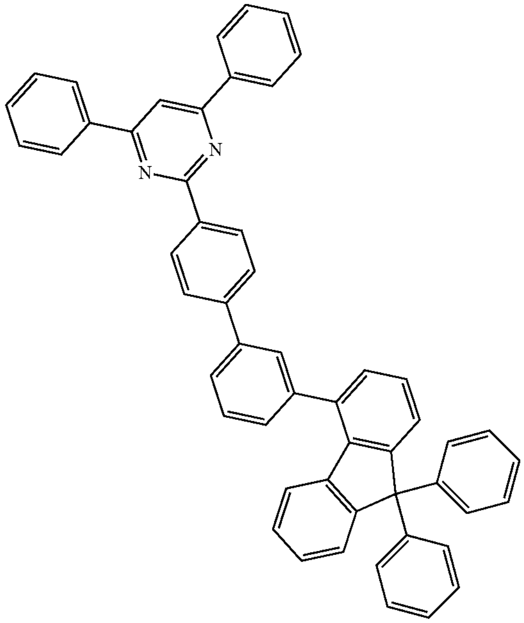
-continued
65
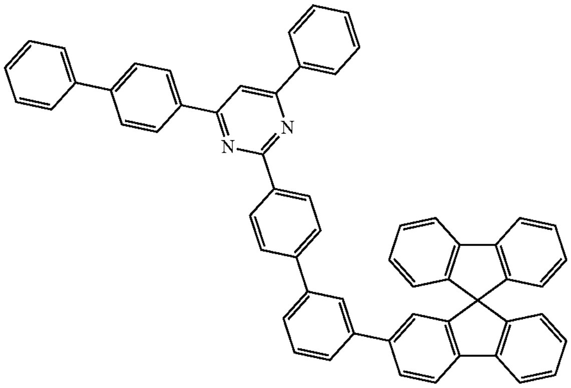
66
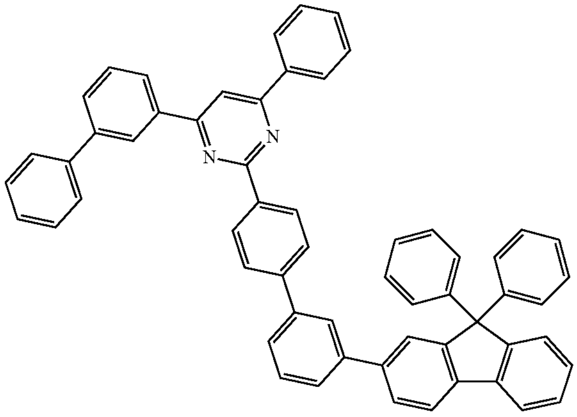
67
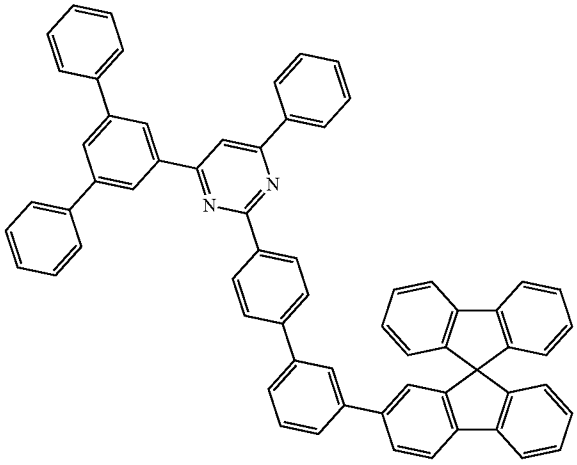

-continued
68
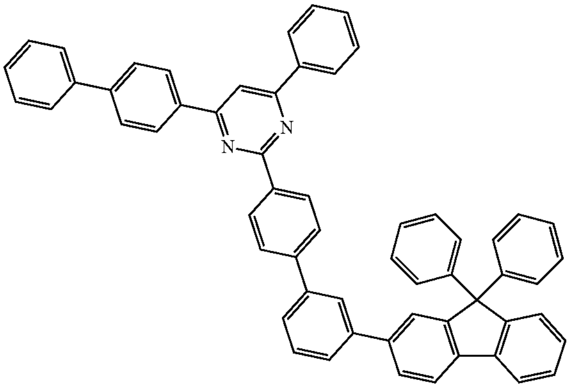
69
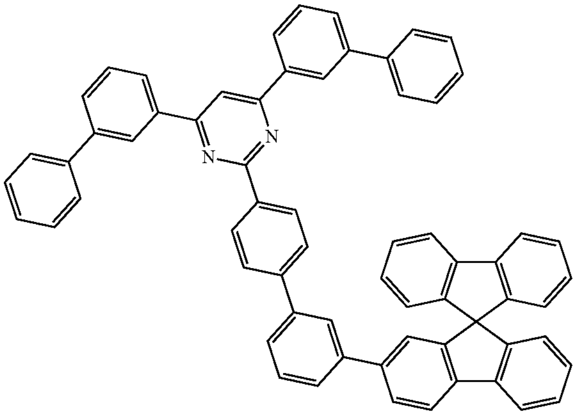
70
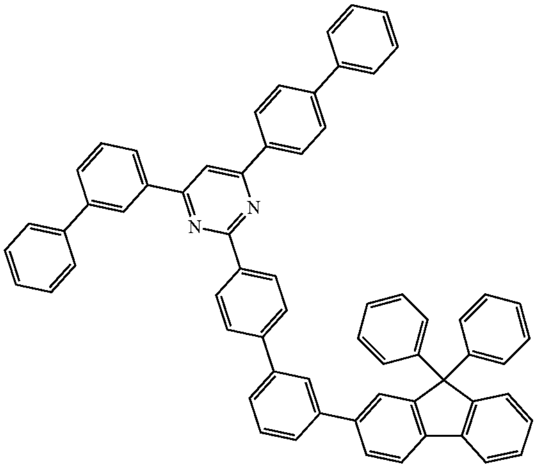
-continued
71
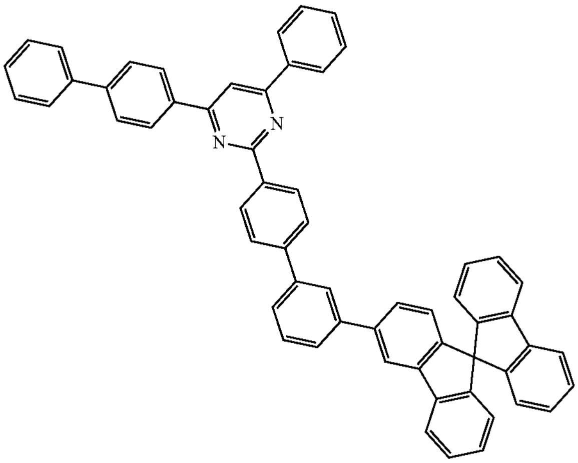
72
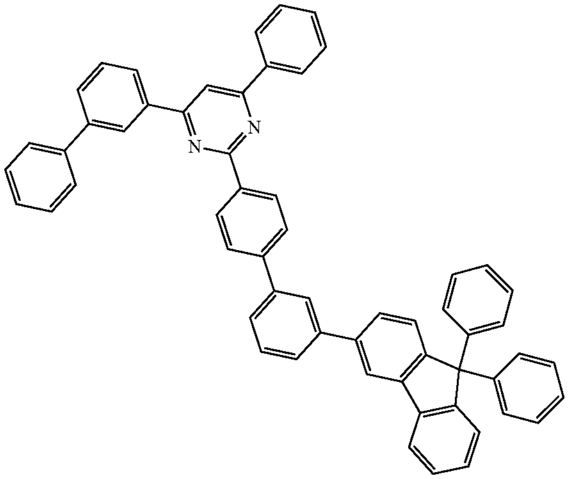
73
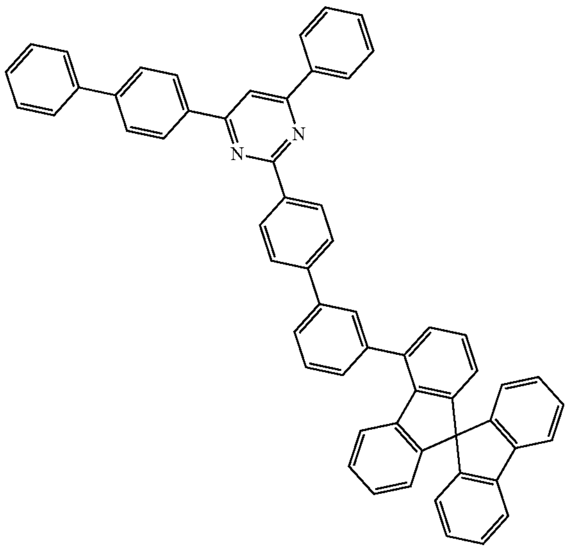

-continued
74
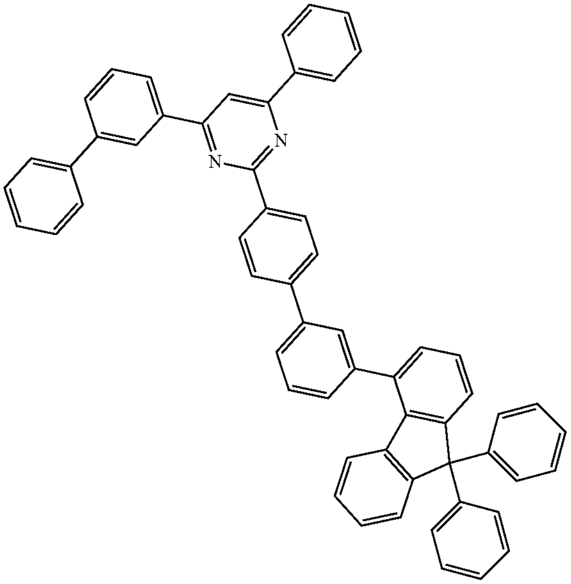
75
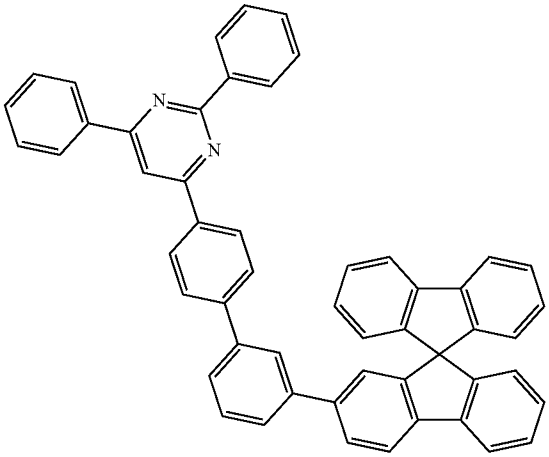
76
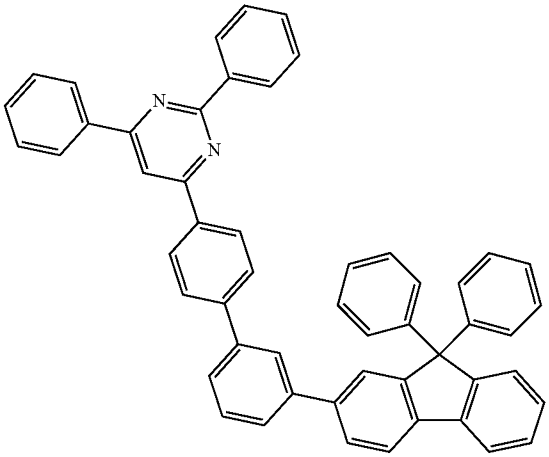
-continued
77
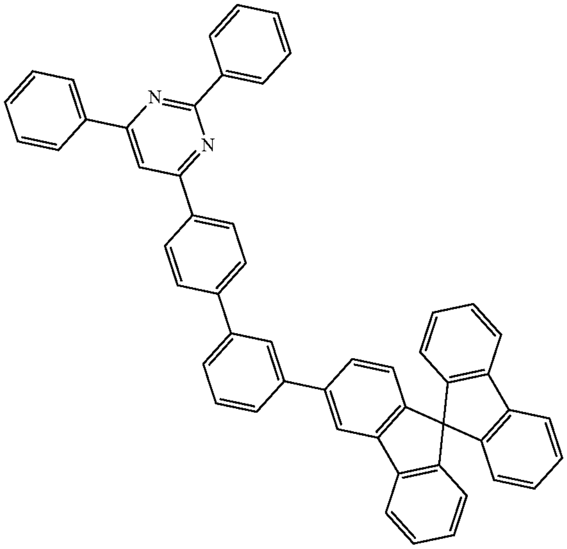
78
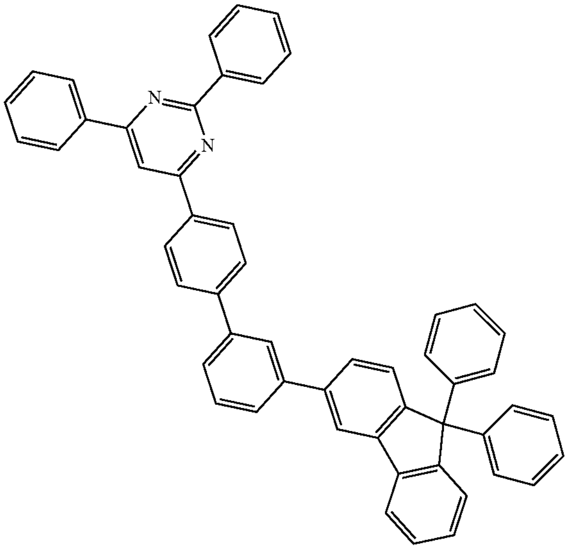

-continued
79
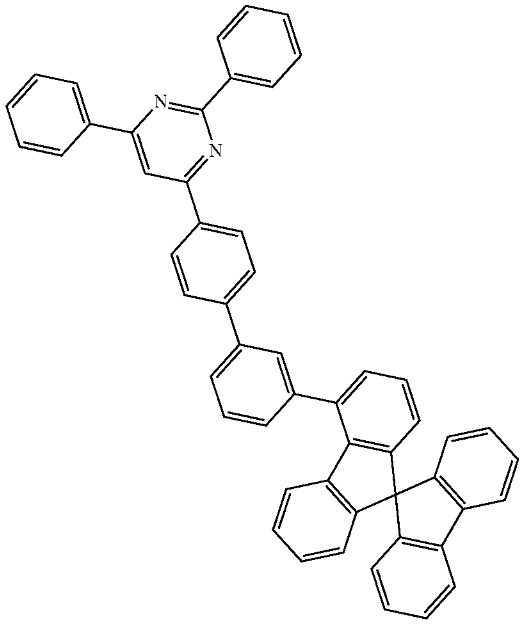
80
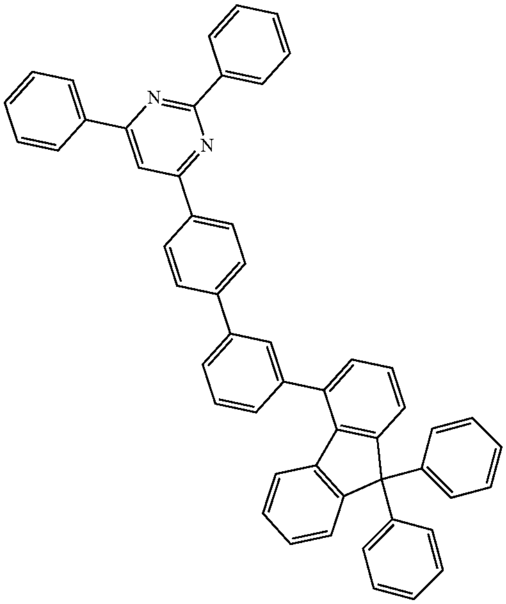
81
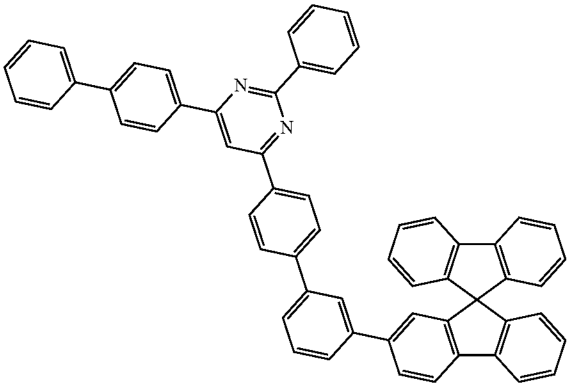
-continued
82
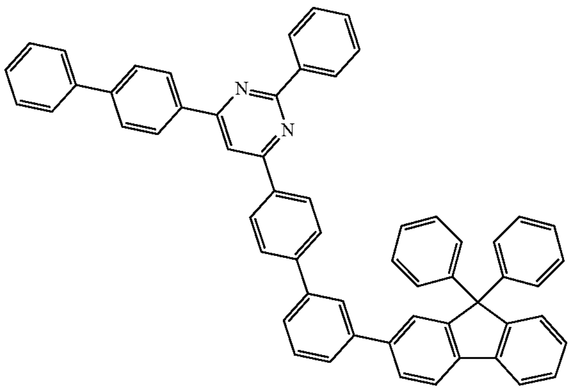
83
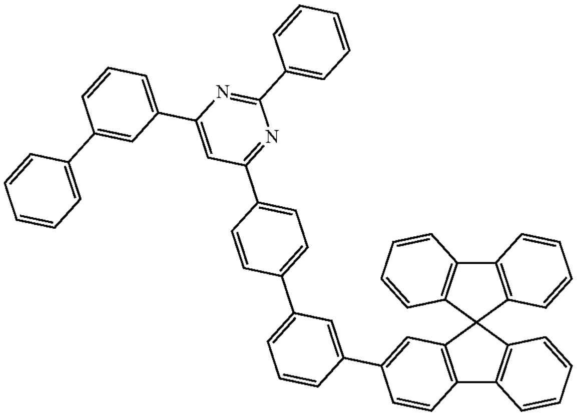
84
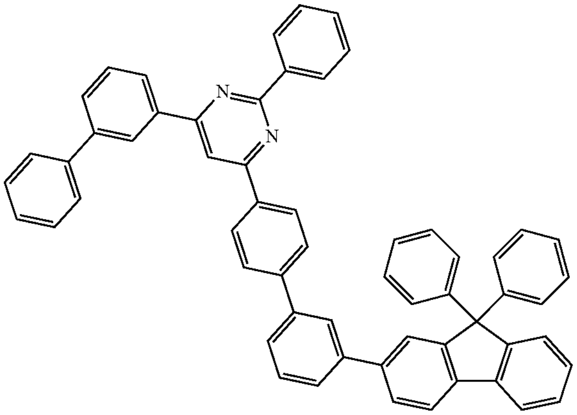

-continued
85
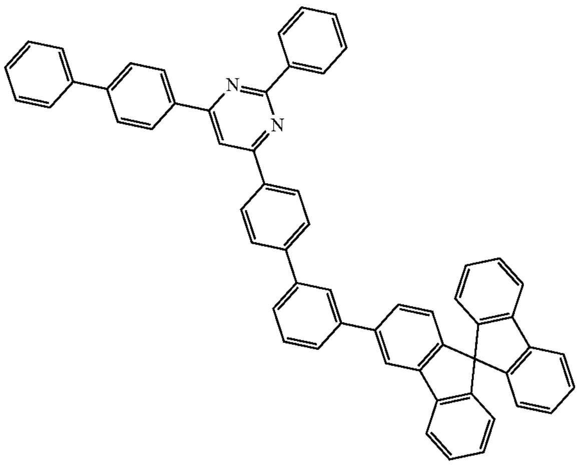
86
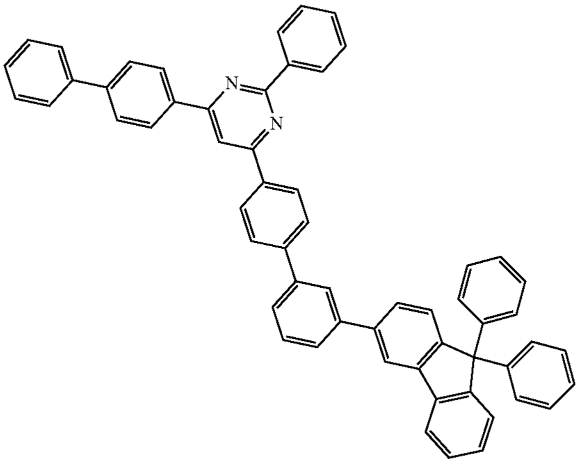
87
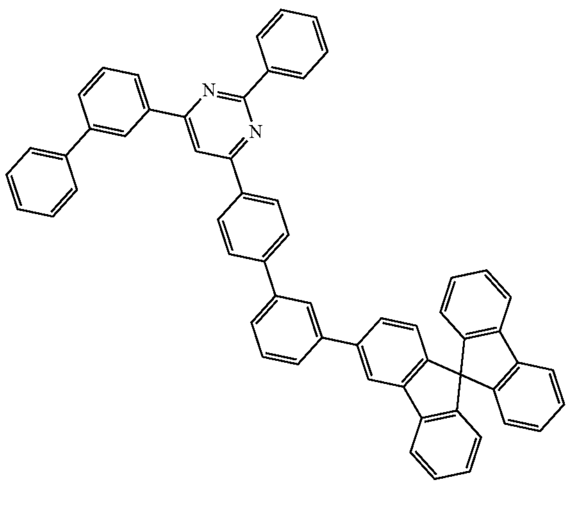
-continued
88
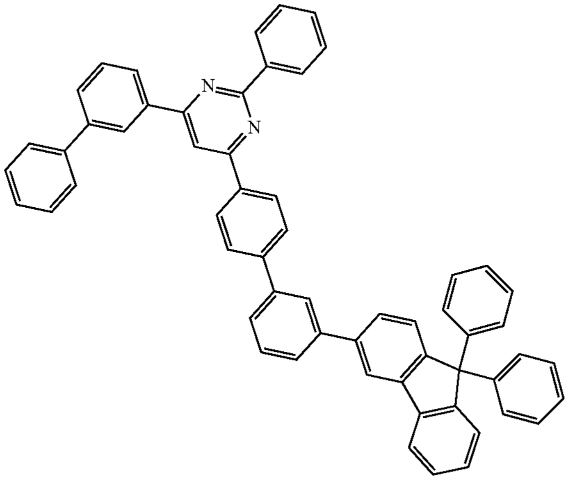
89
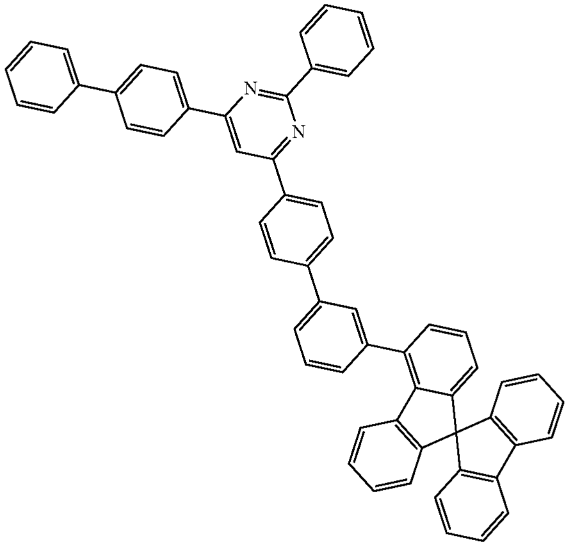
90
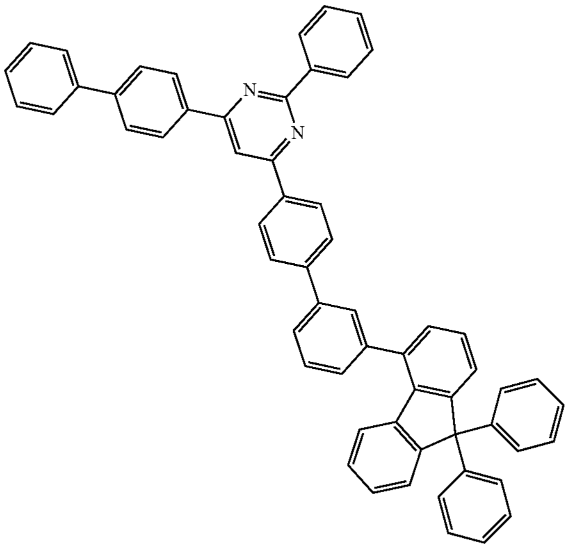

-continued
91
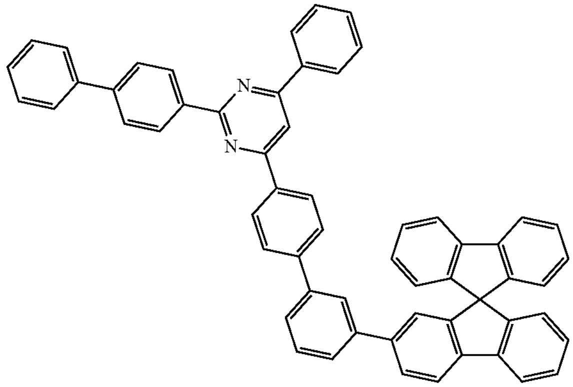
92
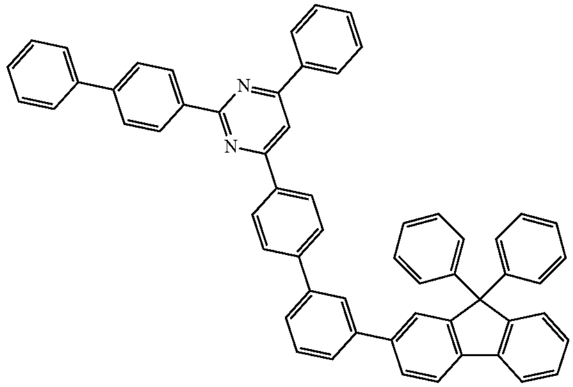
93
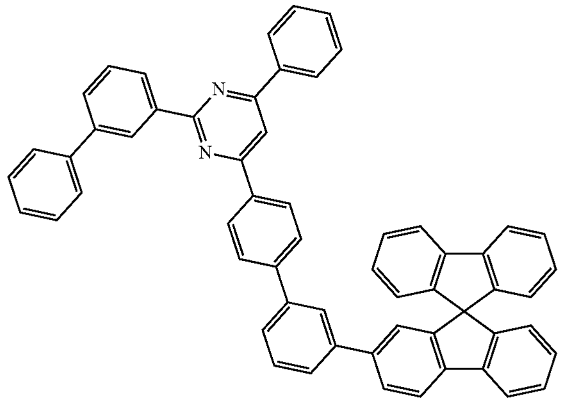
-continued
94
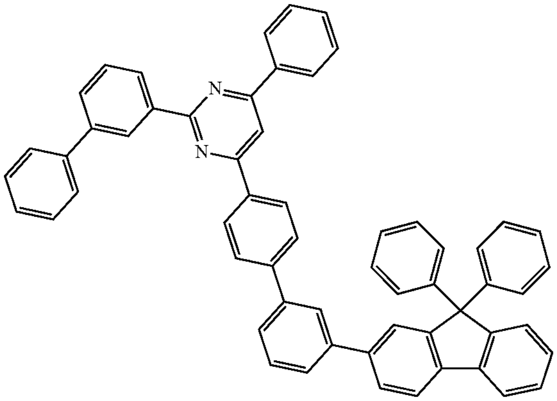
95
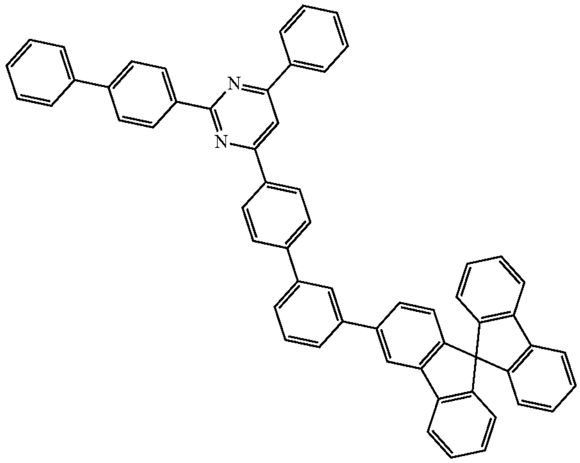
96
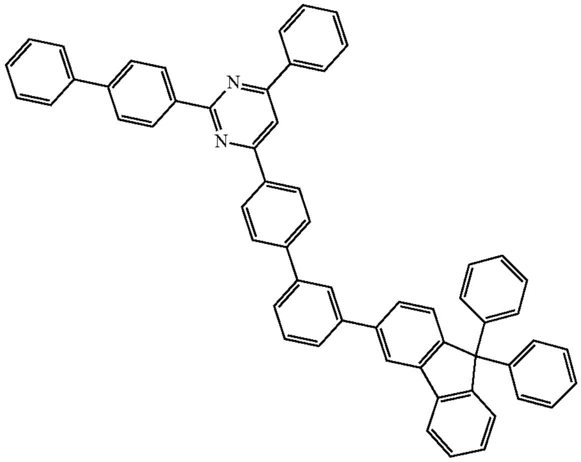

-continued
97
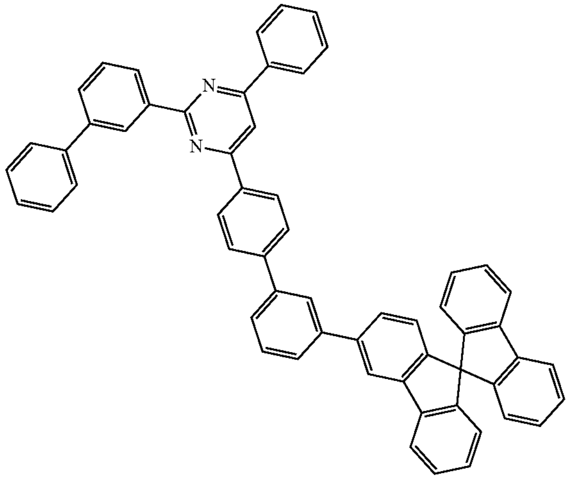
98
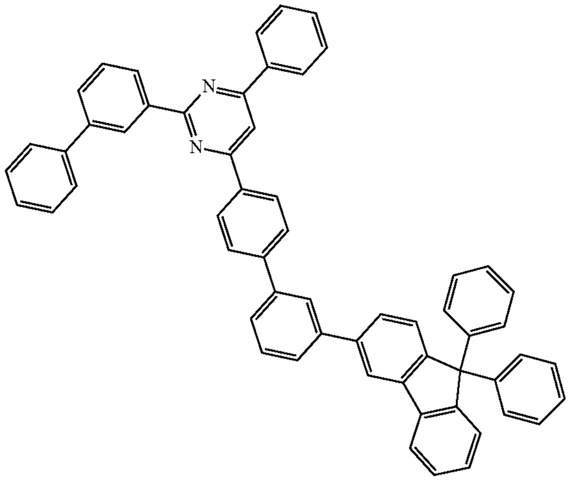
99
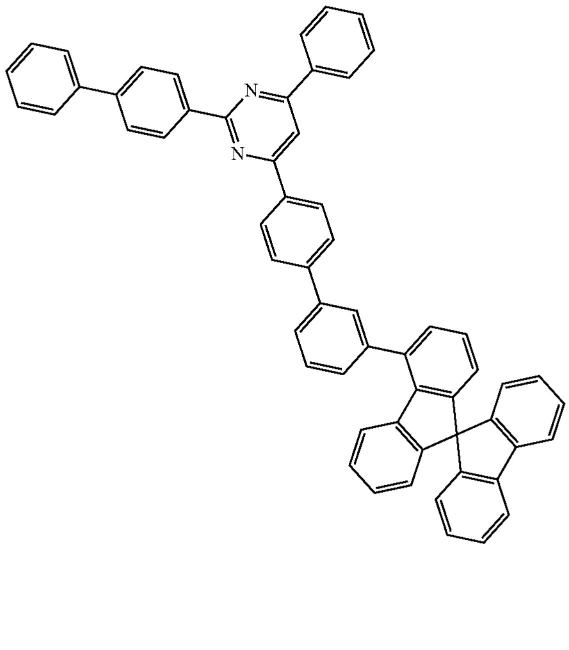
-continued
100
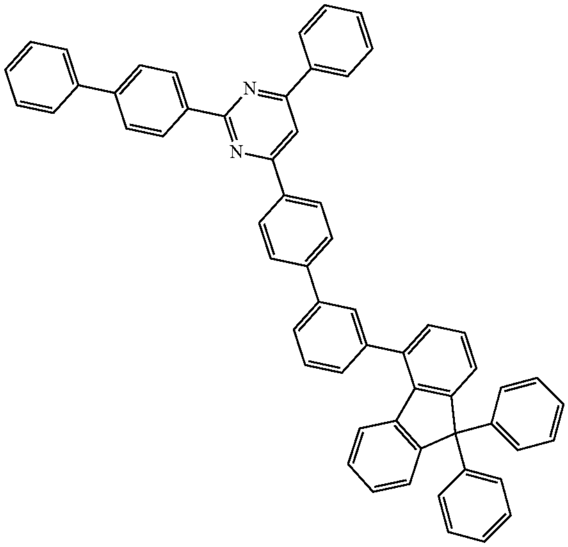
101
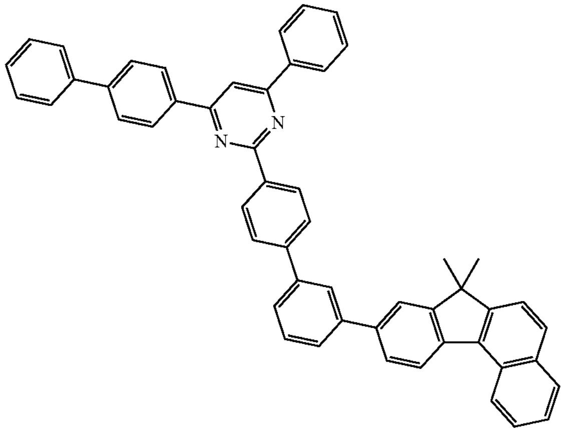
102
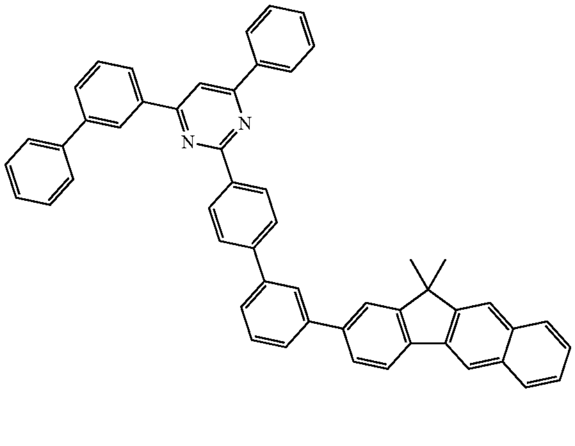

-continued
103
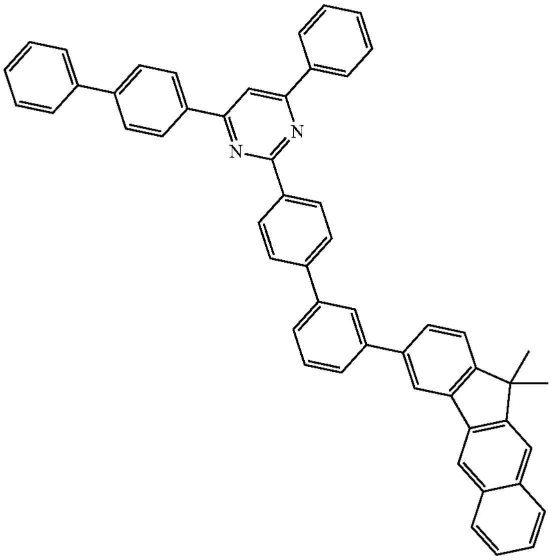
104
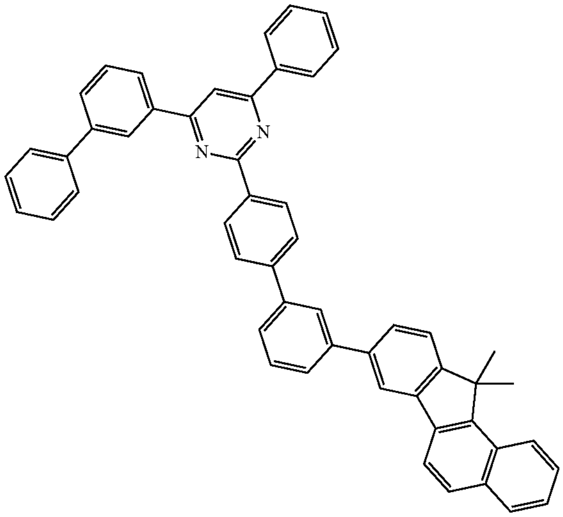
-continued
105
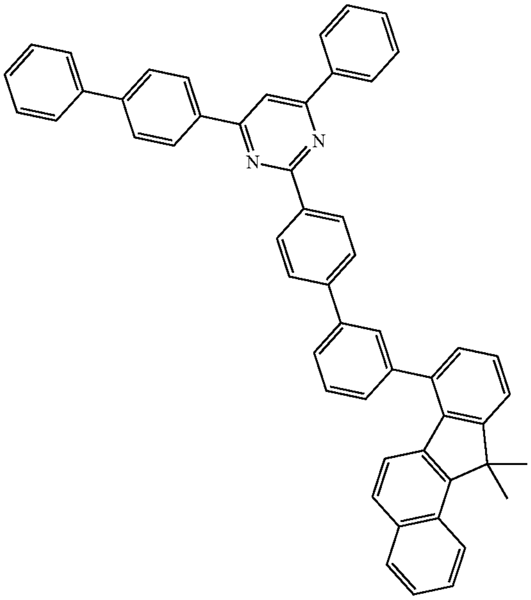
106
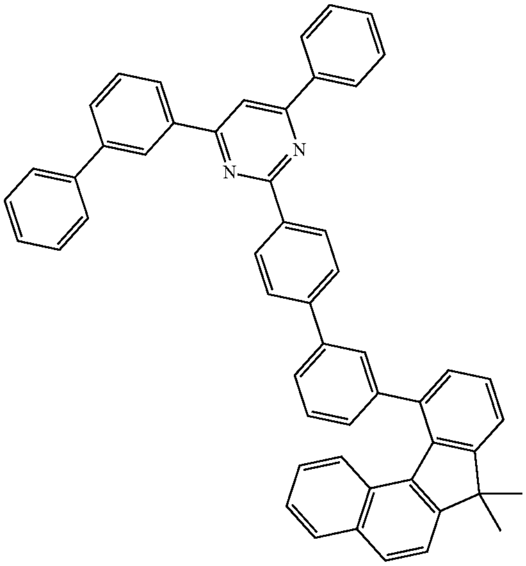
107
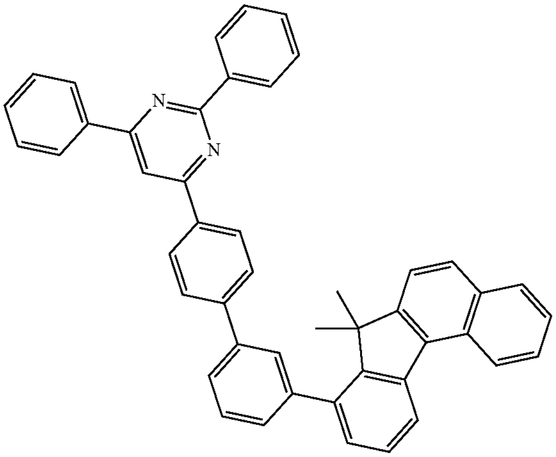

-continued
108
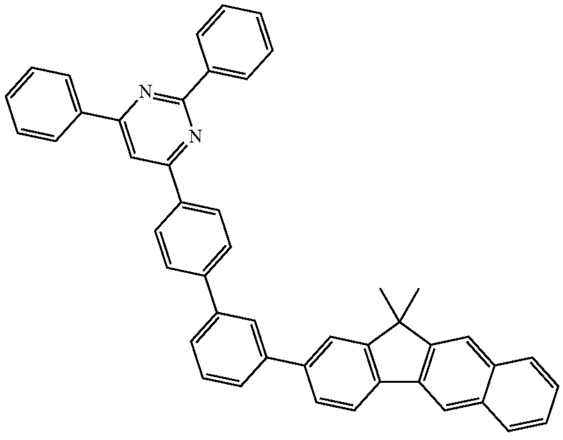
109
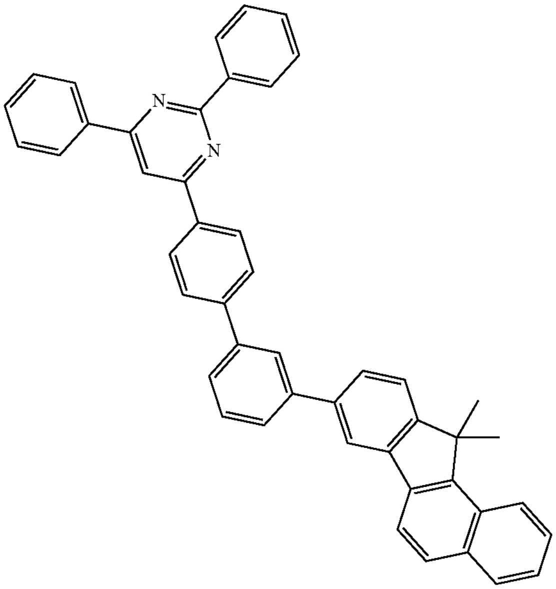
110
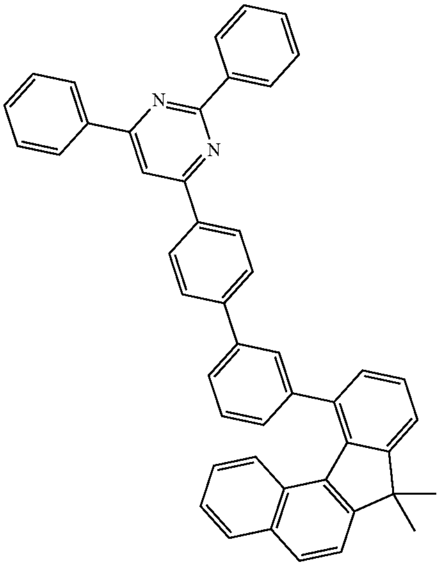
-continued
111
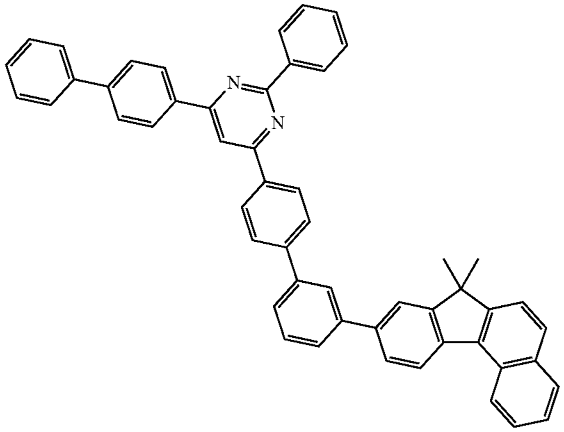
112
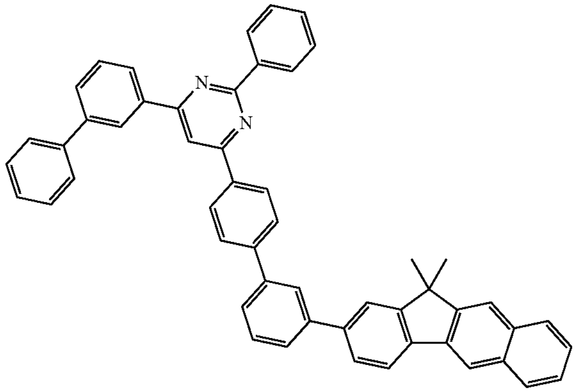
113
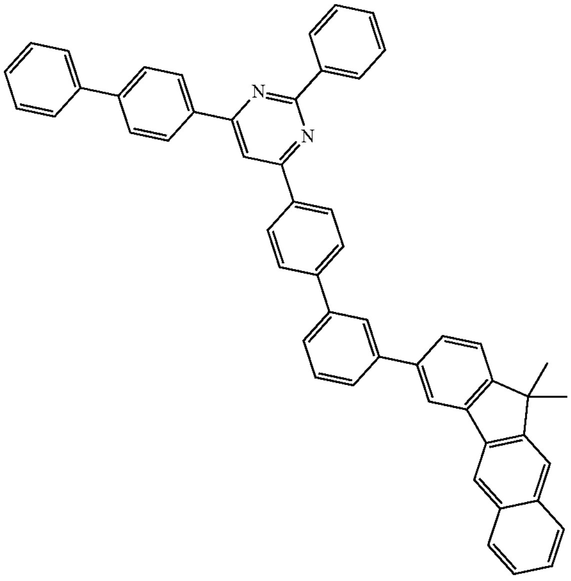

-continued
114
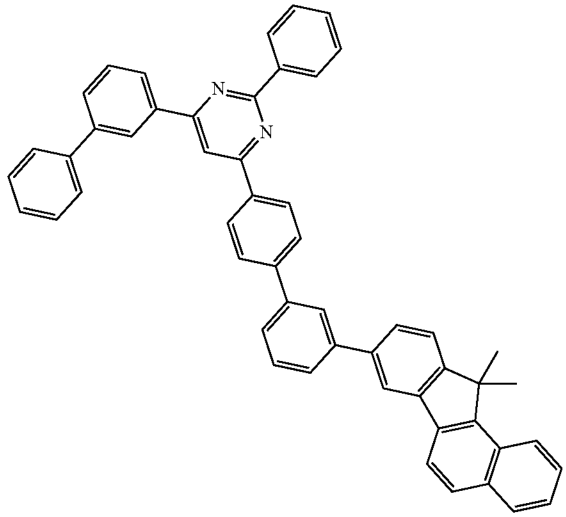
115
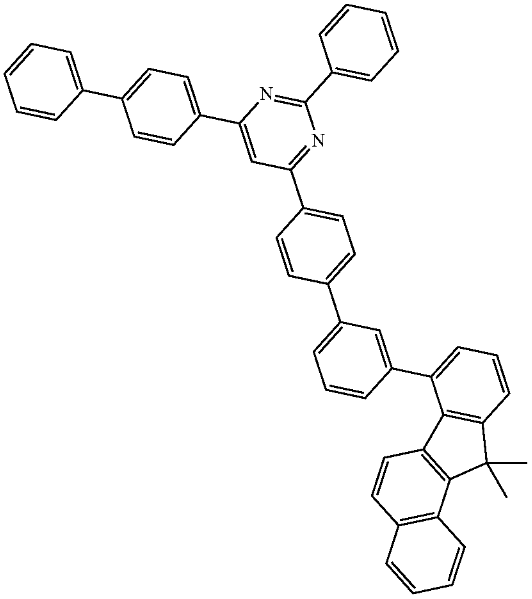
-continued
116
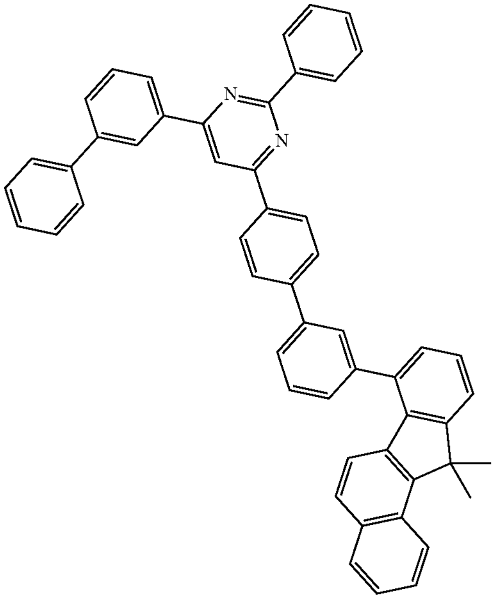
117
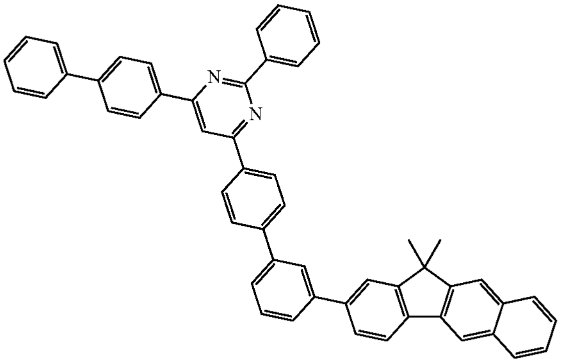
118
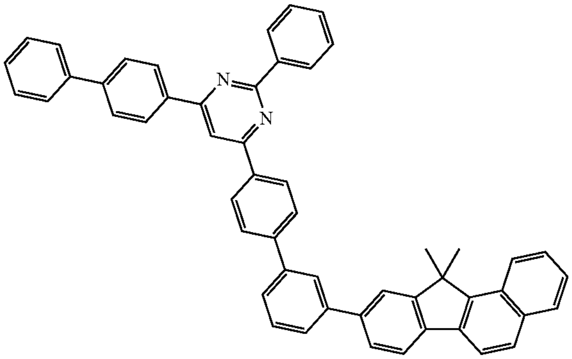

-continued
119
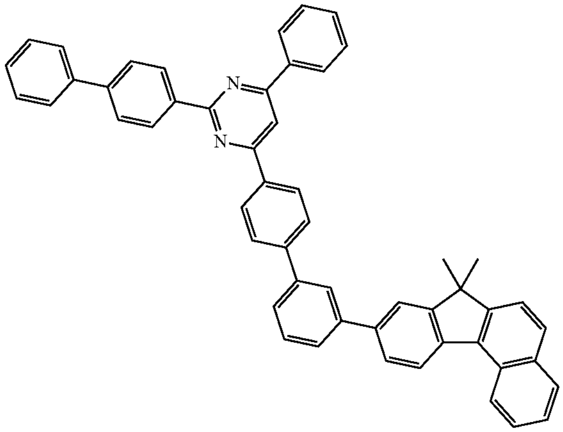
120
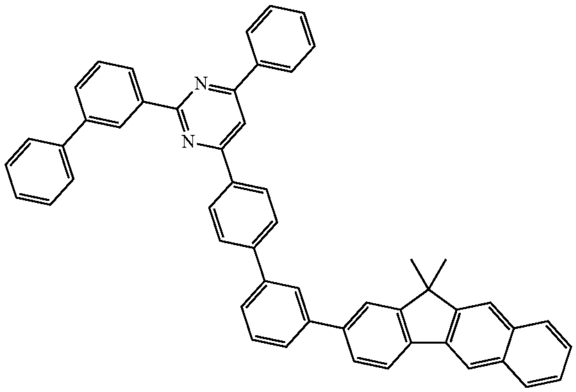
121
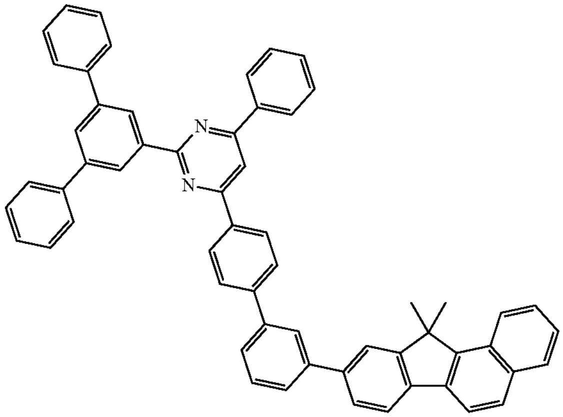
-continued
122
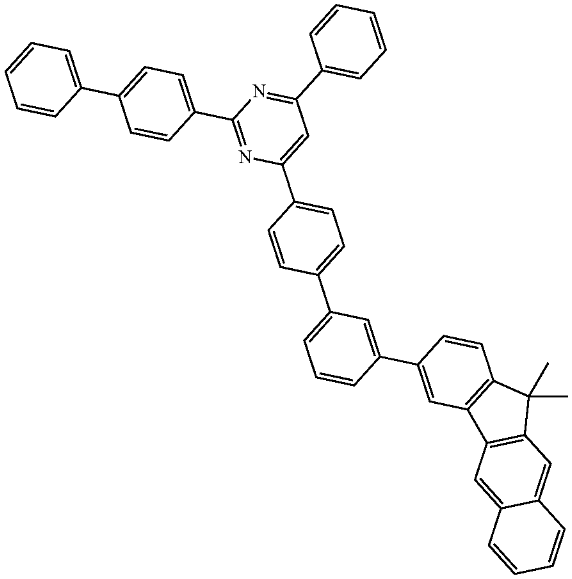
123
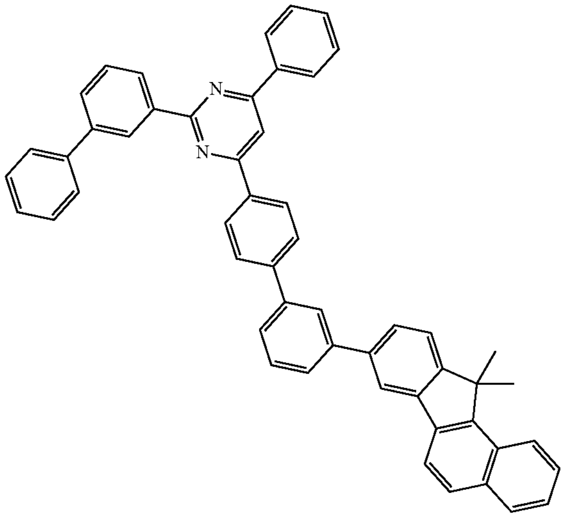

-continued
124
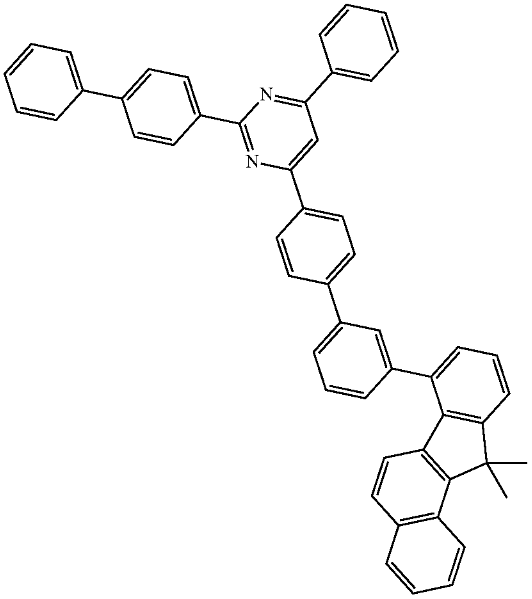
125
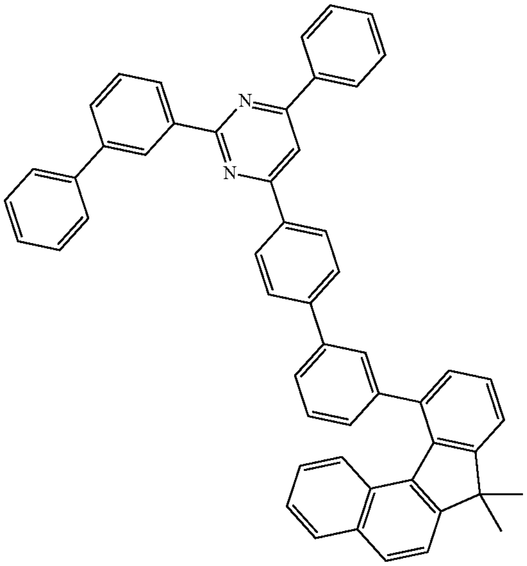
126
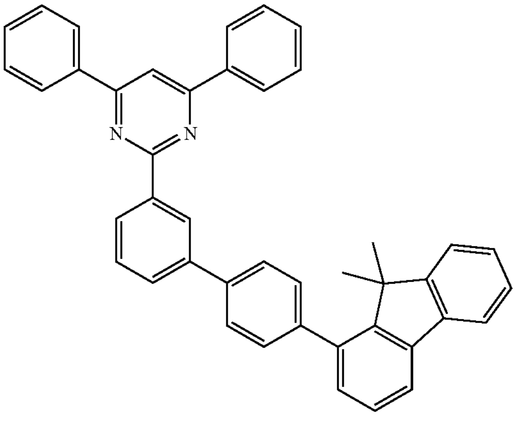
-continued
127
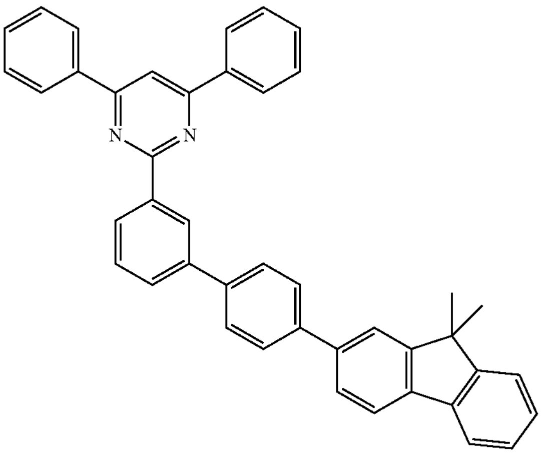
128
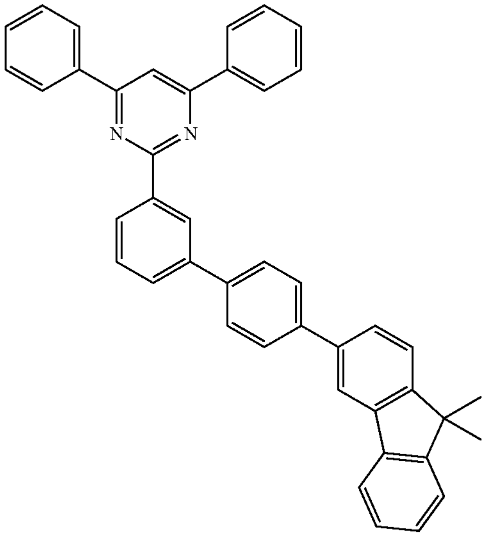
129
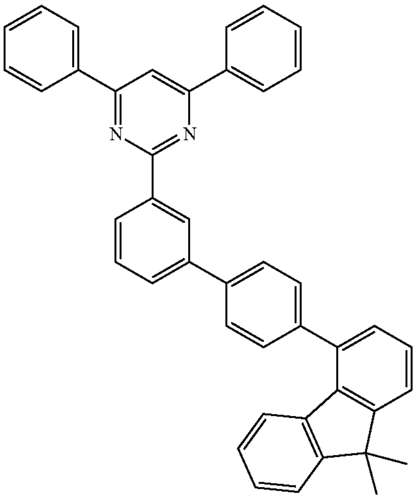

-continued
130
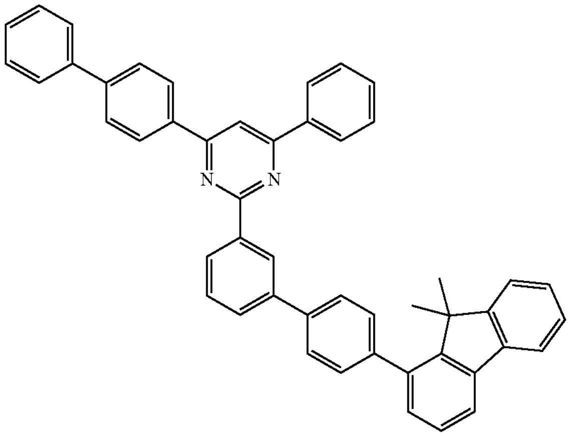
131
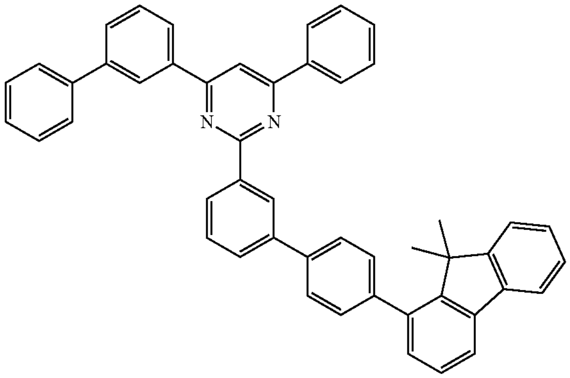
132
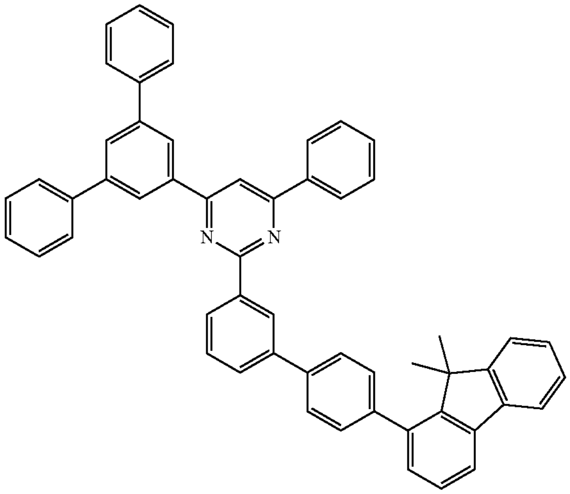
-continued
133
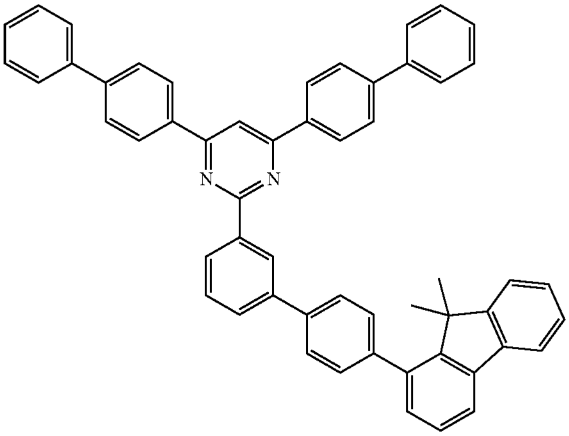
134
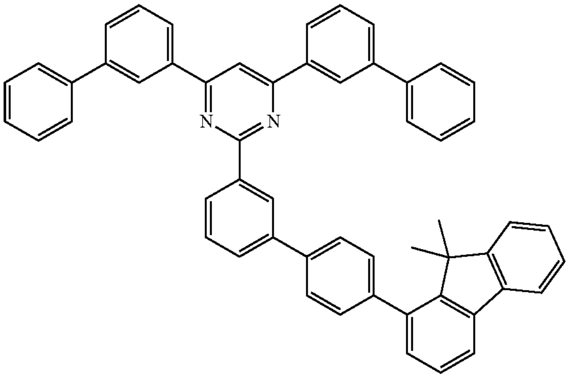
135
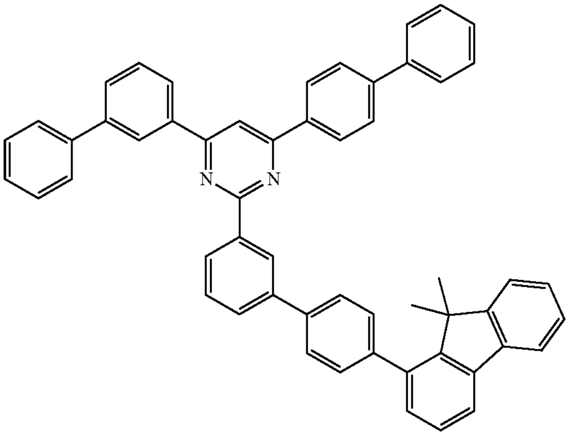

-continued
136
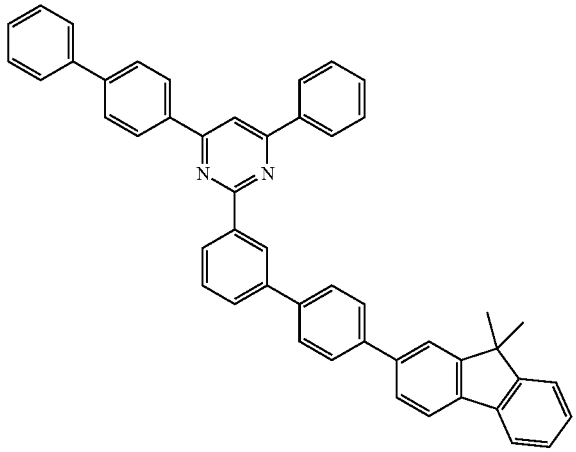
137
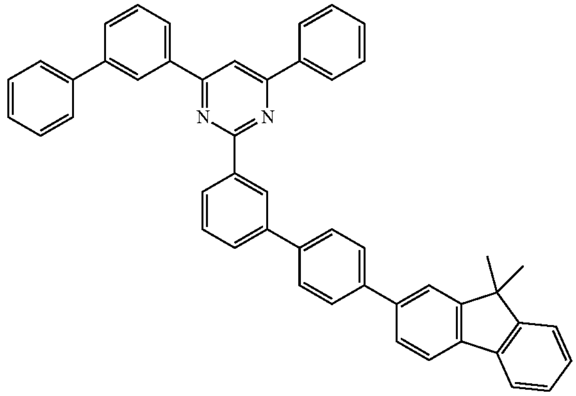
138
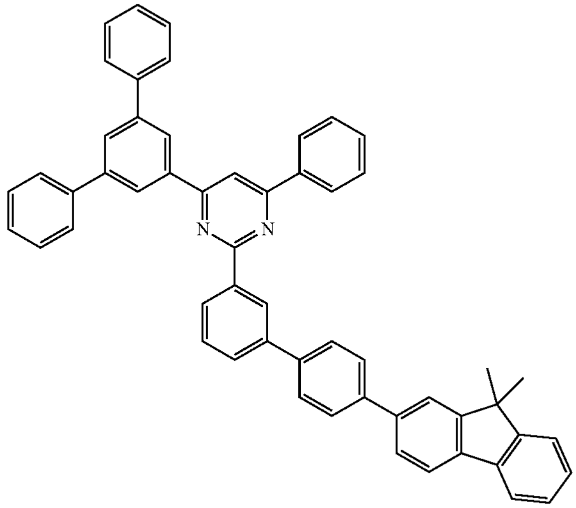
-continued
139
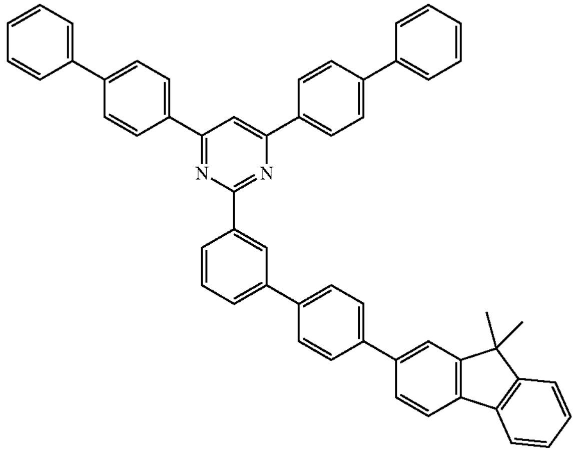
140
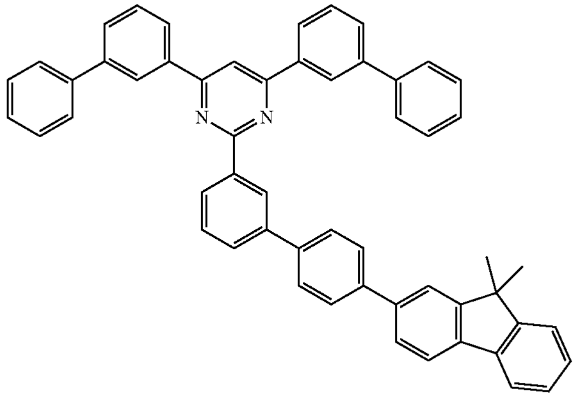
141
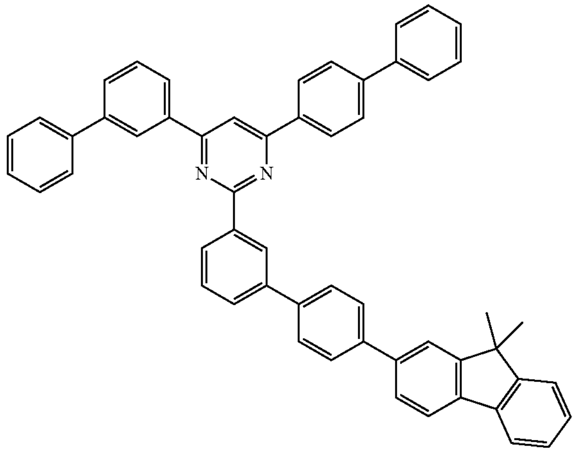

-continued
142
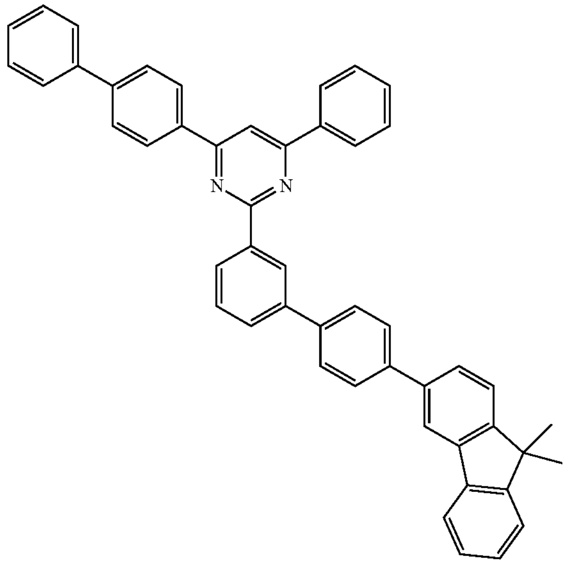
143
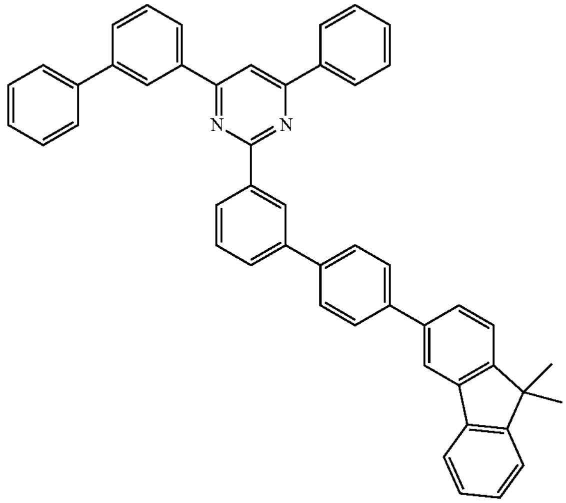
-continued
144
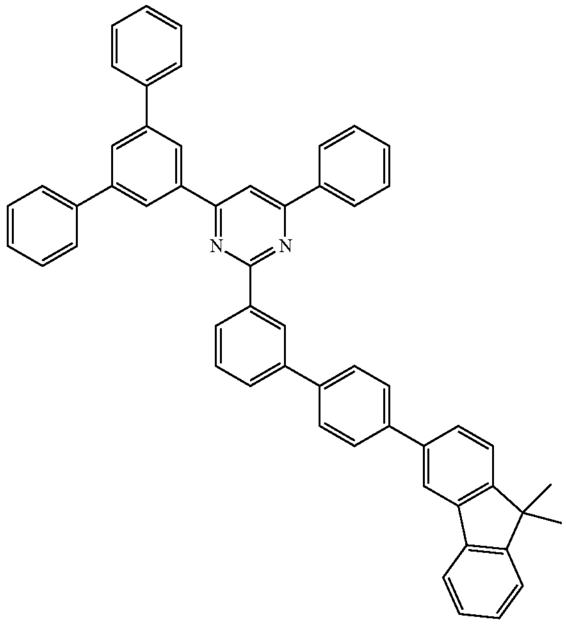
145
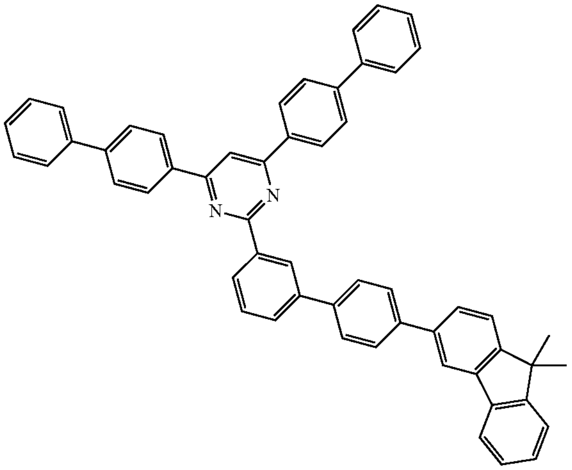
146
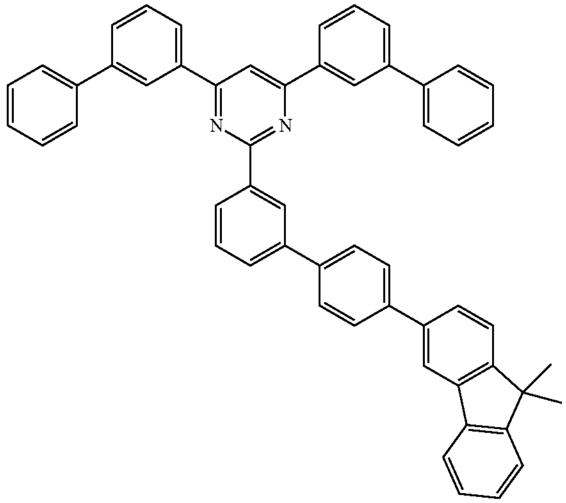

-continued
147
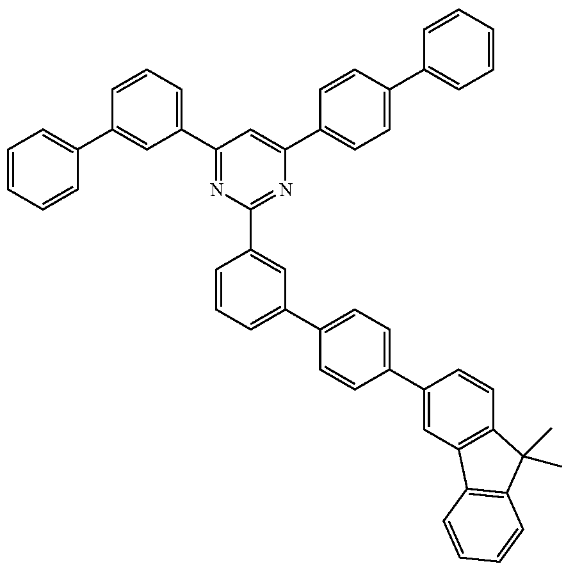
148
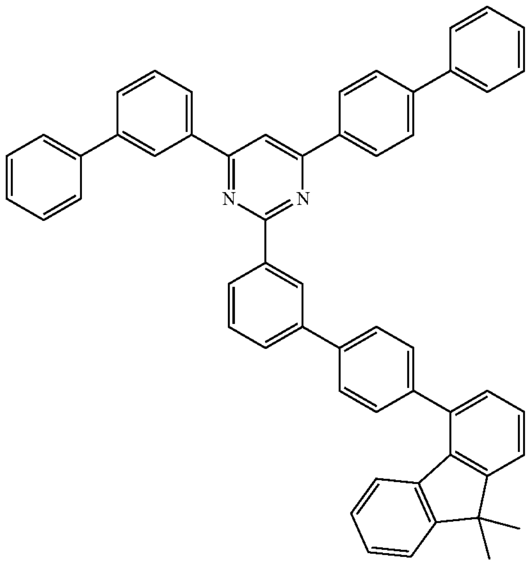
-continued
149
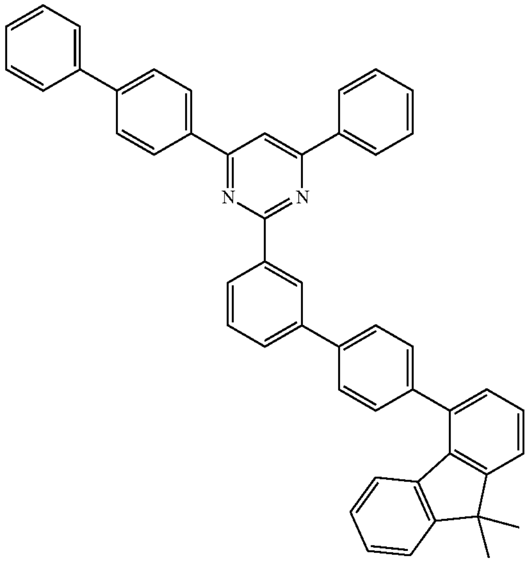
150
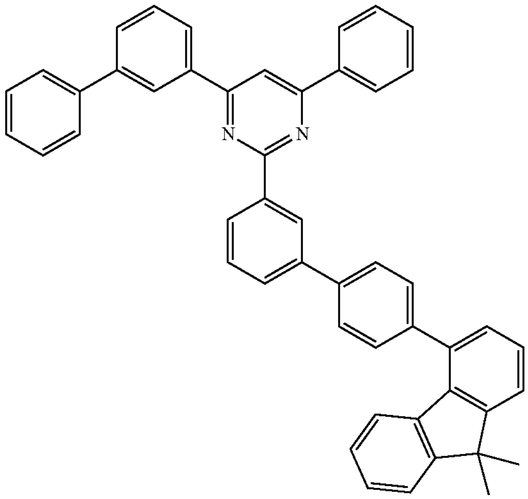
151
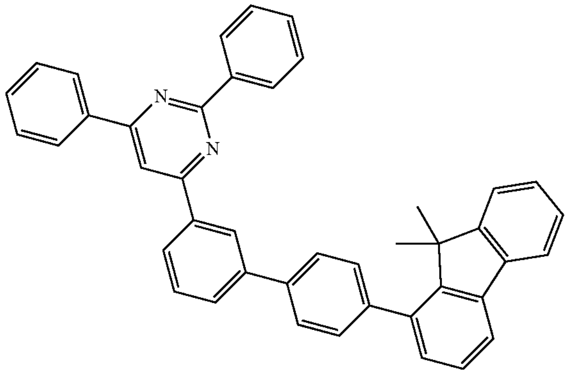

-continued
152
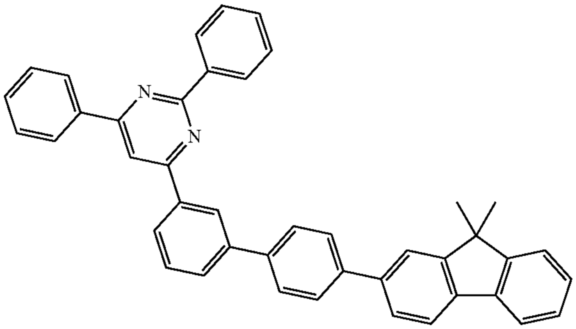
153
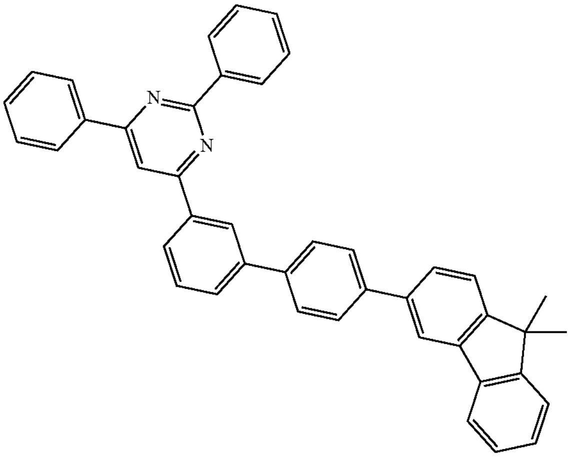
154
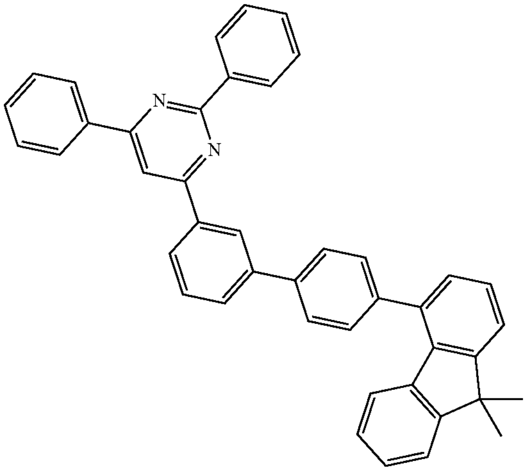
155
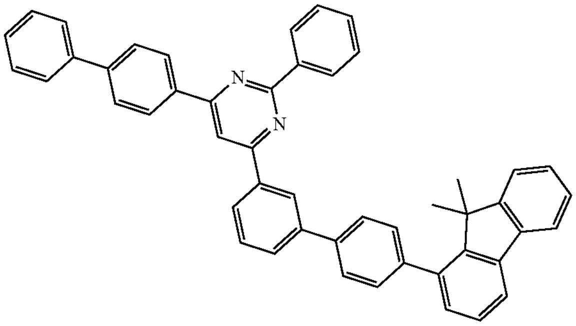
-continued
156
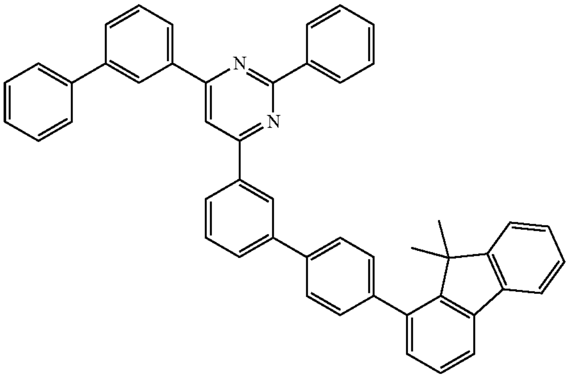
157
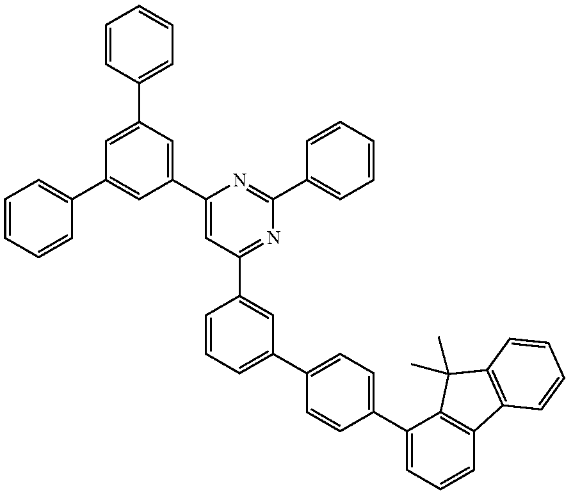
158
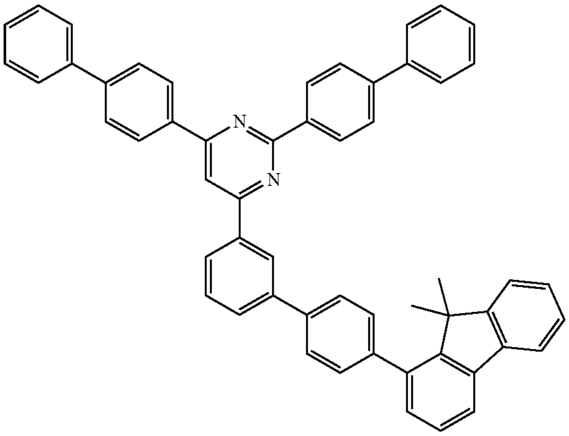

-continued
159
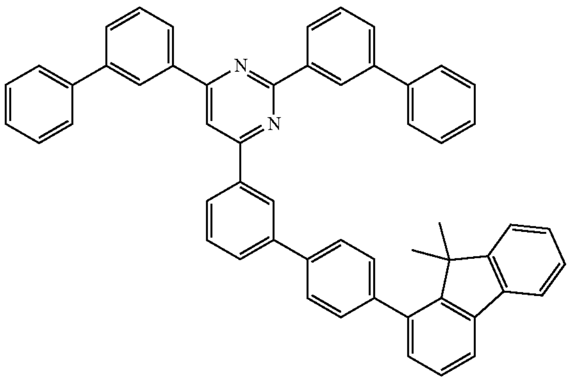
160
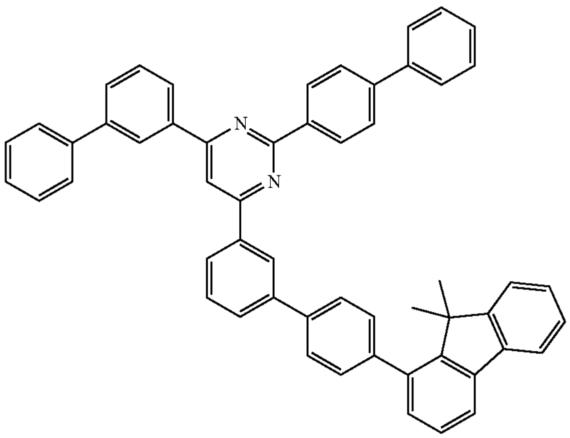
161
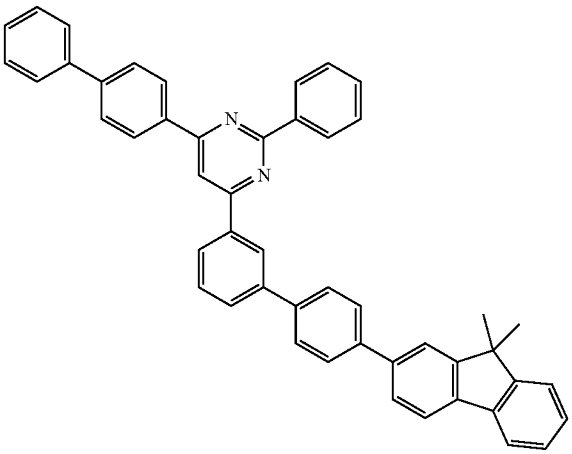
-continued
162
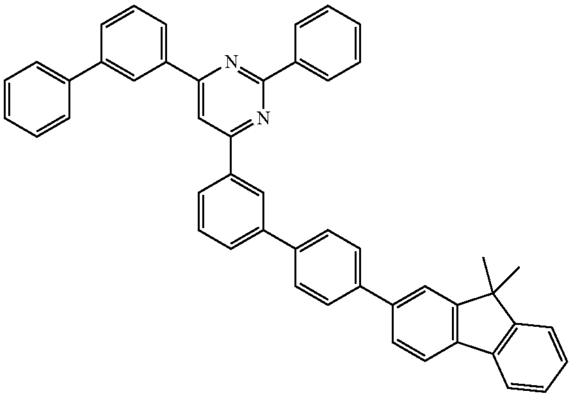
163
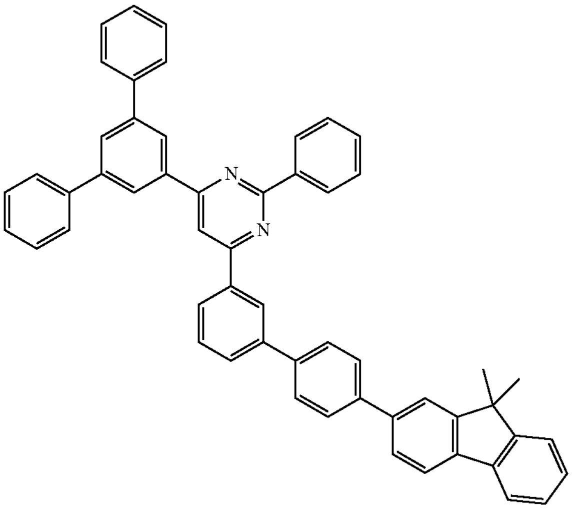
164
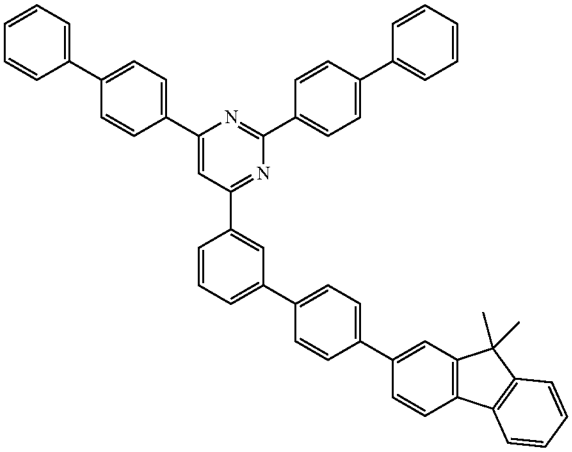

-continued
165
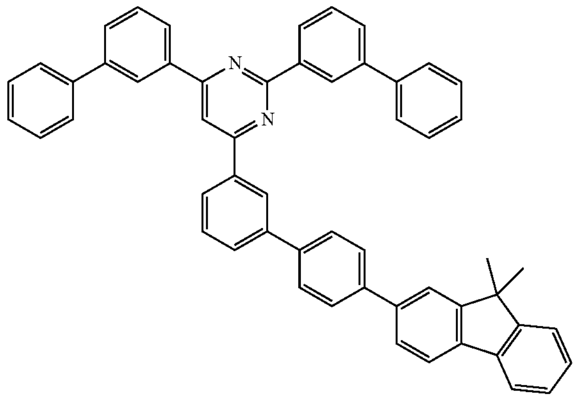
166
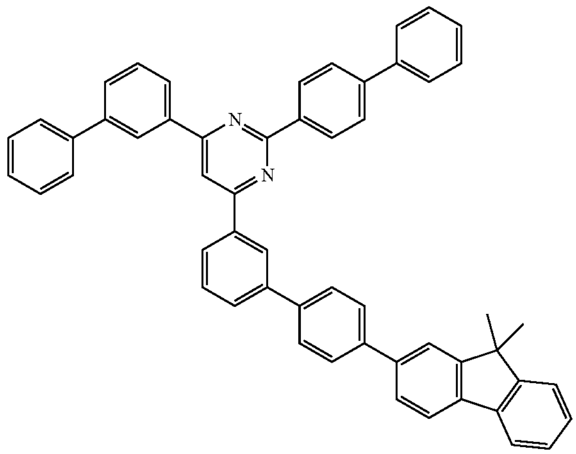
167
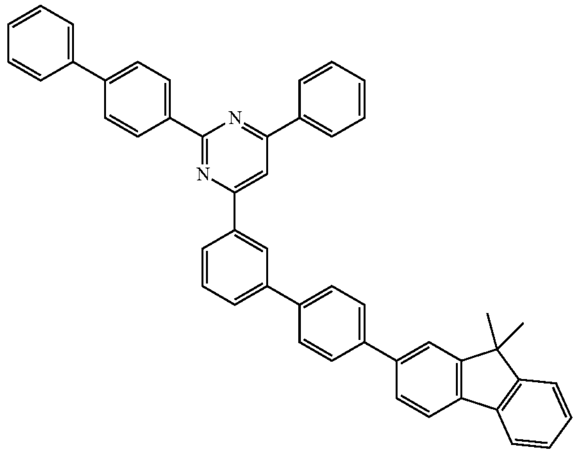
-continued
168
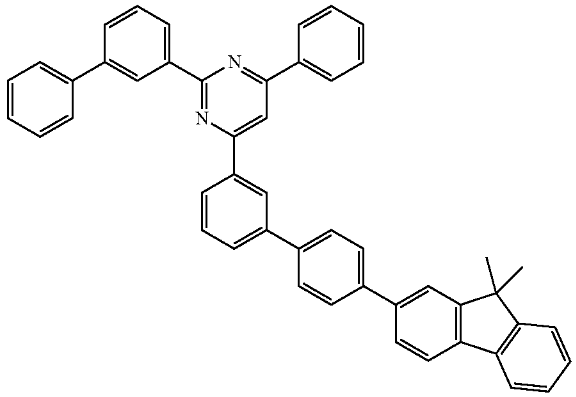
169
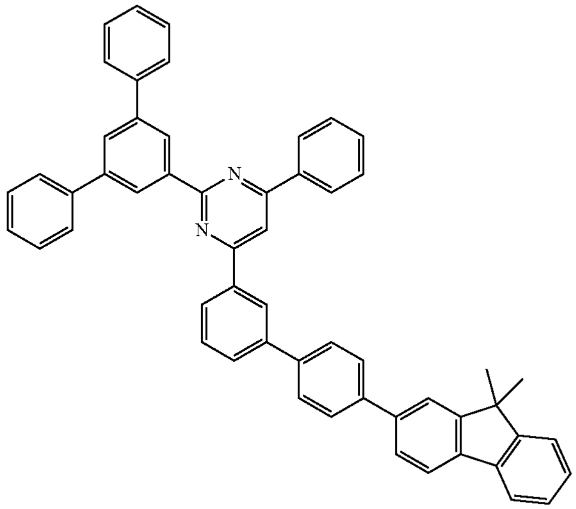
170
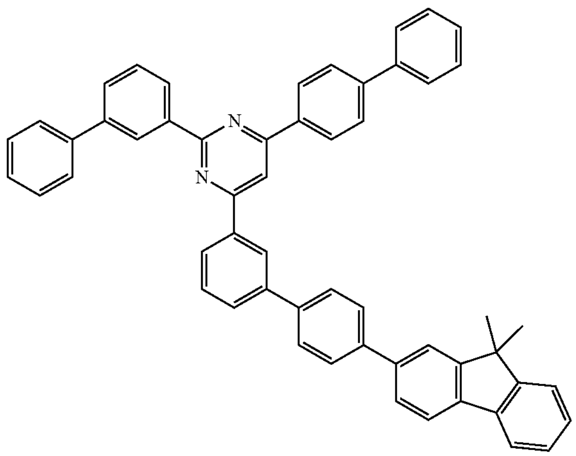

-continued
171
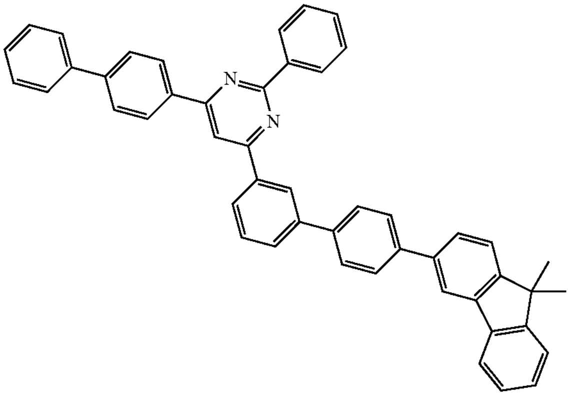
172
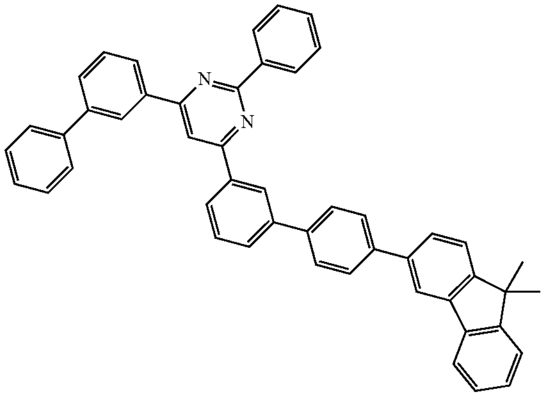
173
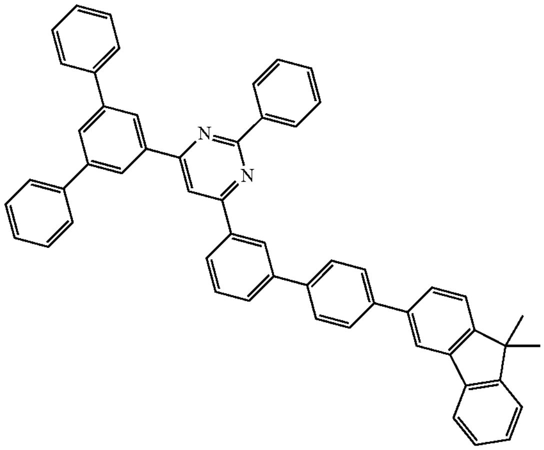
-continued
174
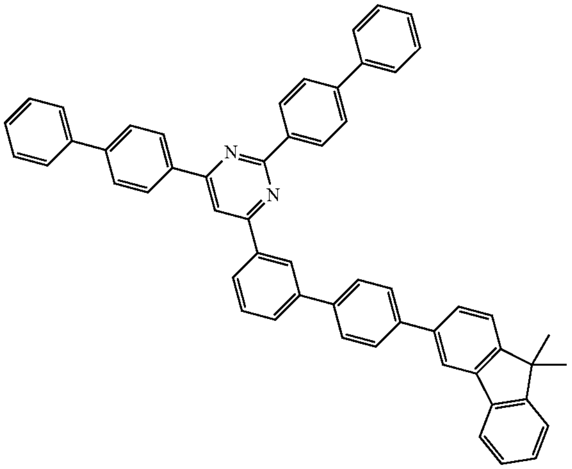
175
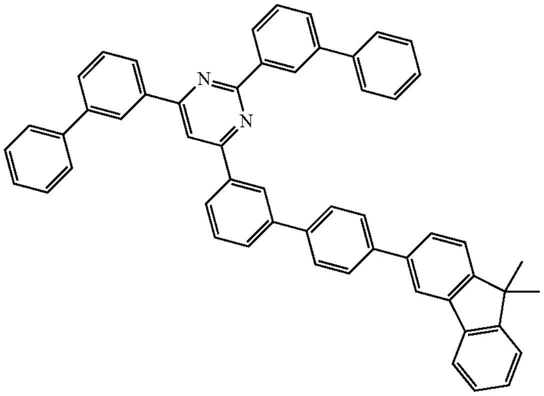
176
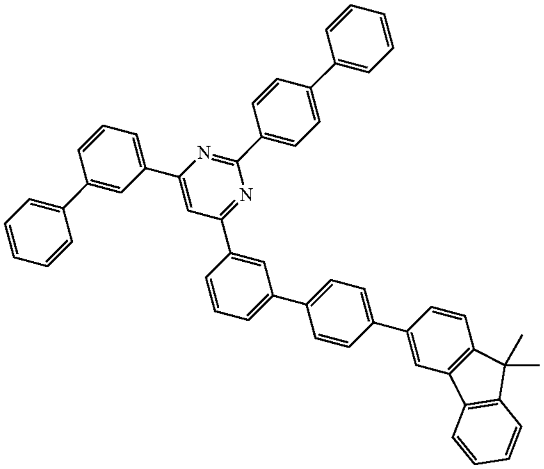

-continued
177
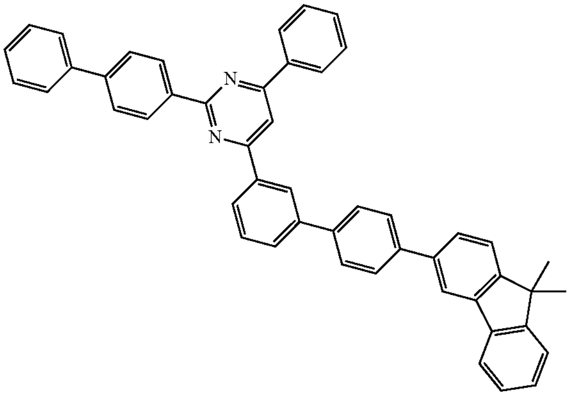
178
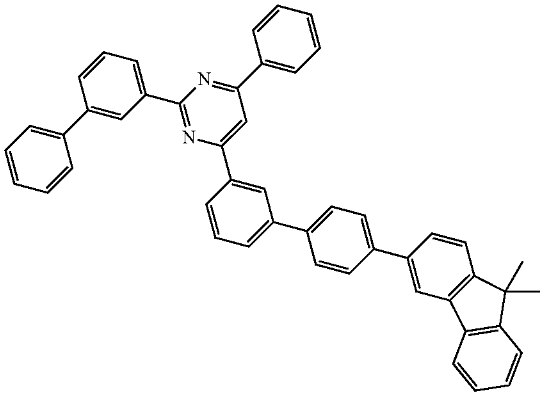
179
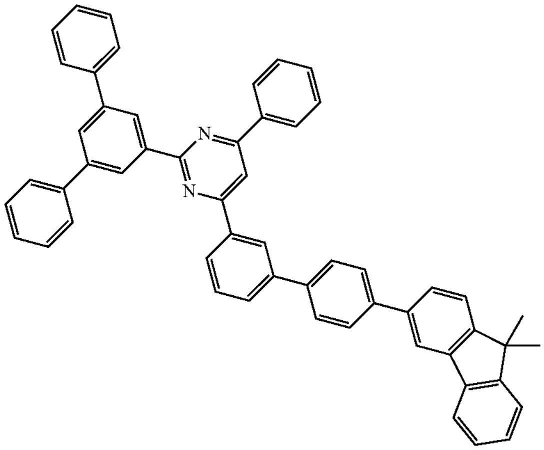
-continued
180
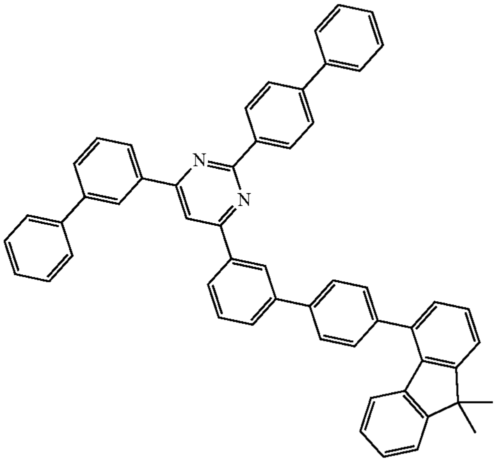
181
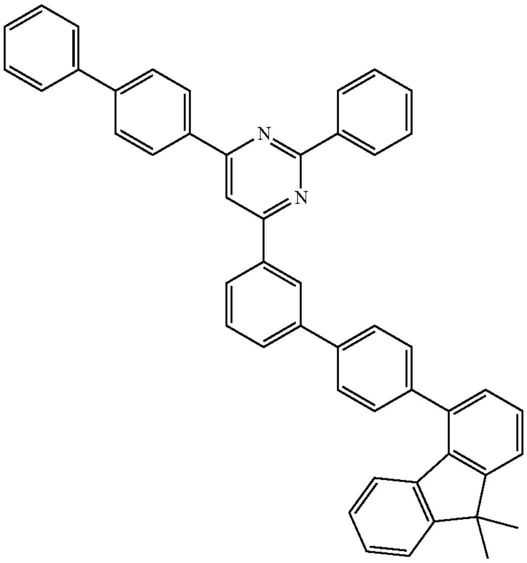
182
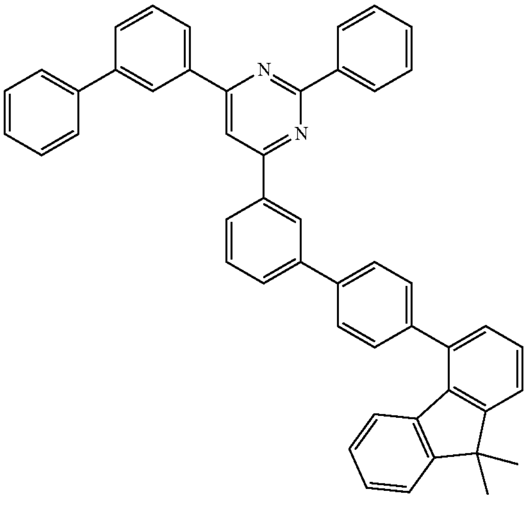

183
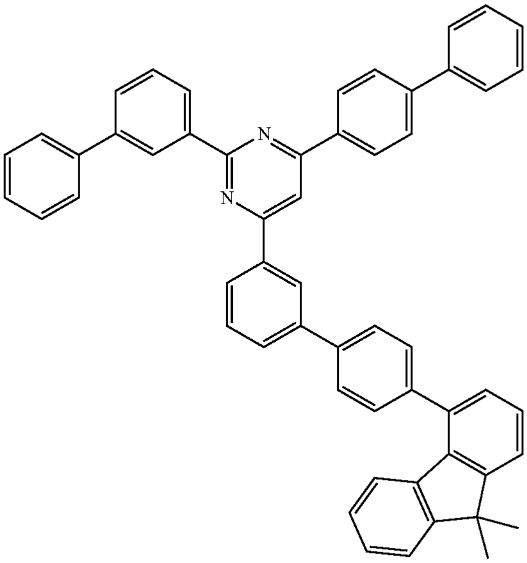
184
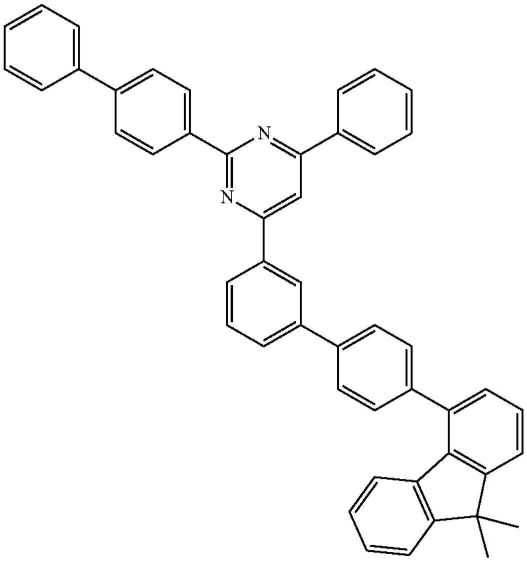
185
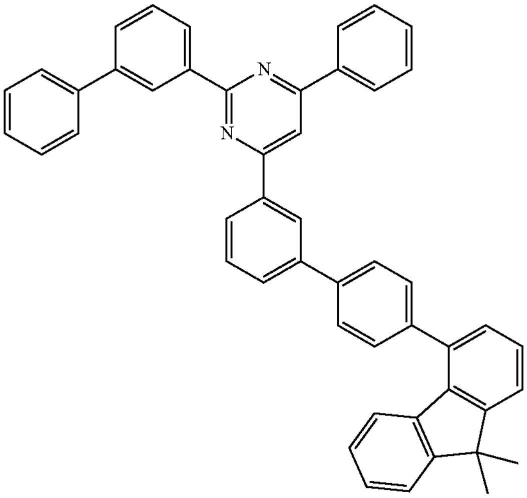
186
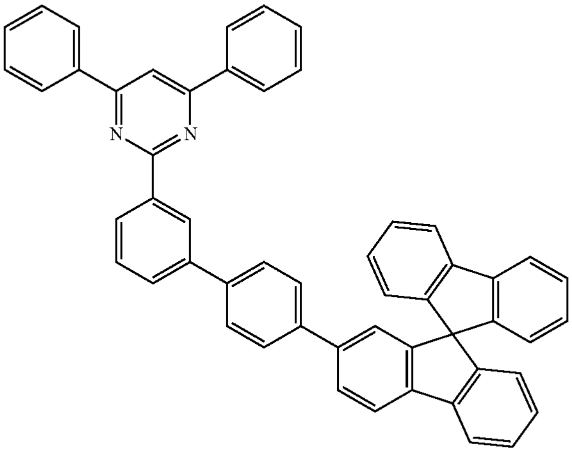
187
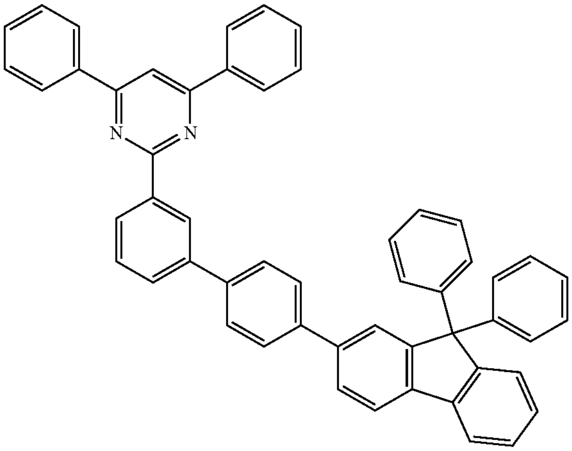

-continued
188
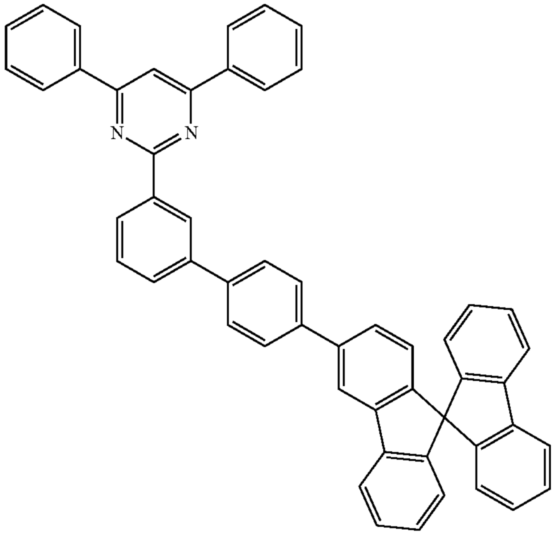
189
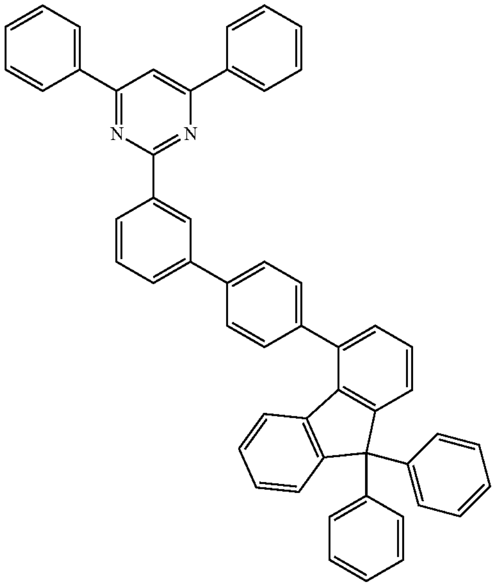
190
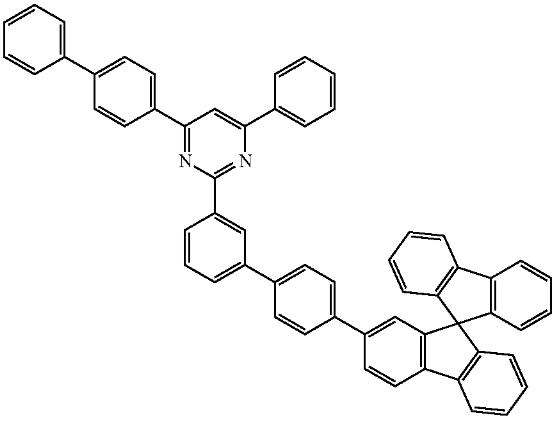
-continued
191
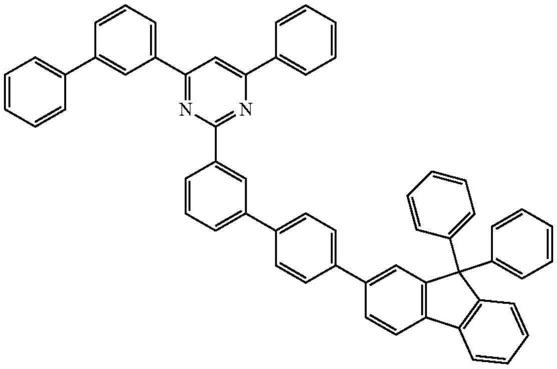
192
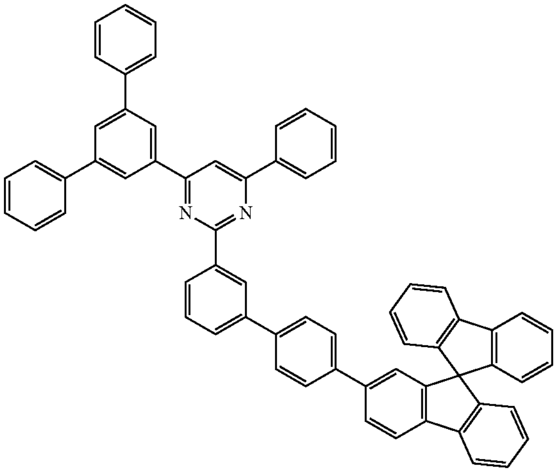
193
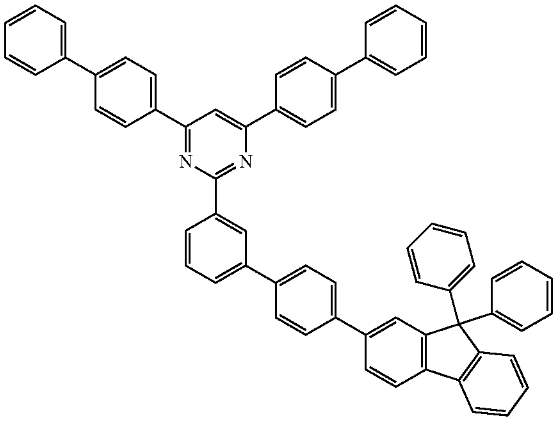

-continued
194
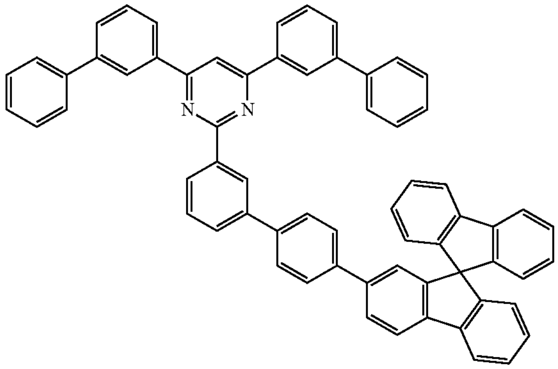
195
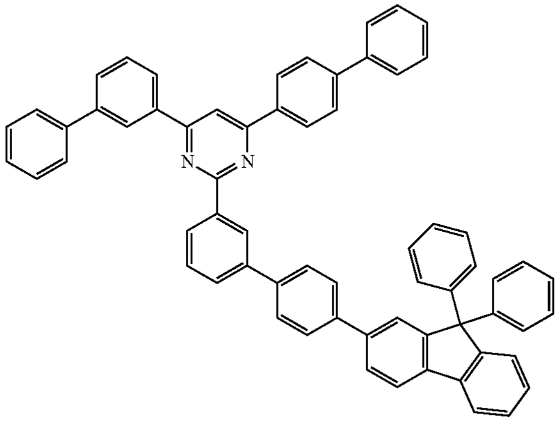
196
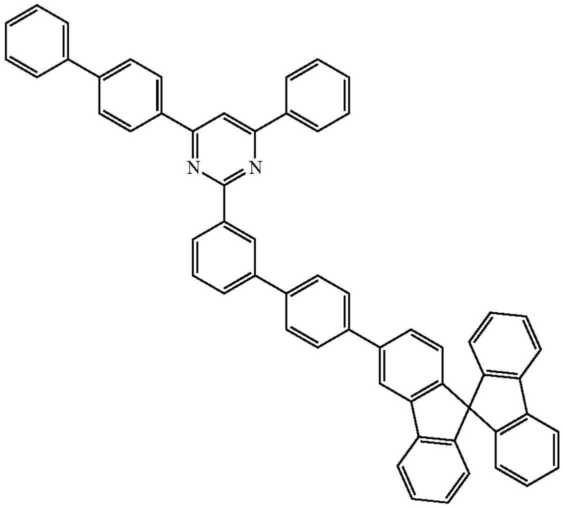
-continued
197
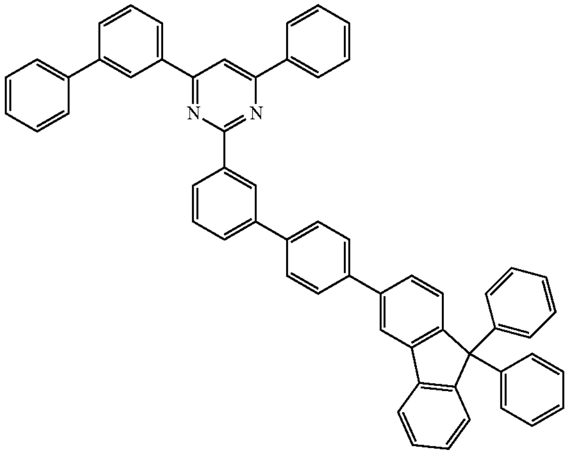
198
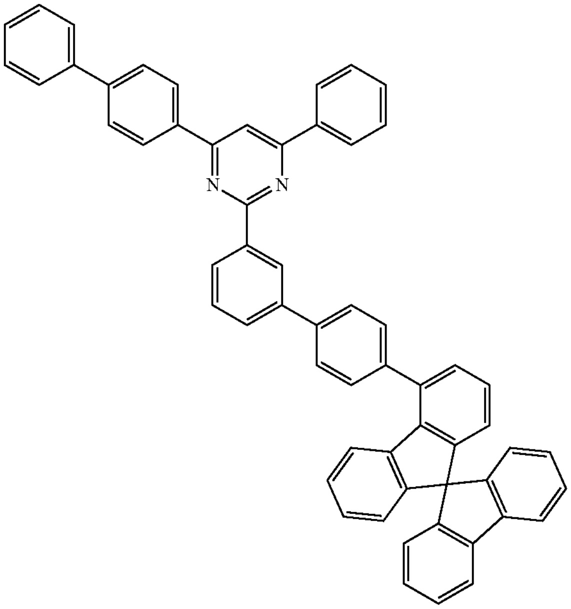

-continued
199
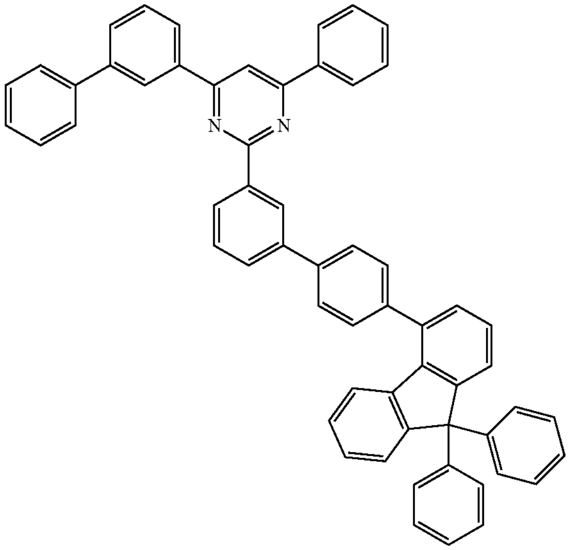
200
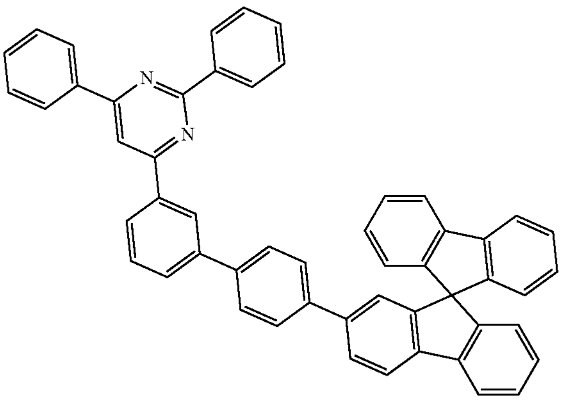
226
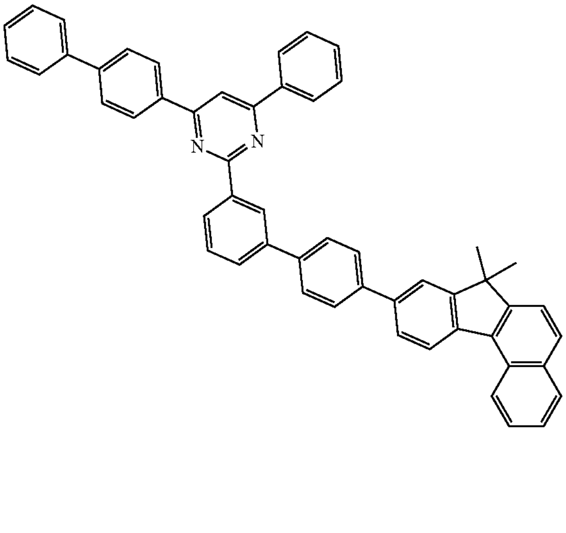
-continued
227
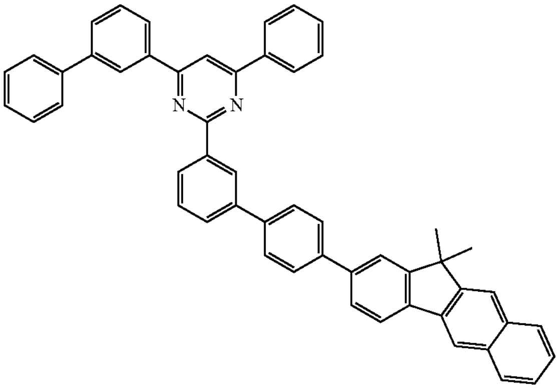
228
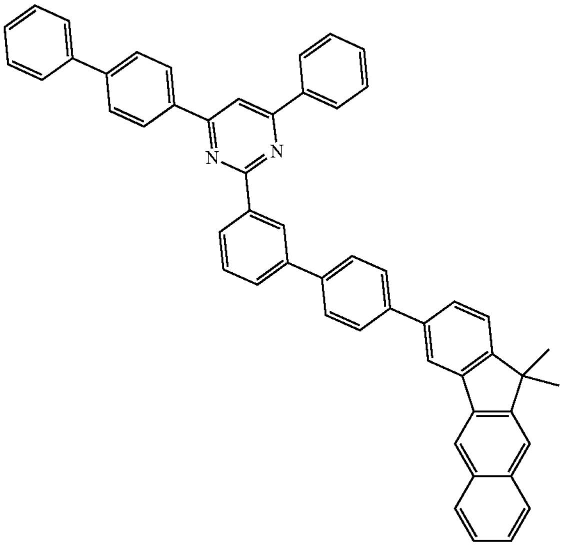
229
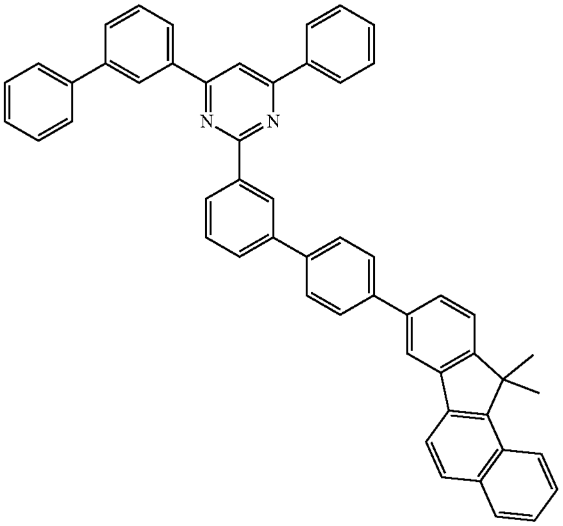

-continued
230
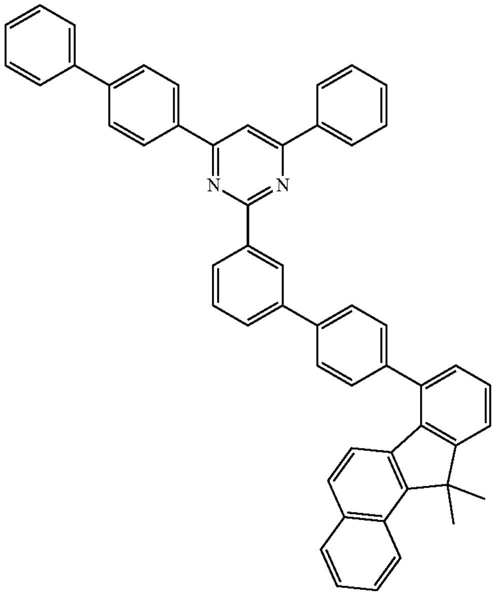
231
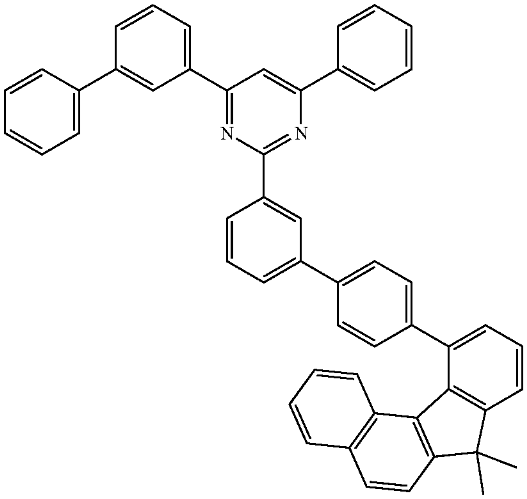
232
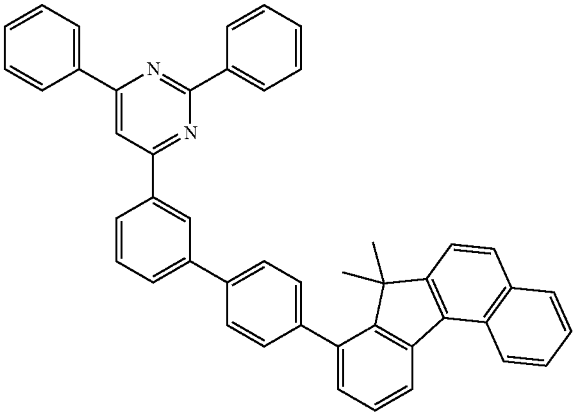
-continued
233
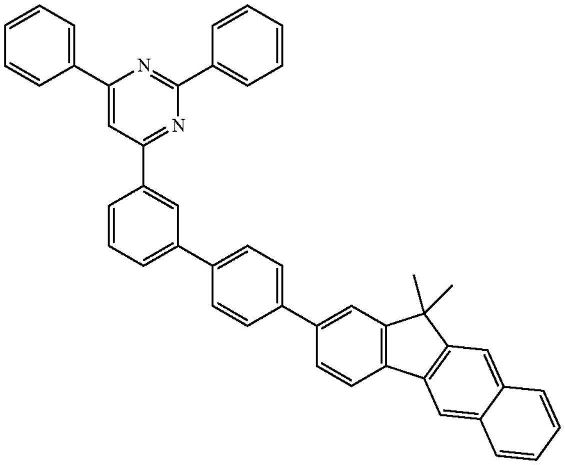
234
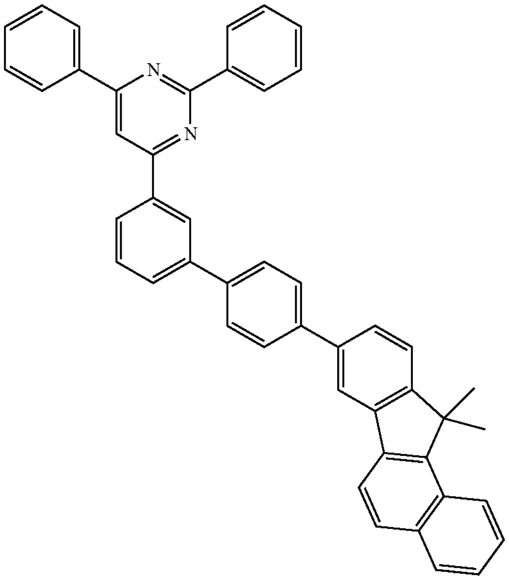
235
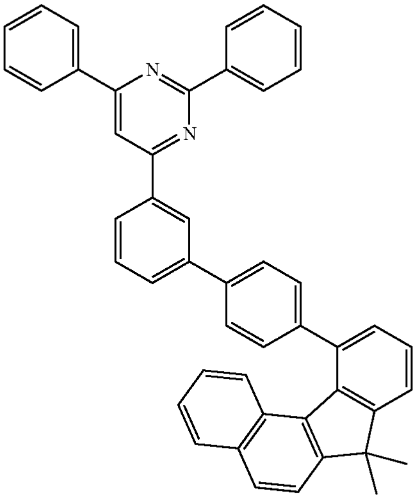

-continued
236
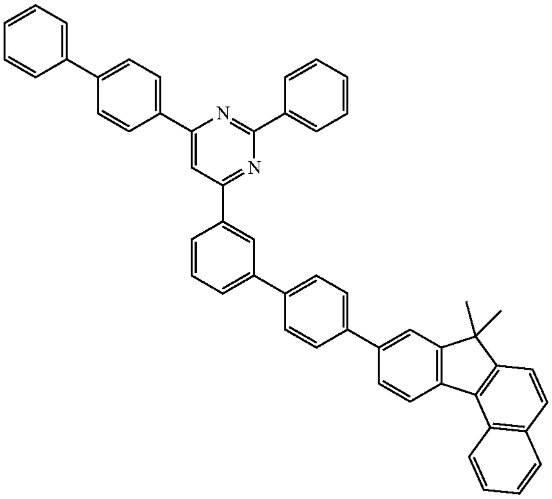
237
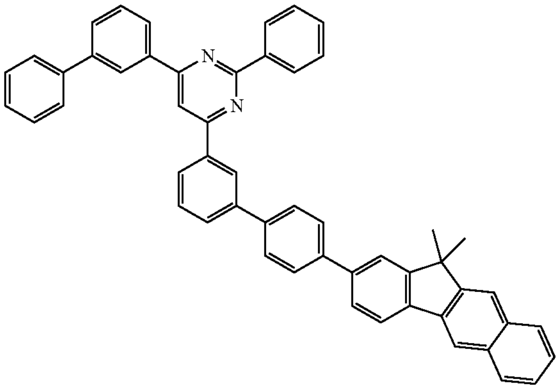
238
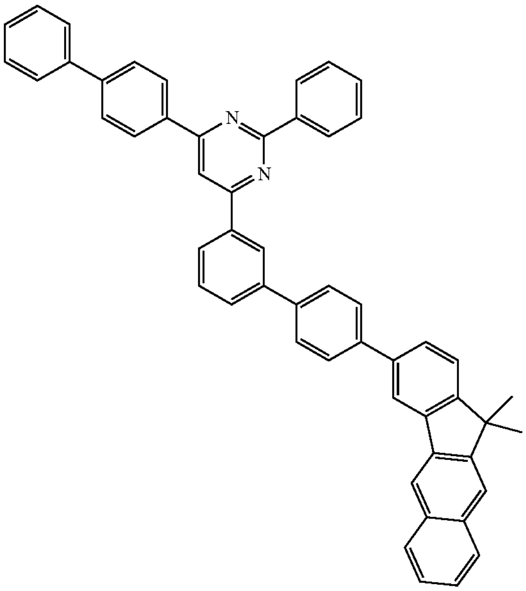
-continued
239
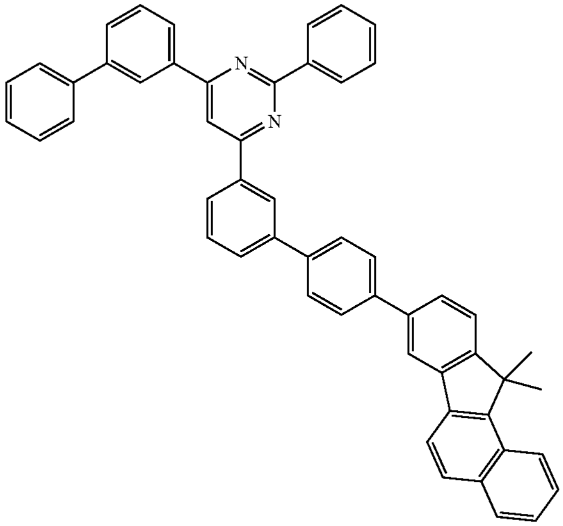
240
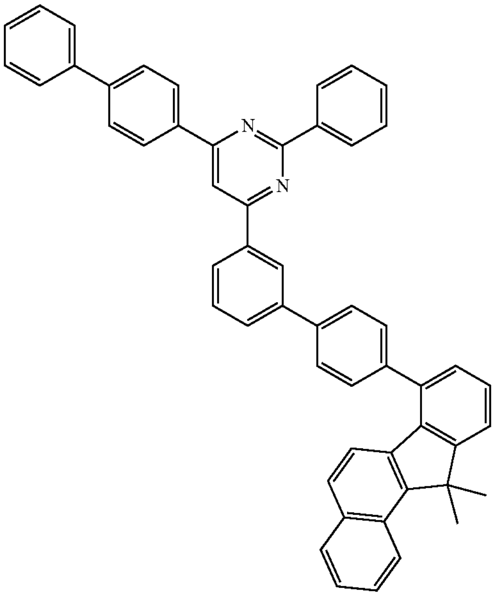
241
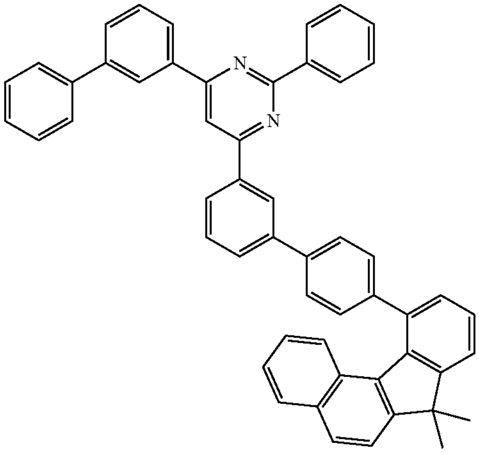

-continued
242
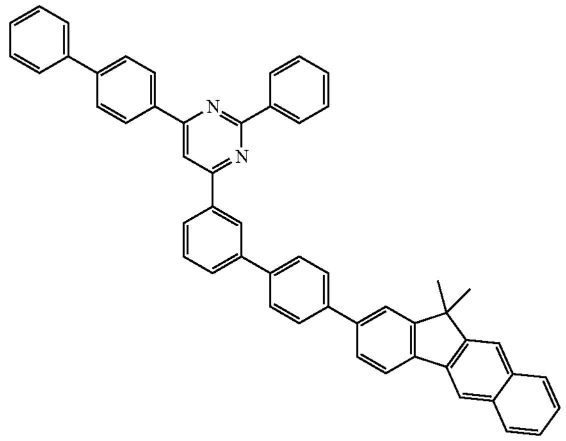
243
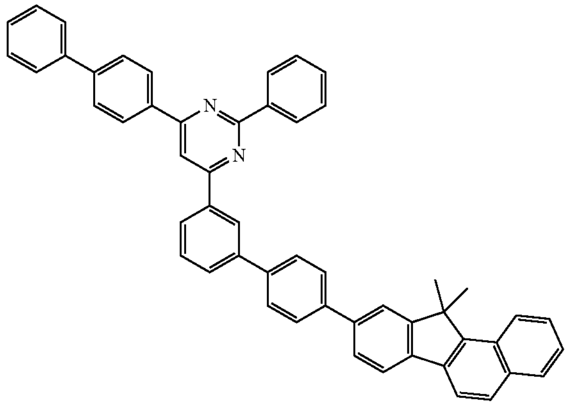
244
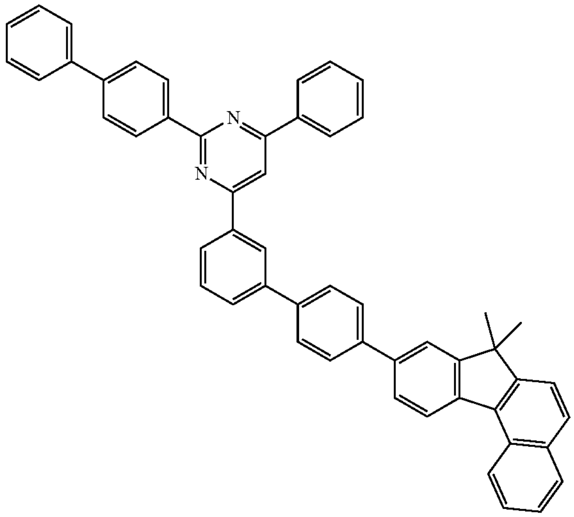
-continued
245
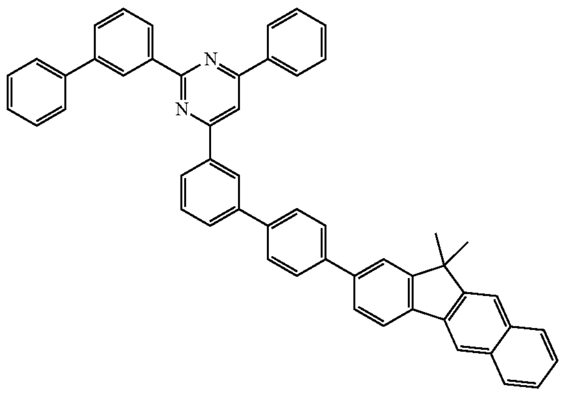
246
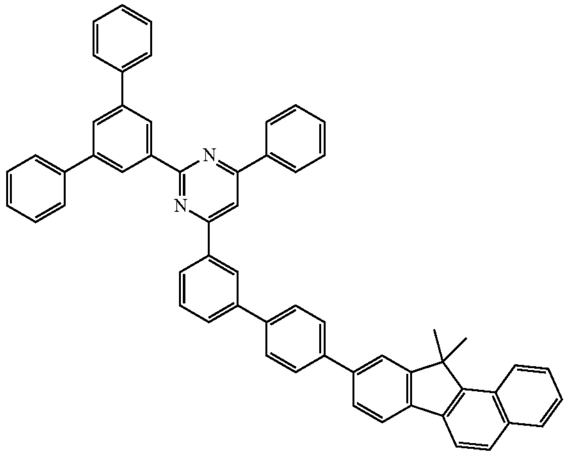
247
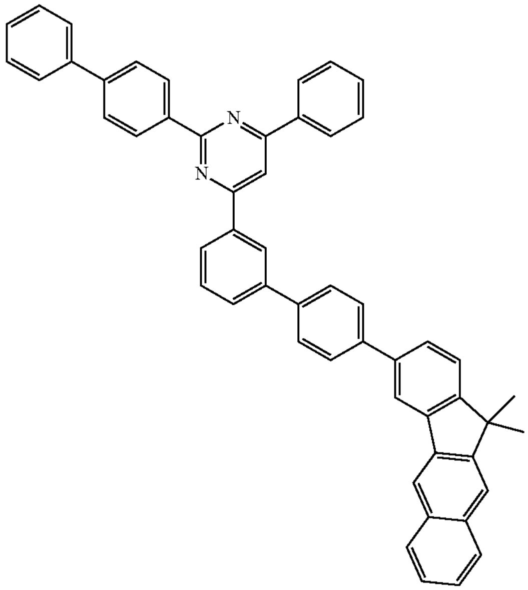

-continued

248

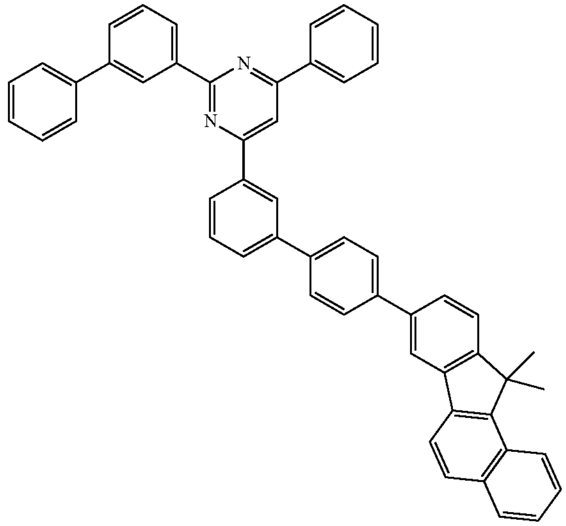

249

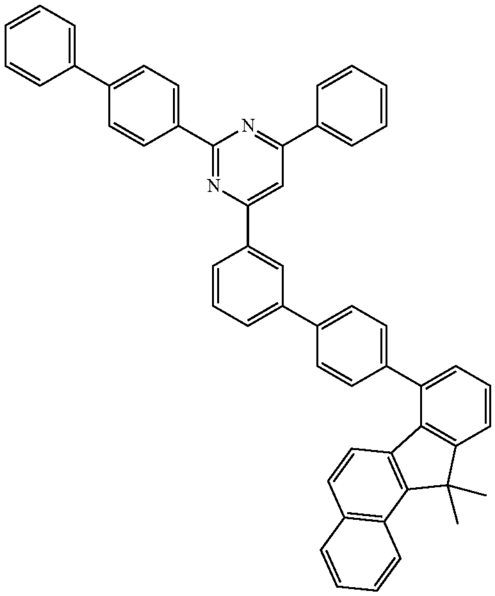

-continued

250

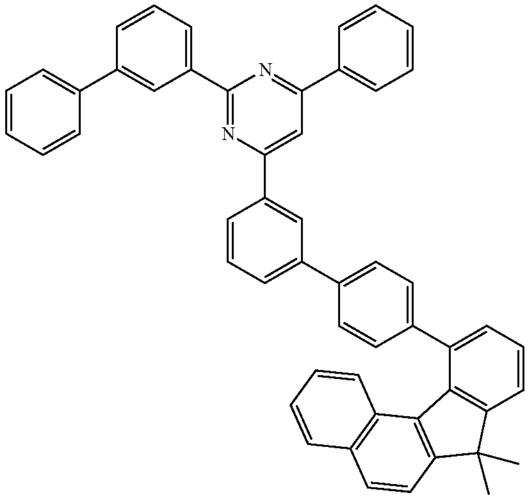

As used herein, "alkyl" refers to a monovalent substituent derived from a linear or branched chain saturated hydrocarbon having 1 to 40 carbon atoms. Examples of such alkyl may include, but are not limited to, methyl, ethyl, propyl, isobutyl, sec-butyl, pentyl, iso-amyl, hexyl or the like.

As used herein, "alkenyl" refers to a monovalent substituent derived from a linear or branched chain unsaturated hydrocarbon having 2 to 40 carbon atoms, having at least one carbon-carbon double bond. Examples of such alkenyl may include, but are not limited to, vinyl, allyl, isopropenyl, 2-butenyl or the like.

As used herein, "alkynyl" refers to a monovalent substituent derived from a linear or branched chain unsaturated hydrocarbon having 2 to 40 carbon atoms, having at least one carbon-carbon triple bond. Examples of such alkynyl may include, but are not limited to, ethynyl, 2-propynyl or the like.

As used herein, "cycloalkyl" refers to a monovalent substituent derived from a monocyclic or polycyclic non-aromatic hydrocarbon having 3 to 40 carbon atoms. Examples of such cycloalkyl may include, but are not limited to, cyclopropyl, cyclopentyl, cyclohexyl, norbornyl, adamantine or the like.

As used herein, "heterocycloalkyl" refers to a monovalent substituent derived from a non-aromatic hydrocarbon having 3 to 40 nuclear atoms, where one or more carbons in the ring, preferably one to three carbons, are substituted with a heteroatom such as N, O, S or Se. Examples of such heterocycloalkyl may include, but are not limited to, morpholine, piperazine or the like.

As used herein, "aryl" refers to a monovalent substituent derived from an aromatic hydrocarbon having 6 to 60 carbon atoms which is in a structure with a single ring or two or more rings combined with each other. In addition, a form in which two or more rings are pendant (e.g., simply attached) to or fused with each other may also be included. Examples of such aryl may include, but are not limited to, phenyl, naphthyl, phenanthryl, anthryl or the like.

As used herein, "heteroaryl" refers to a monovalent substituent derived from a monoheterocyclic or polyheterocyclic aromatic hydrocarbon having 5 to 60 nuclear atoms. In such an embodiment, one or more carbons in the ring, preferably one to three carbons, are substituted with a heteroatom such as N, O, S or Se. In addition, a form in which two or more rings are pendant to or fused with each other may be included and a form fused with an aryl group may be included. Examples of such heteroaryl may include, but are not limited to, a 6-membered monocyclic ring including, for example, pyridyl, pyrazinyl, pyrimidinyl, pyridazinyl and triazinyl; a polycyclic ring including, for example, phenoxathienyl, indolinzinyl, indolyl, purinyl, quinolyl, benzothiazole, and carbazolyl; 2-furanyl; N-imidazolyl; 2-isoxazolyl; 2-pyridinyl; 2-pyrimidinyl or the like.

As used herein, "alkyloxy" refers to a monovalent substituent represented by R'O—, where R' refers to an alkyl having 1 to 40 carbon atoms, and such alkyloxy may include a linear, branched or cyclic structure. Examples of such alkyloxy may include, but are not limited to, methoxy, ethoxy, n-propoxy, 1-propoxy, t-butoxy, n-butoxy, pentoxy or the like.

As used herein, "aryloxy" refers to a monovalent substituent represented by RO—, where R refers to an aryl having 5 to 40 carbon atoms. Examples of such aryloxy may include, but are not limited to, phenyloxy, naphthyloxy, diphenyloxy or the like.

As used herein, "alkylsilyl" refers to a silyl substituted with an alkyl having 1 to 40 carbon atoms and includes mono- as well as di- and tri-alkylsilyl. In addition, "arylsilyl" refers to a silyl substituted with an aryl having 5 to 60 carbon atoms, and includes mono- as well as polyarylsilyl such as di- and tri-arylsilyl.

As used herein, "alkylboron group" refers to a boron group substituted with an alkyl having 1 to 40 carbon atoms, and "arylboron group" refers to a boron group substituted with an aryl having 6 to 60 carbon atoms.

As used herein, "alkylphosphinyl group" refers to a phosphine group substituted with an alkyl having 1 to 40 carbon atoms, and includes mono- as well as di-alkylphosphinyl group. In addition, as used herein, "arylphosphinyl group" refers to a phosphine group substituted with a monoaryl or diaryl having 6 to 60 carbon atoms, and includes mono- as well as di-arylphosphinyl group.

As used herein, "arylamine" refers to an amine substituted with an aryl having 6 to 40 carbon atoms, and includes mono- as well as di-arylamine.

As used herein, "fused ring (e.g., condensed ring)" refers to a fused aliphatic ring, a fused aromatic ring, a fused heteroaliphatic ring, a fused heteroaromatic ring, or a combination thereof.

<Organic Electroluminescent Device>

Another aspect of the present invention relates to an organic electroluminescent device (hereinafter, "organic EL device") including the compound represented by Chemical Formula 1 or 2.

Specifically, the organic EL device according to the present invention includes an anode (e.g., a positive electrode), a cathode (e.g., a negative electrode), and one or more organic layers disposed between the anode and the cathode, and at least one of the one or more organic layers includes the compound represented by Chemical Formula 1 or 2. In such an embodiment, the compound may be used solely or as a combination of two or more kinds thereof.

The one or more organic layers may include one or more of a hole injection layer, a hole transport layer, a light-emitting layer, an electron transport auxiliary layer, an electron transport layer, and an electron injection layer, and at least one of the organic layers may include the compound represented by Chemical Formula 1 or 2. Specifically, the organic layer including the compound represented by Chemical Formula 1 or 2 may be selected from an electron transport layer and an electron transport auxiliary layer.

In an embodiment, the one or more organic layer may include a hole injection layer, a hole transport layer, a light-emitting layer, an electron transport layer, and an electron injection layer, and the electron transport layer includes the compound represented by Chemical Formula 1 or 2. In such a case, the compound represented by Chemical Formula 1 or 2 is included in the organic EL device as an electron transport layer material. In such an organic EL device, electrons may be easily injected from the cathode or the electron injection layer to the electron transport layer because of the compound of Chemical Formula 1 or 2, and may also rapidly move from the electron transport layer to the light-emitting layer, and thus holes and electrons in the light-emitting layer has a high bonding force. Accordingly, the organic EL device of the present invention is excellent in luminous efficiency, power efficiency, luminance, and the like. In addition, the compound of Chemical Formula 1 or 2 has excellent thermal stability and electrochemical stability, thereby improving the performance of the organic EL device.

Such a compound of Chemical Formula 1 or 2 may be used alone, or may be mixed with electron transport layer materials known in the art.

In the present invention, the electron transport layer material that may be mixed with the compound of Chemical Formula 1 or 2 may include an electron transport material commonly known in the art. Non-limiting examples of the applicable electron transport material may include an oxazole-based compound, an isoxazole-based compound, a triazole-based compound, an isothiazole-based compound, an oxadiazole-based compound, a thiadiazole-based compound, a perylene-based compound, an aluminum complex (e.g., $Alq_3$, tris(8-quinolinolato)-aluminium), and a gallium complex (e.g., Gaq'2OPiv, Gaq'2OAc, 2(Gaq'2)). These may be used alone or in combination of two or more.

In the present invention, when the compound of Chemical Formula 1 or 2 and the electron transport layer material are mixed, a mixing ratio thereof is not particularly limited and may be appropriately adjusted within a range known in the art.

According to another embodiment, the one or more organic layers may include a hole injection layer, a hole transport layer, a light-emitting layer, an electron transport auxiliary layer, an electron transport layer, and an electron injection layer, and the electron transport auxiliary layer may include the compound represented by Chemical Formula 1 or 2. In such a case, the compound represented by Chemical Formula 1 or 2 is included in the organic EL device as an electron transport auxiliary layer material. In such a case, the compound of Chemical Formula 1 or 2 has a high triplet energy. For this reason, when the compound of Chemical Formula 1 or 2 is included as an electron transport auxiliary layer material, efficiency of the organic EL device may be increased due to a triplet-triplet fusion (TTF) effect. In addition, the compound of Chemical Formula 1 or 2 may prevent excitons generated in the light-emitting layer from diffusing into the electron transport layer adjacent to the light-emitting layer. Accordingly, the number of excitons contributing to light emission in the light-emitting layer may be increased to improve luminous efficiency of the device, and durability and stability of the device may be improved to effectively increase the lifespan of the device.

Figure 2:
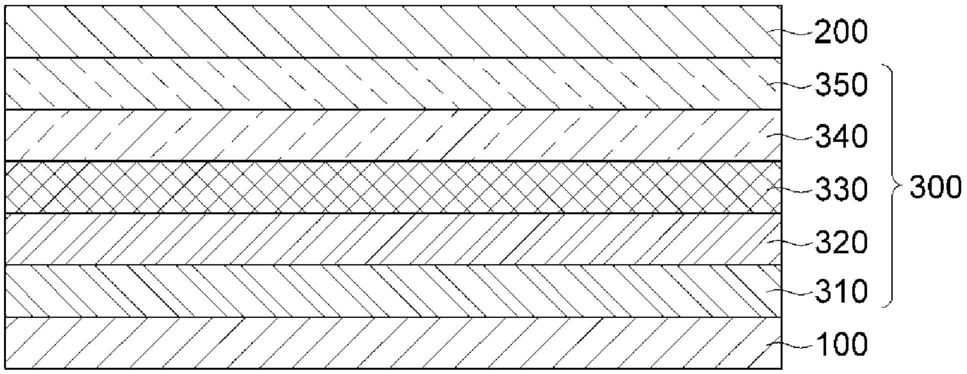
FIG. 2 is a cross-sectional view schematically illustrating an organic EL device according to a second embodiment of the present invention.
Figure 3:
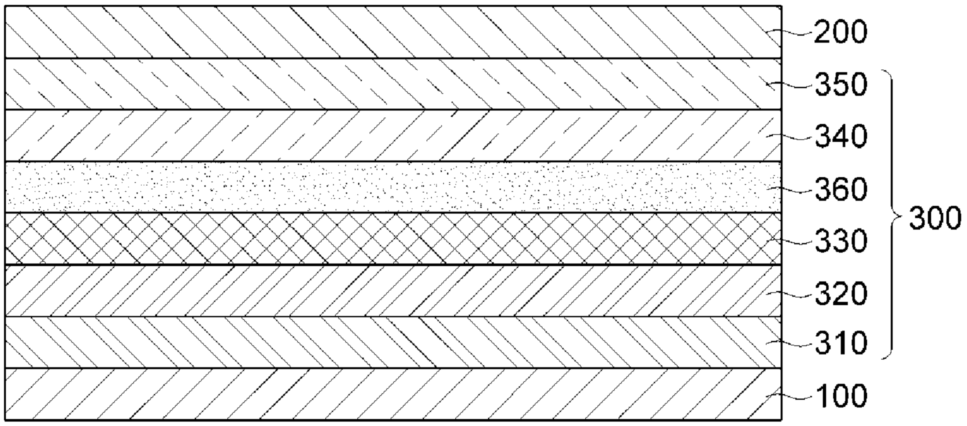
FIG. 3 is a cross-sectional view schematically illustrating an organic EL device according to a third embodiment of the present invention.

The structure of the organic EL device of the present invention described above is not particularly limited, and may include, for example, an anode 100, one or more organic layers 300 and a cathode 200 sequentially stacked on a substrate (see FIGS. 1 to 3). In addition, although not illustrated, it may have a structure in which an insulating layer or an adhesive layer is inserted at an interface between the electrode and the organic layer.

According to an embodiment, as illustrated in FIG. 1, the organic EL device may have a structure including, on a substrate, an anode 100, a hole injection layer 310, a hole transport layer 320, a light-emitting layer 330, an electron transport layer 340 and a cathode 200 sequentially stacked. Optionally, as illustrated in FIG. 2, an electron injection layer 350 may be positioned between the electron transport layer 340 and the cathode 200. In addition, an electron transport auxiliary layer 360 may be positioned between the light-emitting layer 330 and the electron transport layer 340 (see FIG. 3).

The organic EL device of the present invention may be manufactured by forming an organic layer and an electrode with materials and methods known in the art, except that at least one of the organic layer 300 (e.g., the electron transport layer 340, the electron transport auxiliary layer 360) includes the compound represented by Chemical Formula 1 or 2.

The organic layer may be formed by a vacuum deposition method or a solution coating method. Examples of the solution coating method include, but are not limited to, spin coating, dip coating, doctor blading, inkjet printing, or thermal transfer method.

The substrate applicable in the present invention is not particularly limited, and non-limiting examples thereof may include a silicon wafer, quartz, a glass plate, a metal plate, a plastic film, and a sheet.

In addition, examples of the anode material may include, but are not limited to, metals such as vanadium, chromium, copper, zinc, and gold or an alloy thereof; metal oxides such as zinc oxide, indium oxide, indium tin oxide (ITO), or indium zinc oxide (IZO); combination of oxide with metal such as ZnO:Al or $SnO_2$:Sb; conductive polymers such as polythiophene, poly(3-methylthiophene), poly [3,4-(ethylene-1,2-dioxy) thiophene] (PEDT), polypyrrole or polyaniline; and carbon black or the like.

Examples of the cathode material may include, but are not limited to, metals such as magnesium, calcium, sodium, potassium, titanium, indium, yttrium, lithium, gadolinium, aluminum, silver, tin, or lead or an alloy thereof; a multi-layered material such as LiF/Al or $LiO_2$/Al or the like.

Hereinafter, the present invention will be described in detail through examples. However, the following examples only provided to illustrate the present invention, and the present invention is not limited by the following examples.

[Preparation Example 1] Synthesis of Py-1

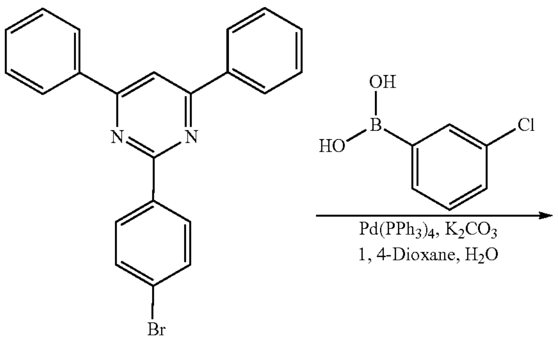

-continued

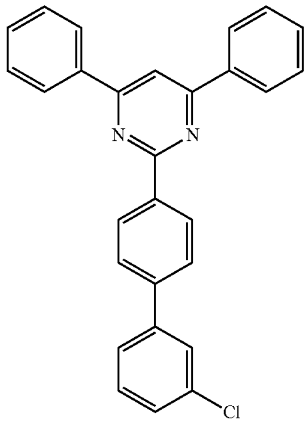

Py-1

15.0 g of 2-(4-bromophenyl)-4,6-diphenylpyrimidine, 6.0 g of (3-chlorophenyl)boronic acid, 0.9 g of tetrakisphenylphosphine palladium (0) and 7.0 g of $K_2CO_3$ were added into 350 ml of toluene, 60 ml of ethanol, and 60 ml of water, and the mixture was heated and stirred under reflux for 2 hours. After completion of the reaction, followed by inactivation with a sufficient amount of water, the solution was transferred to a separatory funnel, an organic layer was extracted with methylene chloride, the organic layer was dried over magnesium sulfate, concentrated, and purified by column chromatography, and thus Py-1 (10.8 g, yield 55%) was obtained.

1H-NMR: 8.23 (s, 1H), 7.95-7.93 (m, 7H), 7.55-7.40 (m, 9H), 7.25 (d, 2H).

Mass: $[(M+H)^+]$: 419.

[Preparation Example 2] Synthesis of Py-2

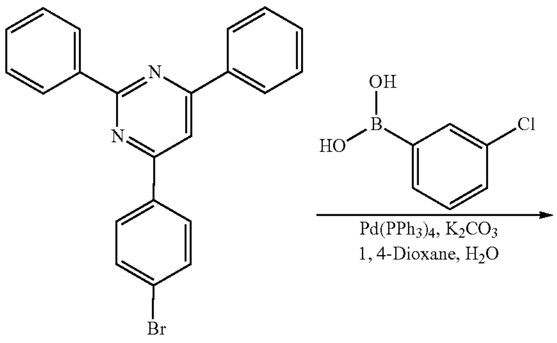

-continued

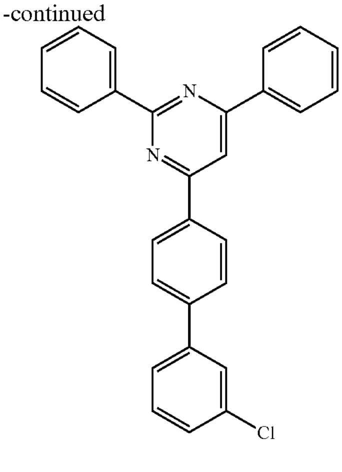

Py-2

Py-2 (8.5 g, yield 58%) was prepared in the same manner as in Preparation Example 1, except that 4-(4-bromophenyl)-2,6-diphenylpyrimidine was used instead of 2-(4-bromophenyl)-4,6-diphenylpyrimidine used in Preparation Example 1.

1H-NMR: 8.35 (d, 2H), 8.30 (d, 2H), 7.97-7.94 (m, 3H), 7.85 (d, 2H), 7.55-7.48 (m, 9H).

Mass: [(M+H)+]: 419.

[Preparation Example 3] Synthesis of Py-3

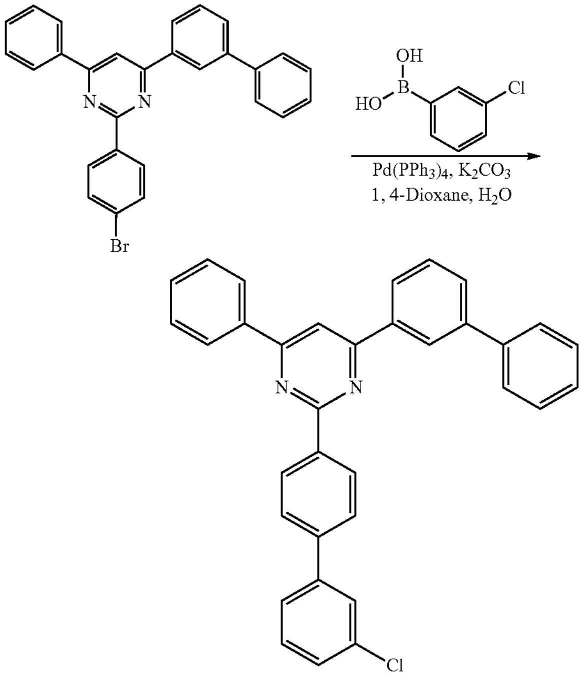

Py-3

Py-3 (9.8 g, yield 56%) was prepared in the same manner as in Preparation Example 1, except that 4-([1,1'-biphenyl]-3-yl)-2-(4-bromophenyl)-6-phenylpyrimidine was used instead of 2-(4-bromophenyl)-4,6-diphenylpyrimidine used in Preparation Example 1.

1H-NMR: 8.23 (s, 1H), 8.00-7.94 (m, 7H), 7.75-7.72 (m, 3H), 7.55-7.38 (m, 11H), 7.25 (d, 2H).

Mass: [(M+H)+]: 464.

[Preparation Example 4] Synthesis of Py-4

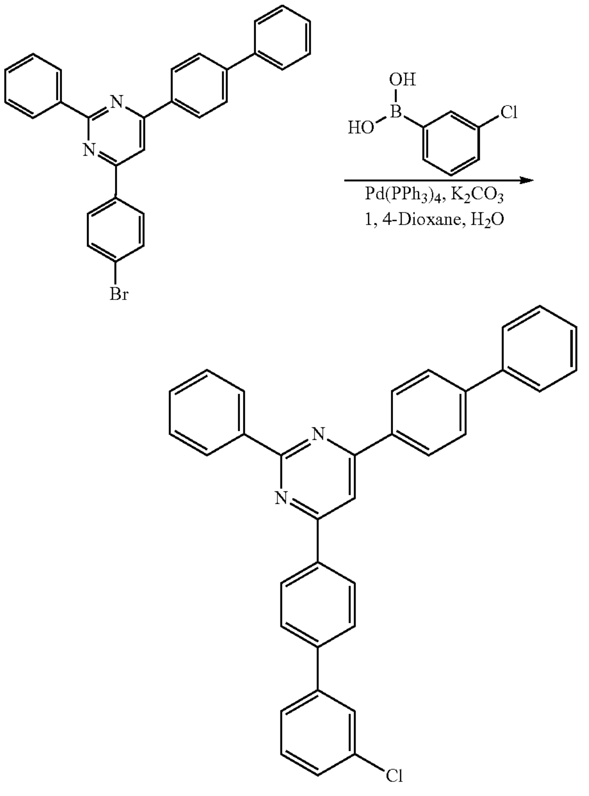

Py-4

Py-4 (9.2 g, yield 55%) was prepared in the same manner as in Preparation Example 1, except that 4-([1,1'-biphenyl]-4-yl)-6-(4-bromophenyl)-2-phenylpyrimidine was used instead of 2-(4-bromophenyl)-4,6-diphenylpyrimidine used in Preparation Example 1.

1H-NMR: 8.35-8.30 (m, 6H), 7.97 (s, 1H), 7.85 (d, 4H), 7.75 (d, 2H), 7.50-7.38 (m, 9H).

Mass: [(M+H)+]: 464.

[Preparation Example 5] Synthesis of Py-5

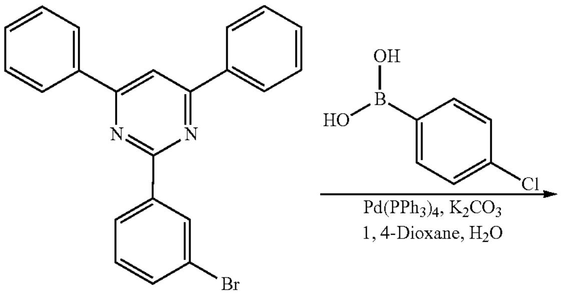

-continued

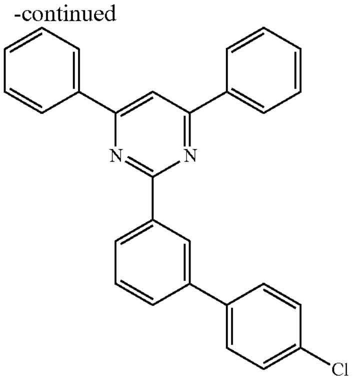

Py-5

15.0 g of 2-(3-bromophenyl)-4,6-diphenylpyrimidine, 6.0 g of (4-chlorophenyl)boronic acid, 0.9 g of tetrakisphenylphosphine palladium (0) and 7.0 g of $K_2CO_3$ were added into 350 ml of toluene, 60 ml of ethanol, and 60 ml of water, and the mixture was heated and stirred under reflux for 2 hours. After completion of the reaction, followed by inactivation with a sufficient amount of water, the solution was transferred to a separatory funnel, an organic layer was extracted with methylene chloride, the organic layer was dried over magnesium sulfate, concentrated, and purified by column chromatography, and thus Py-5 (10.1 g, yield 54%) was obtained.

1H-NMR: 8.38 (d, 1H), 8.23 (s, 1H), 8.10 (d, 2H), 7.94-7.90 (m, 3H), 7.73 (t, 1H), 7.62-7.45 (m, 9H).

Mass: $[(M+H)^+]$: 419

[Preparation Example 6] Synthesis of Py-6

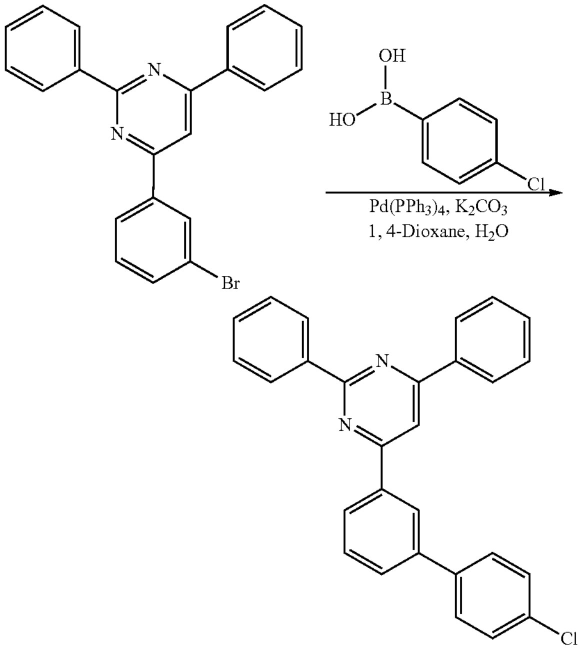

Py-6

Py-6 (9.6 g, yield 53%) was prepared in the same manner as in Preparation Example 5, except that 4-(3-bromophenyl)-2,6-diphenylpyrimidine was used instead of 2-(3-bromophenyl)-4,6-diphenylpyrimidine used in Preparation Example 5.

1H-NMR: 8.35 (d, 2H), 8.23 (s, 1H), 8.10 (d, 2H), 7.95 (d, 4H), 7.73 (s, 1H), 7.50-7.38 (m, 9H).

Mass: $[(M+H)^+]$: 419.

[Preparation Example 7] Synthesis of Py-7

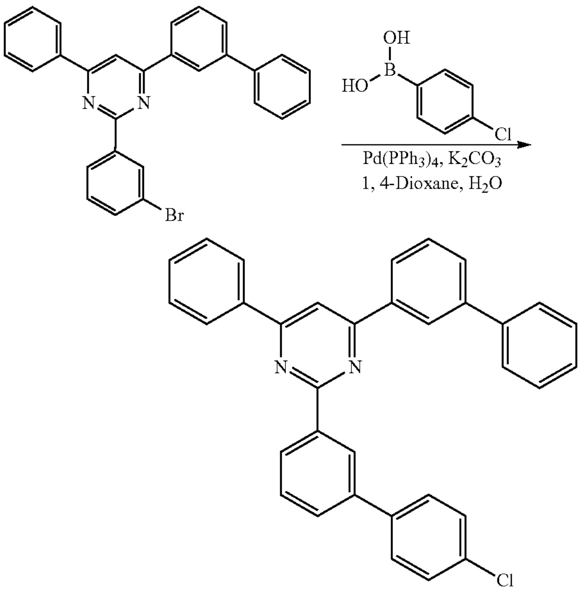

Py-7

Py-7 (9.8 g, yield 53%) was prepared in the same manner as in Preparation Example 5, except that 4-([1,1'-biphenyl]-3-yl)-2-(3-bromophenyl)-6-phenylpyrimidine was used instead of 2-(3-bromophenyl)-4,6-diphenylpyrimidine used in Preparation Example 5.

1H-NMR: 8.38 (d, 1H), 8.23 (s, 1H), 8.10 (d, 2H), 7.96-7.94 (m, 5H), 7.75-7.73 (m, 4H), 7.62-7.32 (m, 10H).

Mass: $[(M+H)^+]$: 496.

[Preparation Example 8] Synthesis of Py-8

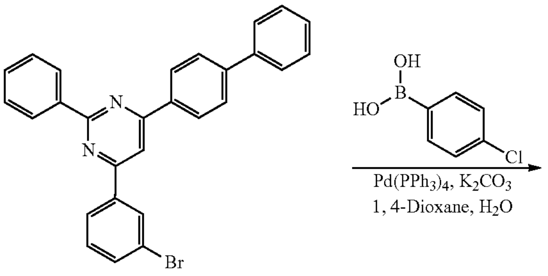

-continued

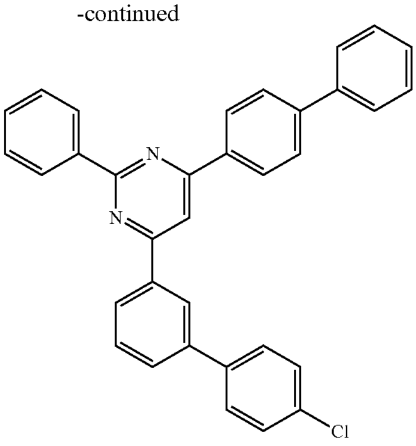

Py-8

Py-8 (9.2 g, yield 52%) was prepared in the same manner as in Preparation Example 5, except that 4-([1,1'-biphenyl]-4-yl)-6-(3-bromophenyl)-2-phenylpyrimidine was used instead of 2-(3-bromophenyl)-4,6-diphenylpyrimidine used in Preparation Example 5.

1H-NMR: 8.35 (d, 2H), 8.30 (d, 2H), 8.23 (s, 1H), 8.10 (d, 2H), 7.94 (m, 2H), 7.85 (d, 2H), 7.75-7.73 (m, 3H), 7.62-7.38 (m, 9H).

Mass: $[(M+H)^+]$: 496.

[Synthesis Example 1] Synthesis of Compound 3

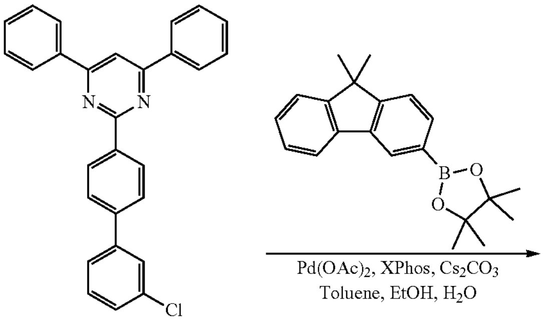

Py-1

-continued

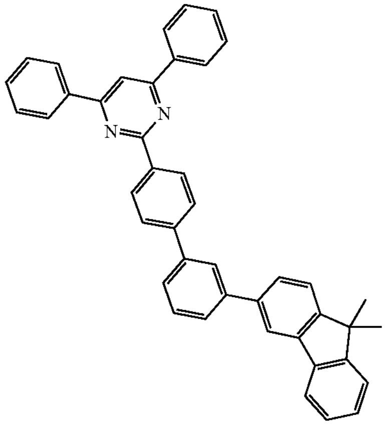

3

3.0 g of Py-1 synthesized in Preparation Example 1, 2.8 g of 2-(9,9-dimethyl-9H-fluoren-3-yl)-4,4,5,5-tetramethyl-1,3,2-dioxaborolan, and 3.0 g of $Cs_2CO_3$ were mixed, 60 ml of toluene, 12 ml of ethanol, and 12 ml of water were added thereto, and 55 mg of $Pd(OAc)_2$ and 250 mg of Xphos were further added thereto, and the mixture was heated and stirred for 4 hours. After the reaction was completed, the temperature was lowered to room temperature and then filtered. A filtrate was poured into water, an organic layer was extracted with methylene chloride, and the organic layer was dried over $MgSO_4$. The dried organic layer was concentrated under reduced pressure and then columned with THF: Hex=1:3, and thus Compound 3 (2.2 g, yield: 54%) was prepared.

Mass: $[(M+H)^+]$: 578.

[Synthesis Example 2] Synthesis of Compound 12

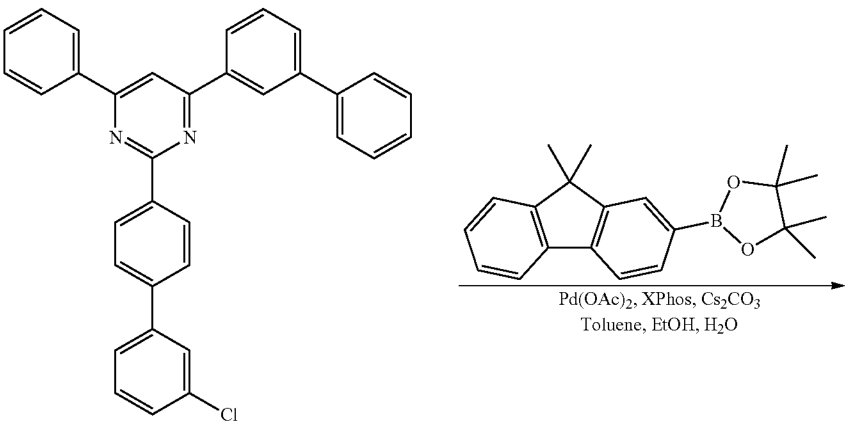

Py-3

-continued

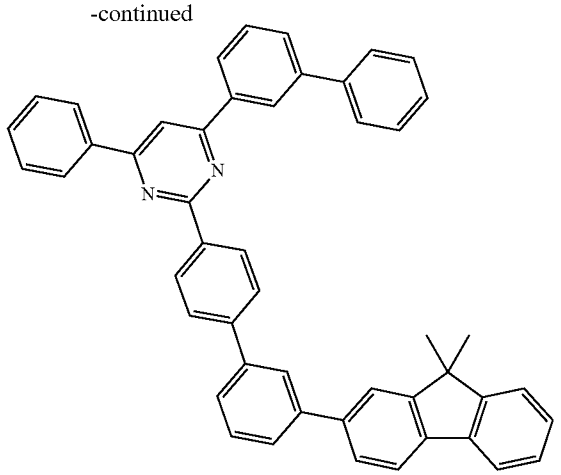

12

3.0 g of Py-3 synthesized in Preparation Example 3, 2.8 g of 2-(9,9-dimethyl-9H-fluoren-2-yl)-4,4,5,5-tetramethyl-1,3,2-dioxaborolan, and 3.0 g of $Cs_2CO_3$ were mixed, 60 ml of toluene, 12 ml of ethanol, and 12 ml of water were added thereto, and 55 mg of $Pd(OAc)_2$ and 250 mg of Xphos were further added thereto, and the mixture was heated and stirred for 4 hours. After the reaction was completed, the temperature was lowered to room temperature and then filtered. A filtrate was poured into water, an organic layer was extracted with methylene chloride, and the organic layer was dried over $MgSO_4$. The dried organic layer was concentrated under reduced pressure and then columned with MC:Hex=1:2, and thus Compound 12 (2.5 g, yield: 55%) was prepared.

Mass: $[(M+H)^+]$: 654.

[Synthesis Example 3] Synthesis of Compound 29

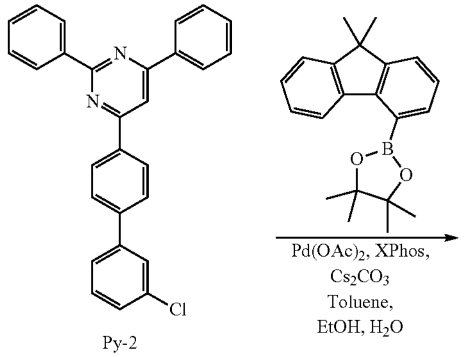

Py-2

-continued

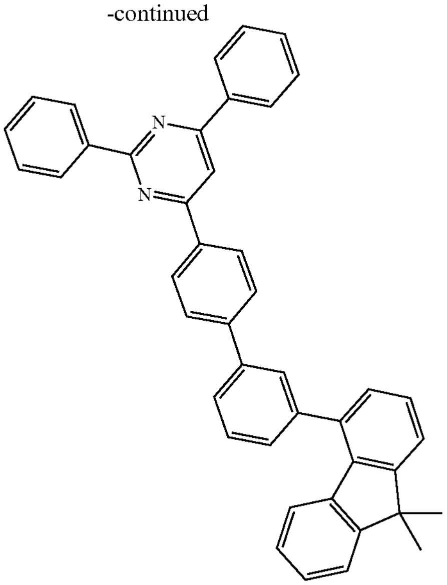

29

3.0 g of Py-2 synthesized in Preparation Example 2, 2.8 g of 2-(9,9-dimethyl-9H-fluoren-4-yl)-4,4,5,5-tetramethyl-1,3,2-dioxaborolan, and 3.0 g of $Cs_2CO_3$ were mixed, 60 ml of toluene, 12 ml of ethanol, and 12 ml of water were added thereto, and 55 mg of $Pd(OAc)_2$ and 250 mg of Xphos were further added thereto, and the mixture was heated and stirred for 4 hours. After the reaction was completed, the temperature was lowered to room temperature and then filtered. A filtrate was poured into water, an organic layer was extracted with methylene chloride, and the organic layer was dried over $MgSO_4$. The dried organic layer was concentrated under reduced pressure and then columned with MC:Hex=1:2, and thus Compound 29 (2.3 g, yield: 54%) was prepared.

Mass: $[(M+H)^+]$: 654.

[Synthesis Example 4] Synthesis of Compound 36

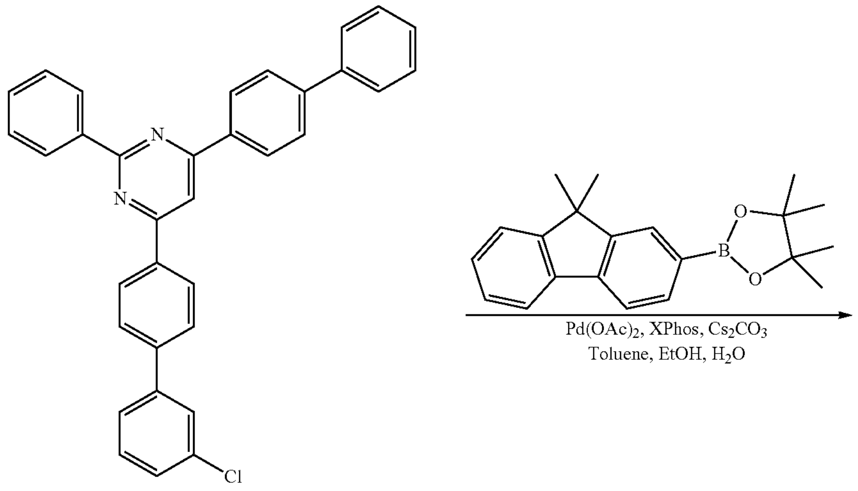

Py-4

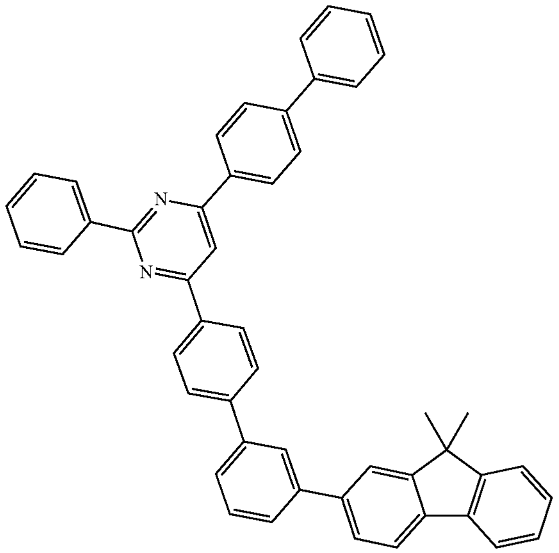

36

3.0 g of Py-4 synthesized in Preparation Example 4, 3.0 g of 2-(9,9-dimethyl-9H-fluoren-2-yl)-4,4,5,5-tetramethyl-1,3,2-dioxaborolan, and 3.0 g of $Cs_2CO_3$ were mixed, 60 ml of toluene, 12 ml of ethanol, and 12 ml of water were added thereto, and 55 mg of $Pd(OAc)_2$ and 250 mg of Xphos were further added thereto, and the mixture was heated and stirred for 4 hours. After the reaction was completed, the temperature was lowered to room temperature and then filtered. A filtrate was poured into water, an organic layer was extracted with methylene chloride, and the organic layer was dried over $MgSO_4$. The dried organic layer was concentrated under reduced pressure and then columned with MC:Hex=1:2, and thus Compound 36 (2.2 g, yield: 53%) was prepared.

Mass: $[(M+H)^+]$: 654.

[Synthesis Example 5] Synthesis of Compound 62
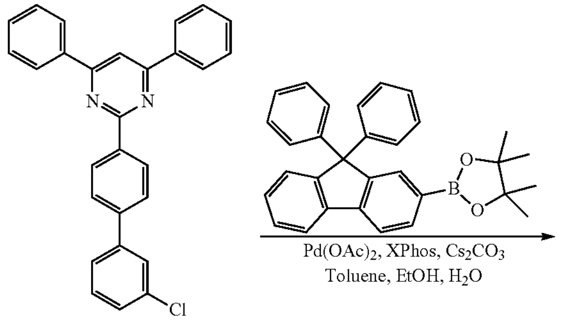
Py-1
-continued
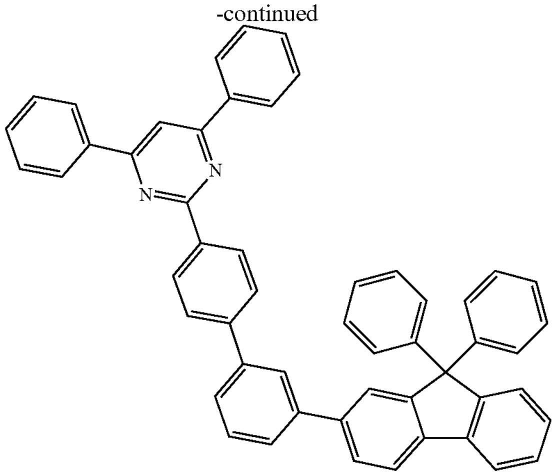
62
Compound 62 (2.1 g, yield: 55%) was prepared in the same manner as in Synthesis Example 1, except that 2-(9,9-diphenyl-9H-fluoren-2-yl)-4,4,5,5-tetramethyl-1,3,2-dioxaborolan was used instead of 2-(9,9-dimethyl-9H-fluoren-3-yl)-4,4,5,5-tetramethyl-1,3,2-dioxaborolan used in Synthesis Example 1.
Mass: $[(M+H)^+]$: 578.
[Synthesis Example 6] Synthesis of Compound 66
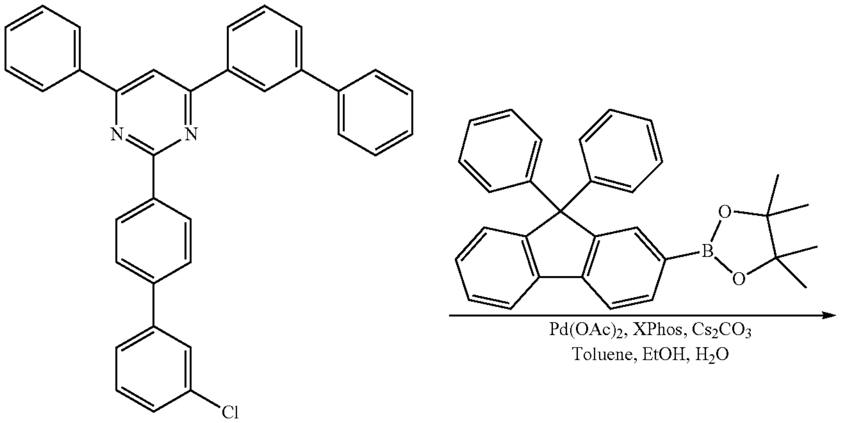
Py-3

-continued

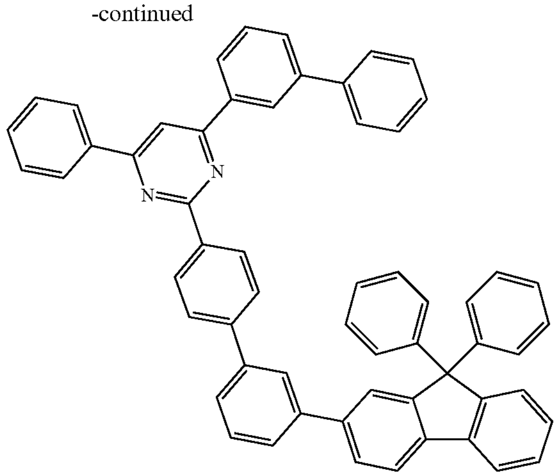

66

Compound 66 (2.3 g, yield: 55%) was prepared in the same manner as in Synthesis Example 2, except that 2-(9,9-diphenyl-9H-fluoren-2-yl)-4,4,5,5-tetramethyl-1,3,2-dioxaborolan was used instead of 2-(9,9-dimethyl-9H-fluoren-2-yl)-4,4,5,5-tetramethyl-1,3,2-dioxaborolan used in Synthesis Example 2.

Mass: $[(M+H)^+]$: 778.

[Synthesis Example 7] Synthesis of Compound 76

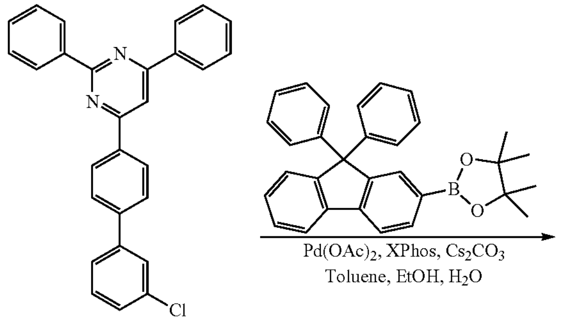

Py-2

-continued

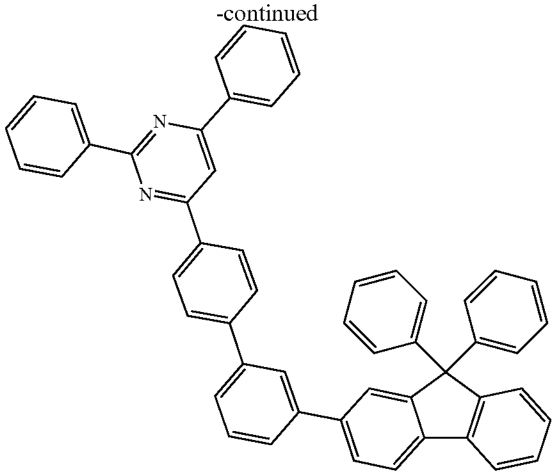

76

Compound 76 (2.0 g, yield: 53%) was prepared in the same manner as in Synthesis Example 3, except that 2-(9,9-diphenyl-9H-fluoren-2-yl)-4,4,5,5-tetramethyl-1,3,2-dioxaborolan was used instead of 2-(9,9-dimethyl-9H-fluoren-4-yl)-4,4,5,5-tetramethyl-1,3,2-dioxaborolan used in Synthesis Example 3.

Mass: $[(M+H)^+]$: 702.

[Synthesis Example 8] Synthesis of Compound 81
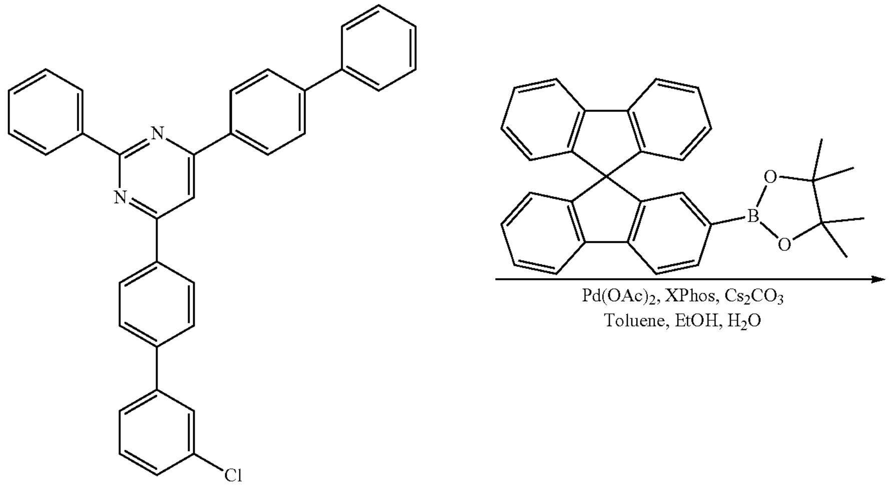
Py-4
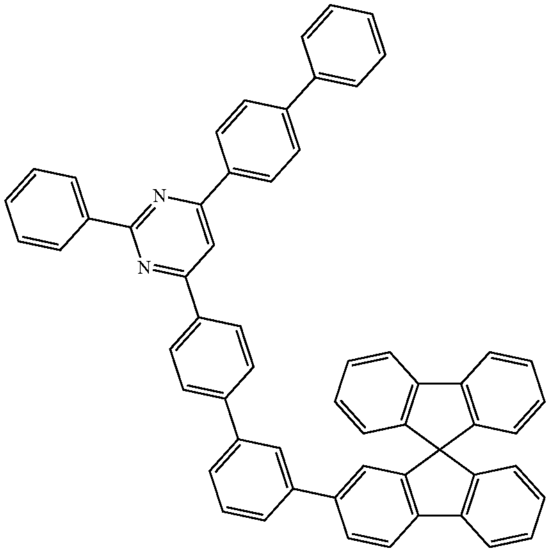
81
Compound 81 (2.0 g, yield: 52%) was prepared in the same manner as in Synthesis Example 4, except that 2-(9,9'-spirobi[fluoren]-2-yl)-4,4,5,5-tetramethyl-1,3,2-dioxaborolan was used instead of 2-(9,9-dimethyl-9H-fluoren-2-yl)-4,4,5,5-tetramethyl-1,3,2-dioxaborolan used in Synthesis Example 4.
Mass: $[(M+H)^+]$: 776.

[Synthesis Example 9] Synthesis of Compound 102
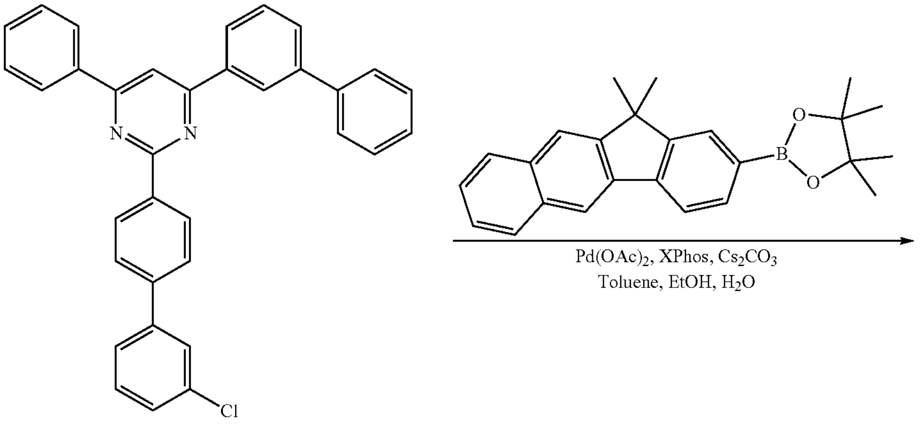
Py-3
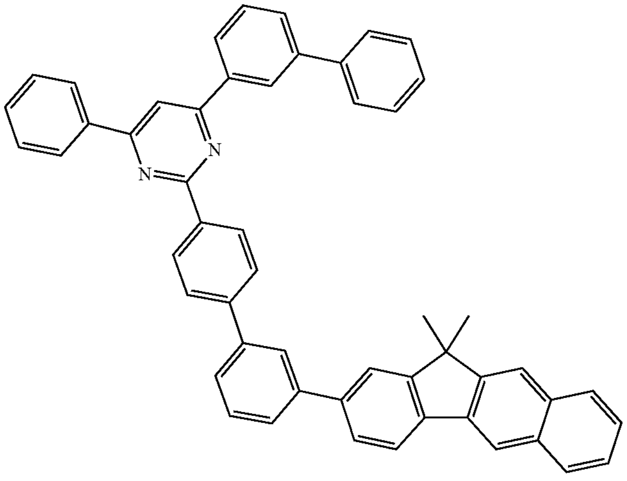
102
Compound 102 (2.5 g, yield: 53%) was prepared in the same manner as in Synthesis Example 2, except that 2-(11,11-dimethyl-11H-benzo[b]fluoren-2-yl)-4,4,5,5-tetramethyl-1,3,2-dioxaborolan was used instead of 2-(9,9-dimethyl-9H-fluoren-2-yl)-4,4,5,5-tetramethyl-1,3,2-dioxaborolan used in Synthesis Example 2.
Mass: $[(M+H)^+]$: 704.

[Synthesis Example 10] Synthesis of Compound 110
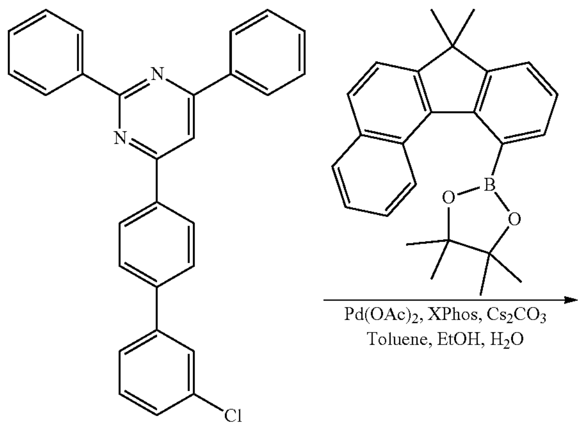
Py-2
-continued
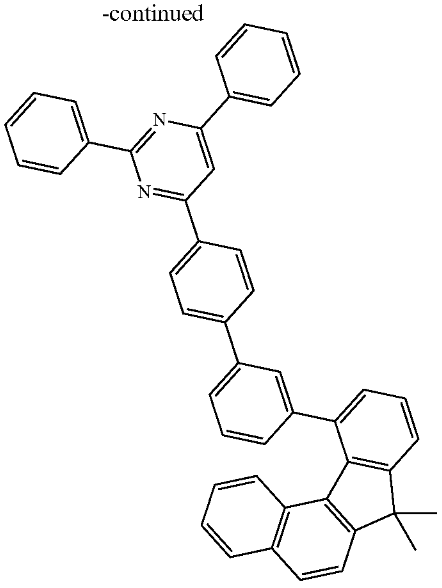
110
Compound 110 (2.2 g, yield: 52%) was prepared in the same manner as in Synthesis Example 3, except that 2-(7,7-dimethyl-7H-benzo[c]fluoren-11-yl)-4,4,5,5-tetramethyl-1,3,2-dioxaborolan was used instead of 2-(9,9-dimethyl-9H-fluoren-4-yl)-4,4,5,5-tetramethyl-1,3,2-dioxaborolan used in Synthesis Example 3.
Mass: $[(M+H)^+]$: 628.
[Synthesis Example 11] Synthesis of Compound 111
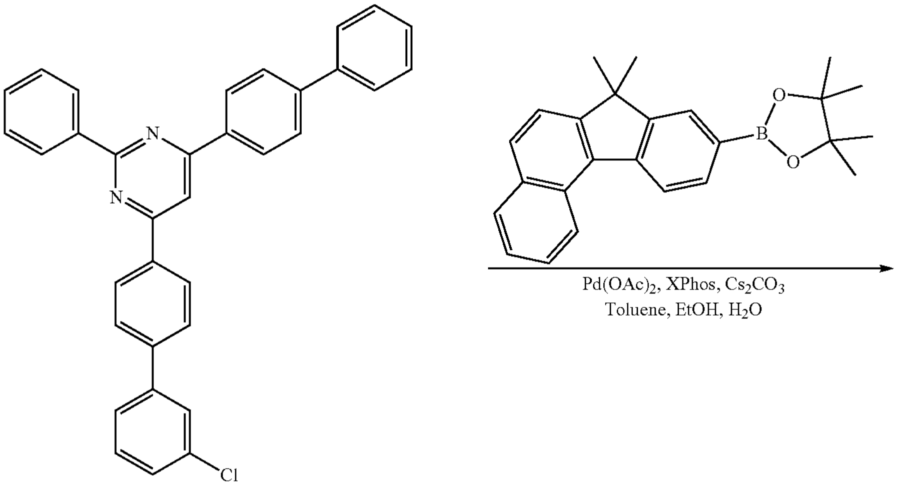
Py-4

-continued

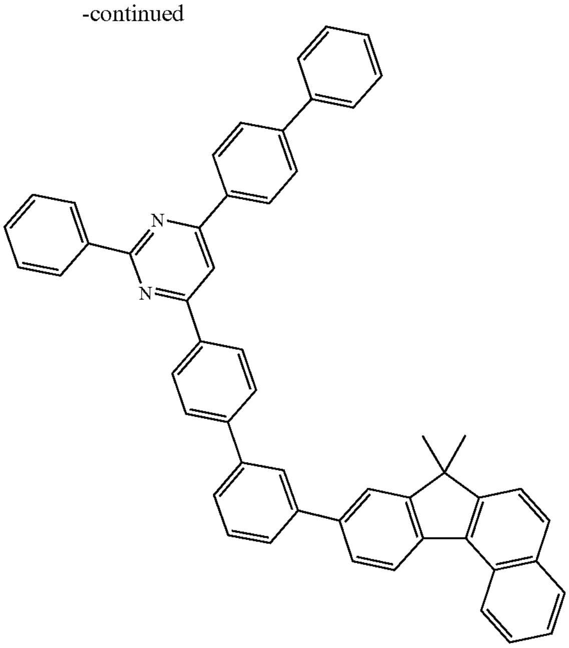

111

Compound 111 (2.1 g, yield: 52%) was prepared in the same manner as in Synthesis Example 4, except that 2-(7,7-dimethyl-7H-benzo[c]fluoren-9-yl)-4,4,5,5-tetramethyl-1,3,2-dioxaborolan was used instead of 2-(9,9-dimethyl-9H-fluoren-2-yl)-4,4,5,5-tetramethyl-1,3,2-dioxaborolan used in Synthesis Example 4.

Mass: $[(M+H)^+]$: 704.

[Synthesis Example 12] Synthesis of Compound 129

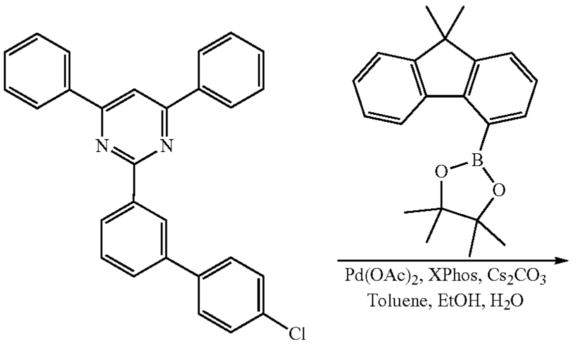

Py-5

-continued

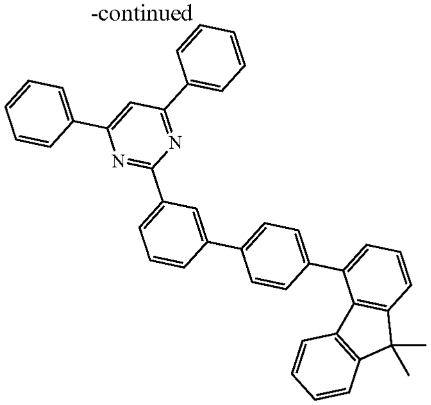

129

3.0 g of Py-5 synthesized in Preparation Example 5, 2.8 g of 2-(9,9-dimethyl-9H-fluoren-4-yl)-4,4,5,5-tetramethyl-1,3,2-dioxaborolan, and 3.0 g of $Cs_2CO_3$ were mixed, 60 ml of toluene, 12 ml of ethanol, and 12 ml of water were added thereto, and 55 mg of $Pd(OAc)_2$ and 250 mg of Xphos were further added thereto, and the mixture was heated and stirred for 4 hours. After the reaction was completed, the temperature was lowered to room temperature and then filtered. A filtrate was poured into water, an organic layer was extracted with methylene chloride, and the organic layer was dried over $MgSO_4$. The dried organic layer was concentrated under reduced pressure and then columned with THF: Hex=1:3, and thus Compound 129 (2.1 g, yield: 54%) was prepared.

Mass: $[(M+H)^+]$: 578.

[Synthesis Example 13] Synthesis of Compound 131

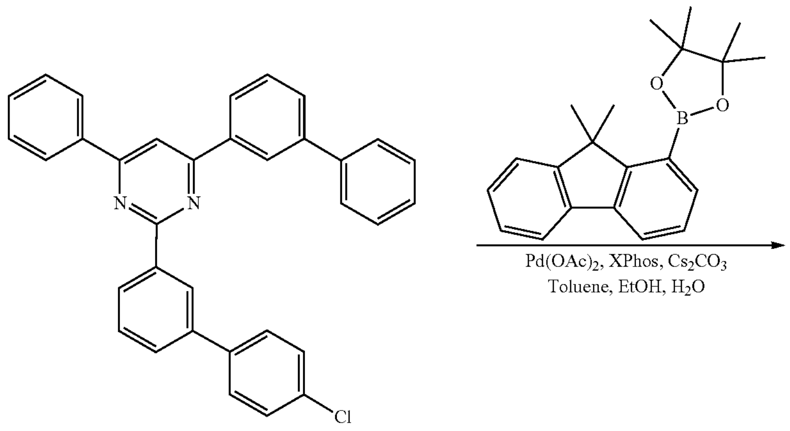

Py-7

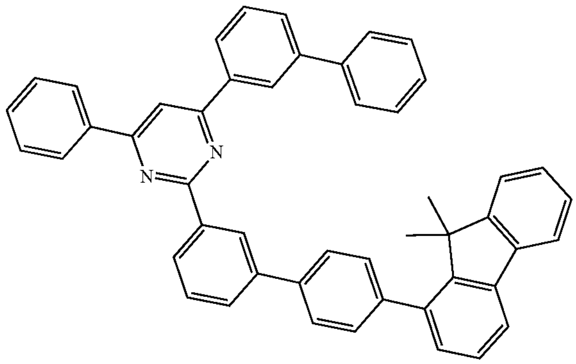

131

3.0 g of Py-7 synthesized in Preparation Example 7, 2.8 g of 2-(9,9-dimethyl-9H-fluoren-1-yl)-4,4,5,5-tetramethyl-1,3,2-dioxaborolan, and 3.0 g of $Cs_2CO_3$ were mixed, 60 ml of toluene, 12 ml of ethanol, and 12 ml of water were added thereto, and 55 mg of $Pd(OAc)_2$ and 250 mg of Xphos were further added thereto, and the mixture was heated and stirred for 4 hours. After the reaction was completed, the temperature was lowered to room temperature and then filtered. A filtrate was poured into water, an organic layer was extracted with methylene chloride, and the organic layer was dried over $MgSO_4$. The dried organic layer was concentrated under reduced pressure and then columned with EA:Hex=1:5, and thus Compound 131 (1.9 g, yield: 49%) was prepared.

Mass: $[(M+H)^+]$: 654.

[Synthesis Example 14] Synthesis of Compound 153

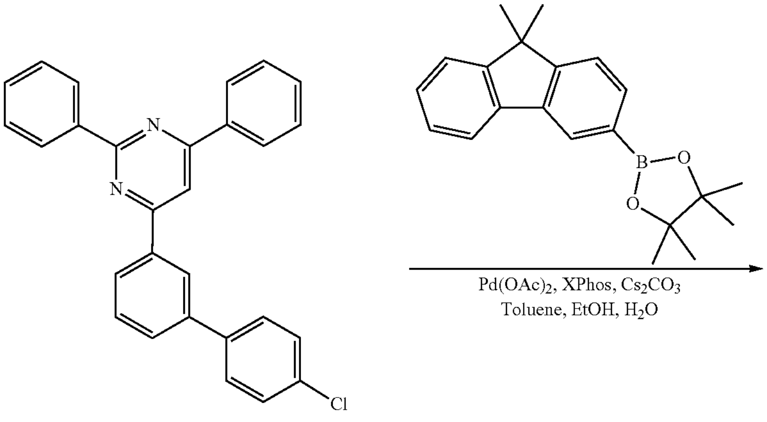

Py-6

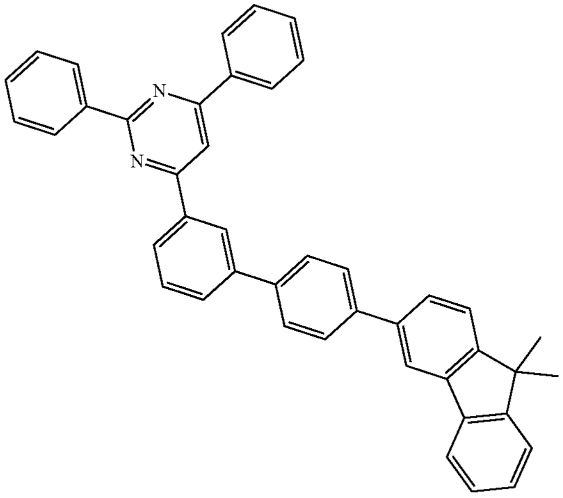

153

3.0 g of Py-6 synthesized in Preparation Example 6, 2.8 g of 2-(9,9-dimethyl-9H-fluoren-3-yl)-4,4,5,5-tetramethyl-1,3,2-dioxaborolan, and 3.0 g of $Cs_2CO_3$ were mixed, 60 ml of toluene, 12 ml of ethanol, and 12 ml of water were added thereto, and 55 mg of $Pd(OAc)_2$ and 250 mg of Xphos were further added thereto, and the mixture was heated and stirred for 4 hours. After the reaction was completed, the temperature was lowered to room temperature and then filtered. A filtrate was poured into water, an organic layer was extracted with methylene chloride, and the organic layer was dried over $MgSO_4$. The dried organic layer was concentrated under reduced pressure and then columned with EA:Hex=1:5, and thus Compound 153 (2.1 g, yield: 51%) was prepared.

Mass: $[(M+H)^+]$: 578.

[Synthesis Example 15] Synthesis of Compound 161

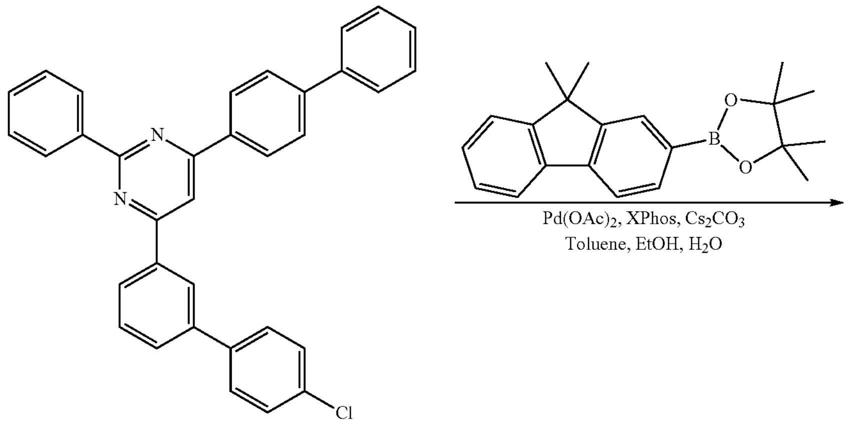

Py-8

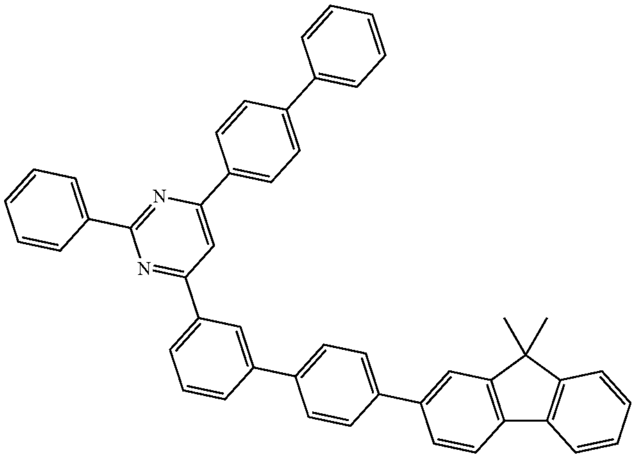

161

3.0 g of Py-8 synthesized in Preparation Example 8, 2.8 g of 2-(9,9-dimethyl-9H-fluoren-2-yl)-4,4,5,5-tetramethyl-1,3,2-dioxaborolan, and 3.0 g of $Cs_2CO_3$ were mixed, 60 ml of toluene, 12 ml of ethanol, and 12 ml of water were added thereto, and 55 mg of $Pd(OAc)_2$ and 250 mg of Xphos were further added thereto, and the mixture was heated and stirred for 4 hours. After the reaction was completed, the temperature was lowered to room temperature and then filtered. A filtrate was poured into water, an organic layer was extracted with methylene chloride, and the organic layer was dried over $MgSO_4$. The dried organic layer was concentrated under reduced pressure and then columned with MC:Hex=1:2, and thus Compound 161 (2.2 g, yield: 52%) was prepared.

Mass: $[(M+H)^+]$: 654. 187

[Synthesis Example 16] Synthesis of Compound
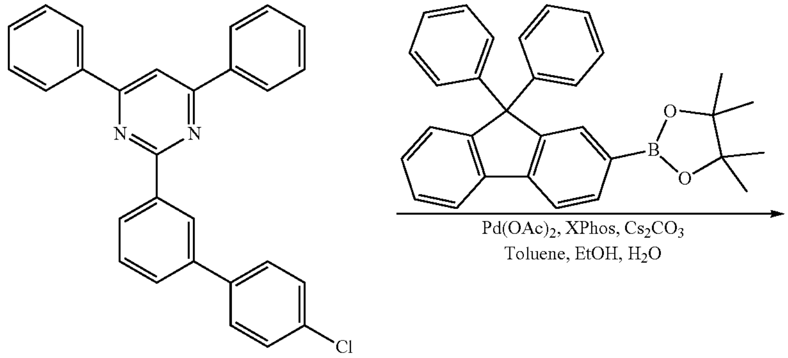
Py-5
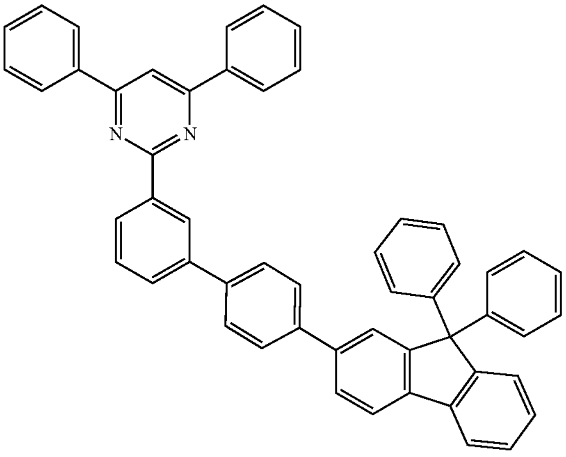
187
Compound 187 (2.3 g, yield: 53%) was prepared in the same manner as in Synthesis Example 12, except that 2-(9,9-dimethyl-9H-fluoren-2-yl)-4,4,5,5-tetramethyl-1,3,2-dioxaborolan was used instead of 2-(9,9-dimethyl-9H-fluoren-4-yl)-4,4,5,5-tetramethyl-1,3,2-dioxaborolan used in Synthesis Example 12.
Mass: $[(M+H)^+]$: 702.
[Synthesis Example 17] Synthesis of Compound 191
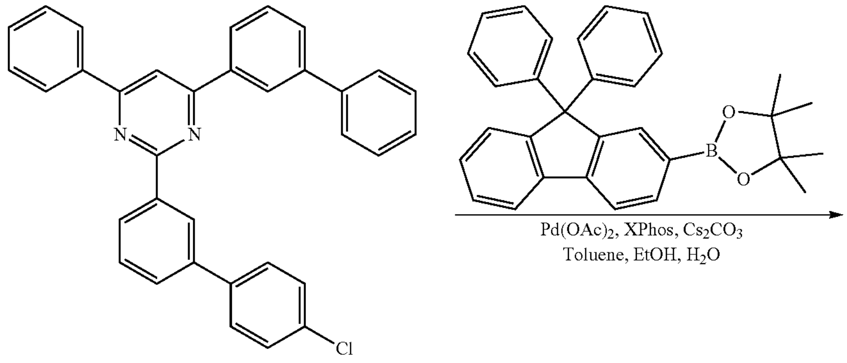
Py-7

-continued
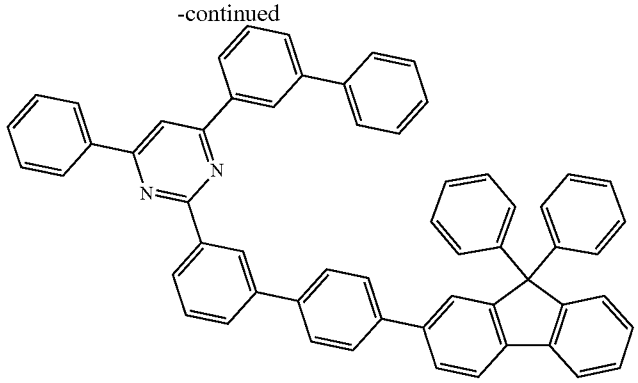
191
Compound 191 (2.2 g, yield: 53%) was prepared in the same manner as in Synthesis Example 13, except that 2-(9,9-dimethyl-9H-fluoren-2-yl)-4,4,5,5-tetramethyl-1,3,2-dioxaborolan was used instead of 2-(9,9-dimethyl-9H-fluoren-1-yl)-4,4,5,5-tetramethyl-1,3,2-dioxaborolan used in Synthesis Example 13.
Mass: $[(M+H)^+]$: 778.
[Synthesis Example 18] Synthesis of Compound 201
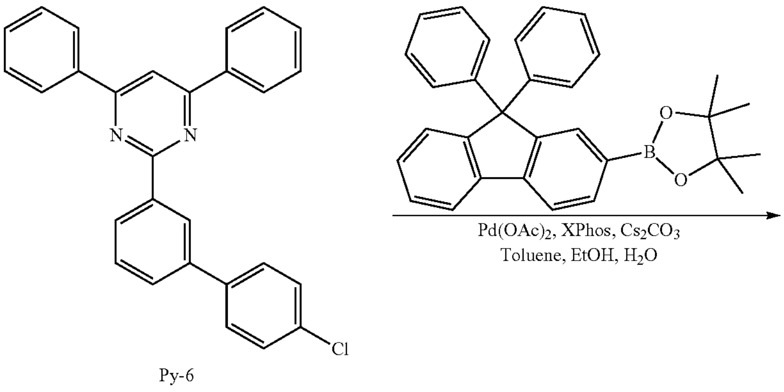
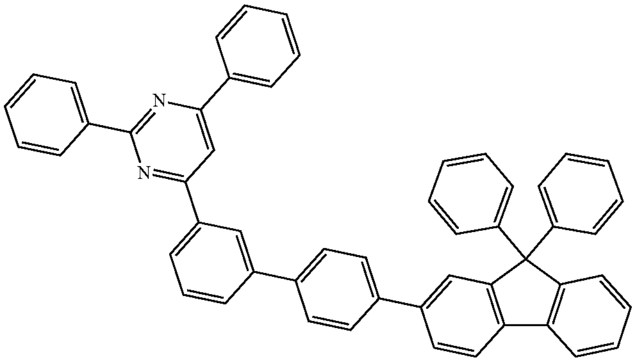
201

Compound 201 (2.4 g, yield: 55%) was prepared in the same manner as in Synthesis Example 14, except that 2-(9,9-diphenyl-9H-fluoren-2-yl)-4,4,5,5-tetramethyl-1,3,2-dioxaborolan was used instead of 2-(9,9-dimethyl-9H-fluoren-3-yl)-4,4,5,5-tetramethyl-1,3,2-dioxaborolan used in Synthesis Example 14.

Mass: [(M+H)+]: 702.

[Synthesis Example 19] Synthesis of Compound 206

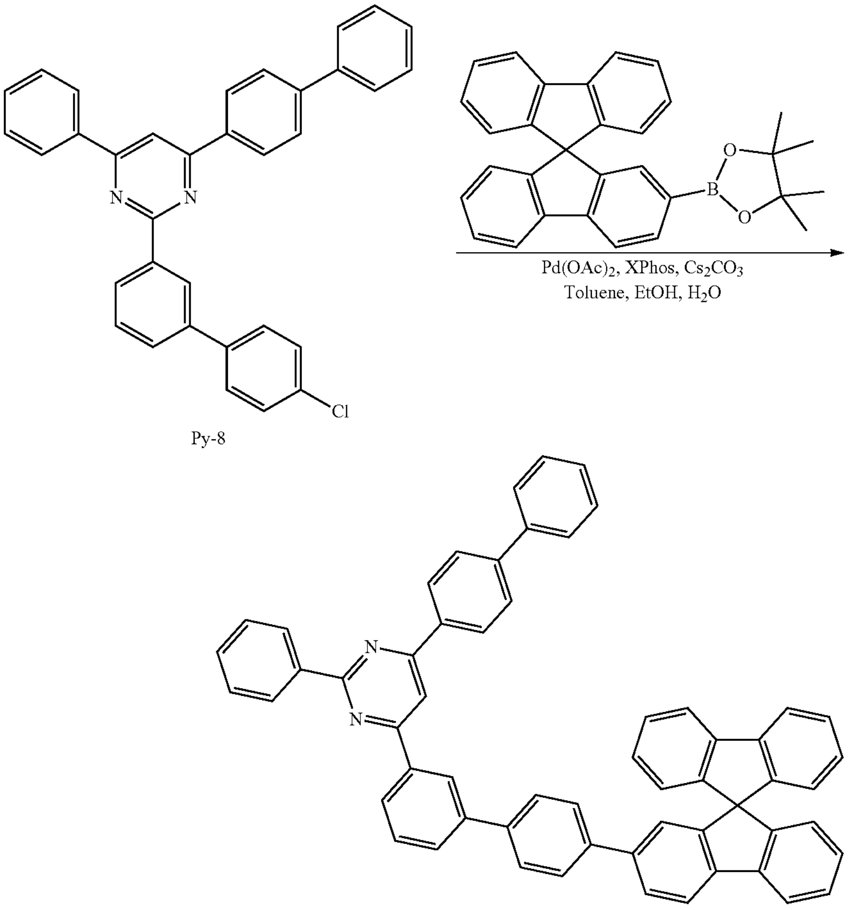

Py-8

206

Compound 206 (2.3 g, yield: 52%) was prepared in the same manner as in Synthesis Example 15, except that 2-(9,9'-spirobi[fluoren]-2-yl)-4,4,5,5-tetramethyl-1,3,2-dioxaborolan was used instead of 2-(9,9-dimethyl-9H-fluoren-2-yl)-4,4,5,5-tetramethyl-1,3,2-dioxaborolan used in Synthesis Example 15.

Mass: [(M+H)+]: 776.

[Synthesis Example 20] Synthesis of Compound 227
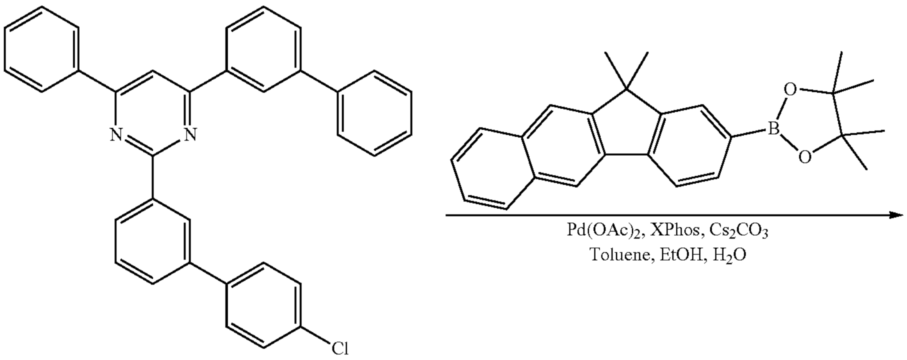
Py-7
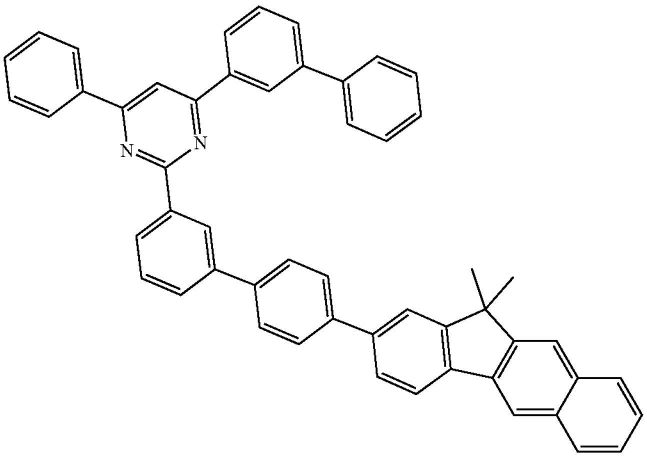
227
Compound 227 (2.2 g, yield: 52%) was prepared in the same manner as in Synthesis Example 13, except that 2-(11,11-dimethyl-11H-benzo[b]fluoren-2-yl)-4,4,5,5-tetramethyl-1,3,2-dioxaborolan was used instead of 2-(9,9-dimethyl-9H-fluoren-1-yl)-4,4,5,5-tetramethyl-1,3,2-dioxaborolan used in Synthesis Example 13.
Mass: [(M+H)$^+$]: 704.
[Synthesis Example 21] Synthesis of Compound 233
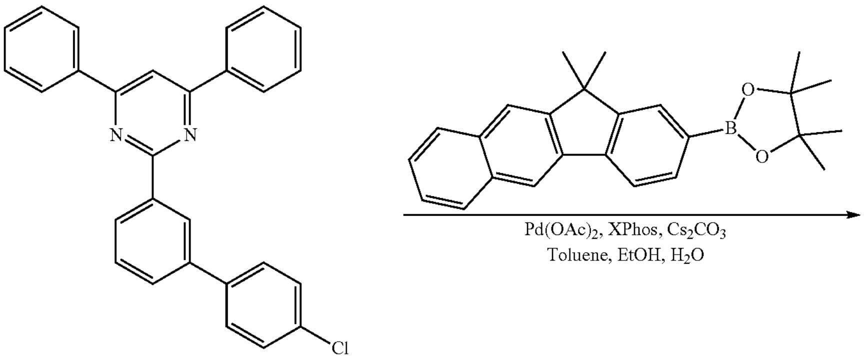
Py-6

-continued
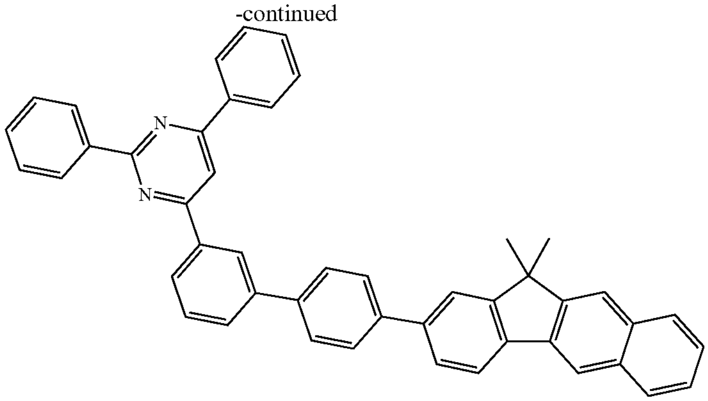
233
Compound 233 (2.3 g, yield: 53%) was prepared in the same manner as in Synthesis Example 14, except that 2-(11,11-dimethyl-11H-benzo[b]fluoren-2-yl)-4,4,5,5-tetramethyl-1,3,2-dioxaborolan was used instead of 2-(9,9-dimethyl-9H-fluoren-3-yl)-4,4,5,5-tetramethyl-1,3,2-dioxaborolan used in Synthesis Example 14.
Mass: $[(M+H)^+]$: 628.
[Synthesis Example 22] Synthesis of Compound 236
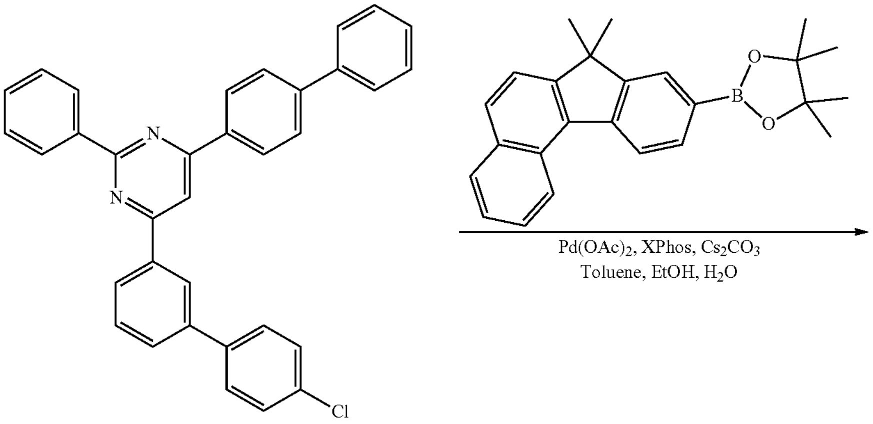
Py-8

-continued

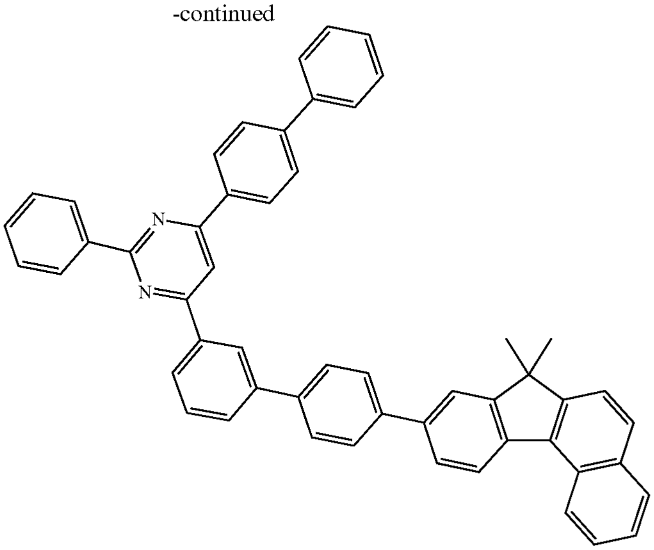

236

Compound 236 (2.3 g, yield: 52%) was prepared in the same manner as in Synthesis Example 15, except that 2-(7,7-dimethyl-7H-benzo[c]fluoren-9-yl)-4,4,5,5-tetramethyl-1,3,2-dioxaborolan was used instead of 2-(9,9-dimethyl-9H-fluoren-2-yl)-4,4,5,5-tetramethyl-1,3,2-dioxaborolan used in Synthesis Example 15.

Mass: $[(M+H)^+]$: 704.

[Embodiment 1] Preparation of Blue Organic EL Device

Compound 3 synthesized in Synthesis Example was subjected to high-purity sublimation purification in a conventionally known method, and then a blue organic EL device was prepared as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone and methanol, dried, transferred to a UV OZONE cleaner (Power sonic 405, Hwasin Tech) cleaned for 5 minutes using UV, and then transferred to a vacuum evaporator.

On the ITO transparent electrode prepared as above, DS-205 (Doosan Electronics Co., Ltd., 80 nm)/NPB (15 nm)/ADN+5% DS-405 (Doosan Electronics Co., Ltd., 30 nm)/Compound 3 (30 nm)/LiF (1 nm)/Al (200 nm) were stacked in the order, so that an organic EL device was prepared. Structures of NPB and ADN used in such a case were as follows.

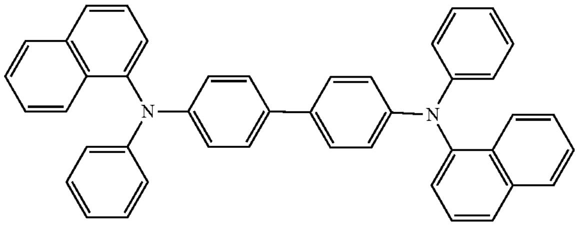

NPB

-continued

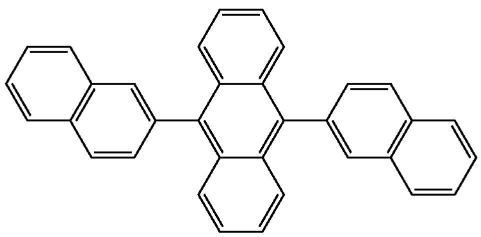

ADN

[Embodiments 2 to 11] Preparation of Blue Organic EL Devices

Blue organic EL devices of Embodiments 2 to 11 were prepared in the same manner as in Embodiment 1, except that Compounds shown in Table 1 were respectively used instead of Compound 3 which was used as an electron transport layer material in the forming of the electron transport layer in Embodiment 1.

[Comparative Example 1] Preparation of Blue Organic EL Device

A blue organic EL device was prepared in the same manner as in Embodiment 1, except that $Alq_3$ was used instead of Compound 3 which was used as an electron transport layer material in Embodiment 1. A structure of $Alq_3$ used in such a case was as follows.

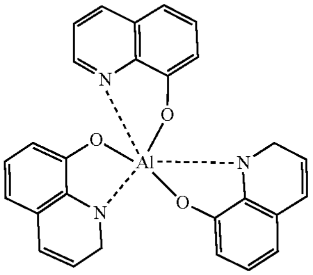

$Alq_3$

[Comparative Example 2] Preparation of Blue Organic EL Device

A blue organic EL device was prepared in the same manner as in Embodiment 1, except that Compound 3 which was used as an electron transport layer material in Embodiment 1 was not used.

[Comparative Example 3] Preparation of Blue Organic EL Device

A blue organic EL device was prepared in the same manner as in Embodiment 1, except that T-1 was used instead of Compound 3 which was used as an electron transport layer material in Embodiment 1. A structure of T-1 used in such a case was as follows.

T-1

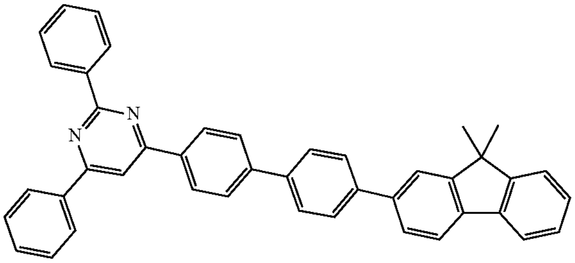

[Comparative Example 4] Preparation of Blue Organic EL Device

A blue organic EL device was prepared in the same manner as in Embodiment 1, except that T-2 was used instead of Compound 3 which was used as an electron transport layer material in Embodiment 1. A structure of T-2 used in such a case was as follows.

T-2

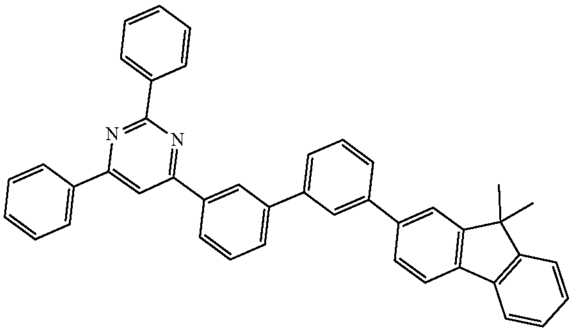

Evaluation Example 1

For each of the blue organic EL devices prepared in Embodiments 1 to 11 and Comparative Examples 1 to 4, a driving voltage, a current efficiency and an emission peak at a current density of 10 $mA/cm^2$ were measured and the results are shown in Table 1 below.

TABLE 1

| Sample | Electron transport layer | Driving voltage (V) | Emission peak (nm) | Current efficiency (cd/A) |
|---|---|---|---|---|
| Embodiment 1 | Compound 3 | 3.0 | 455 | 7.7 |
| Embodiment 2 | Compound 29 | 3.2 | 454 | 8.1 |
| Embodiment 3 | Compound 62 | 3.3 | 455 | 8.2 |
| Embodiment 4 | Compound76 | 3.4 | 454 | 8.1 |
| Embodiment 5 | Compound 102 | 3.5 | 455 | 8.2 |
| Embodiment 6 | Compound 111 | 3.1 | 453 | 8.1 |
| Embodiment 7 | Compound 131 | 3.8 | 455 | 9.1 |
| Embodiment 8 | Compound 161 | 3.7 | 454 | 8.7 |
| Embodiment 9 | Compound 191 | 3.7 | 455 | 8.6 |
| Embodiment 10 | Compound 206 | 3.8 | 454 | 8.6 |
| Embodiment 11 | Compound 233 | 3.5 | 455 | 8.8 |
| Comp. Ex. 1 | $Alq_3$ | 4.8 | 457 | 5.6 |
| Comp. Ex. 2 | — | 4.7 | 459 | 6.1 |
| Comp. Ex. 3 | T-1 | 4.4 | 459 | 5.9 |
| Comp. Ex. 4 | T-2 | 3.9 | 456 | 7.2 |

As shown in Table 1, it was appreciated that the blue organic EL devices of Embodiments 1 to 11 in which the compounds of the present invention were used in the electron transport layer exhibited excellent performance in terms of the driving voltage, the emission peak and the current efficiency, as compared to the blue organic EL device in Comparative Example 1 in which conventional $Alq_3$ was used in the electron transport layer and the blue organic EL device in Comparative Example 2 in which the electron transport layer was not included.

In addition, Compounds 3, 29, 62, 76, 102, 111, 131, 161, 191, 206, and 233 synthesized in the above Synthesis Examples contain m,p-biphenylene or p,m-biphenylene as a linking group. It was appreciated that the blue organic EL devices of Embodiments 1 to 11 in which such compounds were used for the electron transport layer exhibited excellent performance in terms of the driving voltage, the emission peak and the current efficiency, as compared to the blue organic EL devices of Comparative Examples 3 and 4 in which compounds containing p,p-biphenylene or m,m-biphenylene as a linking group were used for the electron transport layer.

[Embodiment 12] Preparation of Blue Organic EL Device

Compound 12 synthesized in Synthesis Example was subjected to high-purity sublimation purification in a conventionally known method, and then a blue organic EL device was prepared as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone and methanol, dried, transferred to a UV OZONE cleaner (Power sonic 405, Hwasin Tech) cleaned for 5 minutes using UV, and then transferred to a vacuum evaporator.

On the ITO transparent electrode prepared as above, DS-205 (Doosan Electronics Co., Ltd., 80 nm)/NPB (15 nm)/ADN+5% DS-405 (Doosan Electronics Co., Ltd., 30 nm)/Compound 12 (5 nm)/$Alq_3$ (25 nm)/LiF (1 nm)/Al (200 nm) were stacked in the order, so that an organic EL device was prepared.

[Embodiments 13 to 22] Preparation of Blue Organic EL Devices

Organic EL devices of Embodiments 13 to 22 were prepared in the same manner as in Embodiment 12, except that Compounds shown in Table 2 were respectively used instead of Compound 12 which was used as an electron transport auxiliary layer material in Embodiment 12.

[Comparative Example 5] Preparation of Blue Organic EL Device

A blue organic EL device was prepared in the same manner as in Embodiment 12, except that Compound 12 which was used as an electron transport auxiliary layer material in Embodiment 12 was not used and that $Alq_3$, an electron transport layer material, was deposited to 30 nm instead of 25 nm.

[Comparative Example 6] Preparation of Blue Organic EL Device

A blue organic EL device was prepared in the same manner as in Embodiment 12, except that T-1 was used instead of Compound 12 which was used as an electron transport auxiliary layer material in Embodiment 12. The structure of T-1 used in such a case is the same as that described in Comparative Example 3, and thus it will be omitted.

[Comparative Example 7] Preparation of Blue Organic EL Device

A blue organic EL device was prepared in the same manner as in Embodiment 12, except that T-2 was used instead of Compound 12 which was used as an electron transport auxiliary layer material in Embodiment 12. The structure of T-2 used in such a case is the same as that described in Comparative Example 4, and thus it will be omitted.

Evaluation Example 2

For each of the blue organic EL devices prepared in Embodiments 12 to 22 and Comparative Examples 5 to 7, a driving voltage, a current efficiency and an emission peak at a current density of 10 mA/$cm^2$ were measured and the results are shown in Table 2 below.

TABLE 2

| Sample | Electron transport auxiliary layer | Driving voltage (V) | Emission peak (nm) | Current efficiency (cd/A) |
|---|---|---|---|---|
| Embodiment 12 | Compound 12 | 3.2 | 455 | 8.1 |
| Embodiment 13 | Compound 36 | 3.1 | 453 | 8.2 |
| Embodiment 14 | Compound 66 | 3.1 | 454 | 8.3 |
| Embodiment 15 | Compound 81 | 3.1 | 456 | 8.1 |
| Embodiment 16 | Compound 110 | 3.2 | 454 | 8.1 |
| Embodiment 17 | Compound 129 | 3.3 | 455 | 8.2 |
| Embodiment 18 | Compound 153 | 3.3 | 454 | 9.1 |
| Embodiment 19 | Compound 187 | 3.2 | 455 | 8.8 |
| Embodiment 20 | Compound 201 | 3.1 | 456 | 8.7 |
| Embodiment 21 | Compound 227 | 3.2 | 454 | 8.8 |
| Embodiment 22 | Compound 236 | 3.3 | 455 | 8.4 |
| Comp. Ex. 5 | — | 4.7 | 459 | 6.1 |
| Comp. Ex. 6 | T-1 | 4.3 | 459 | 5.9 |
| Comp. Ex. 7 | T-2 | 3.6 | 455 | 7.3 |

As shown in Table 2, it was appreciated that the blue organic EL devices of Embodiments 12 to 22 in which the compounds of the present invention were used in the electron transport auxiliary layer exhibited excellent performance in terms of the current efficiency, the emission peak, and particularly the driving voltage, as compared to the blue organic EL device of Comparative Example 3 in which the electron transport auxiliary layer was not included.

In addition, Compounds 13, 36, 66, 81, 110, 129, 153, 187, 201, 227, and 236 synthesized in the above Synthesis Examples contain m,p-biphenylene or p,m-biphenylene as a linking group. It was appreciated that the blue organic EL devices of Embodiments 12 to 22 in which such compounds were used for the electron transport auxiliary layer exhibited excellent performance in terms of the driving voltage, the emission peak and the current efficiency, as compared to the blue organic EL devices of Comparative Examples 6 and 7 in which compounds containing p,p-biphenylene or m,m-biphenylene as a linking group were used for the electron transport auxiliary layer.

The invention claimed is:

1. An organic compound of the following Chemical Formula 1 or 2:

[Chemical Formula 1]

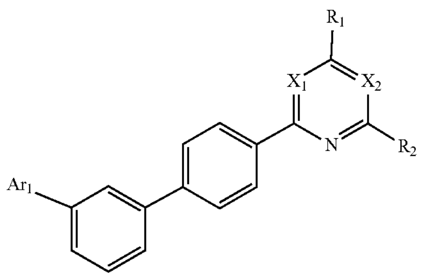

-continued

[Chemical Formula 2]

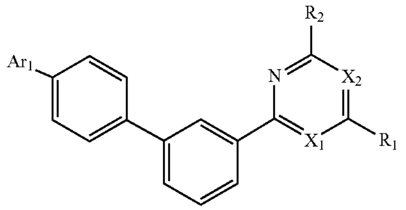

wherein $X_1$ and $X_2$ are different from each other and are $CR_3$ or N, wherein one of $X_1$ and $X_2$ is N and the other is $CR_3$, $R_1$ and $R_2$ are the same as or different from each other, each independently being selected from: a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a C to $C_{40}$ alkyl group, a $C_6$ to $C_{60}$ aryl group, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphin oxide group, and a $C_6$ to $C_{60}$ arylamine group, $Ar_1$ is a substituent represented by any one of the following Chemical Formulas F2 to F4:

F2

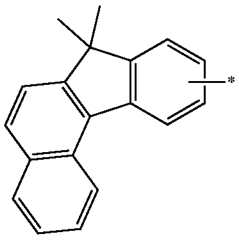

F3

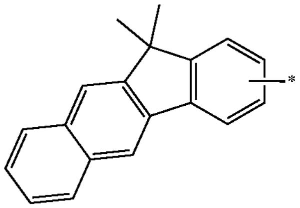

F4

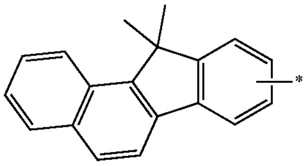

$R_3$ is selected from: hydrogen, deuterium, halogen, a cyano group, a $C_1$ to $C_{40}$ alkyl group, a $C_6$ to $C_{60}$ aryl group, a heteroaryl group having 5 to 60 nuclear atoms, the alkyl group, the aryl group, and the heteroaryl group of $R_3$ are each independently unsubstituted or substituted with one or more substituents of: deuterium, halogen, a cyano group, a nitro group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and when the substituents are plural in number, the substituents are the same as or different from each other, and the alkenyl group, the alkynyl group, the cycloalkyl group, the heterocycloalkyl group, the alkyl group, the aryl group, the alkyloxy group, the aryloxy group, the alkylsilyl group, the arylsilyl group, the alkylboron group, the arylboron group, the arylphosphine group, the arylphosphine oxide group and the arylamine group of $R_1$ and $R_2$ are each independently substituted or unsubstituted with one or more substituents of: deuterium, halogen, a cyano group, a nitro group, a $C_2$ to $C_{40}$ alkenyl group, a $C_2$ to $C_{40}$ alkynyl group, a $C_3$ to $C_{40}$ cycloalkyl group, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and when the substituents are plural in number, the substituents are the same as or different from each other, provided that when $R_1$ is aryl, $R_2$ is aryl, or both $R_1$ and $R_2$ are aryl, said aryl is not substituted with a heteroaryl group.

2. The organic compound of claim 1, wherein $R_1$ and $R_2$ are different from each other.

3. The organic compound of claim 2, wherein any one of $R_1$ and $R_2$ is a biphenyl group or a terphenyl group, and the other is a phenyl group.

4. The organic compound of claim 1, wherein $X_1$ is $CR_3$, $X_2$ is N, and $R_3$ is as defined in claim 1.

5. The organic compound of claim 1, wherein the compound of 1 or 2 is selected from the following Compounds 101 to 125 and 226 to 250:

101

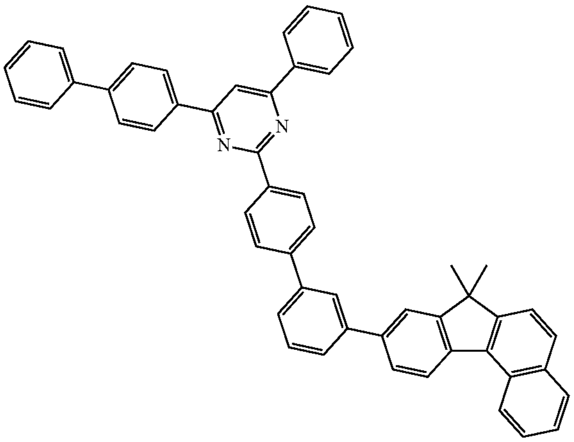

-continued
102
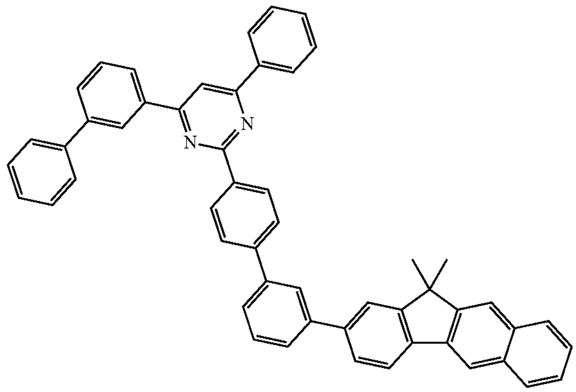
103
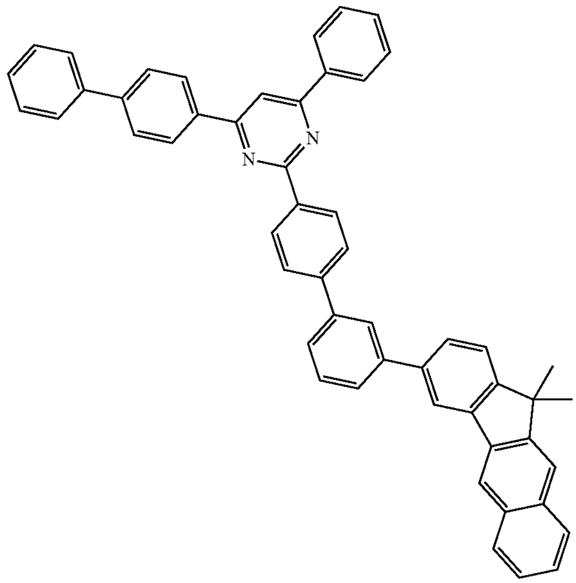
104
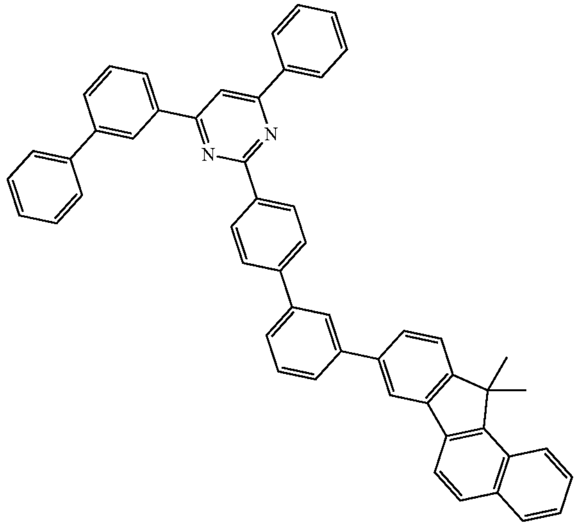
-continued
105
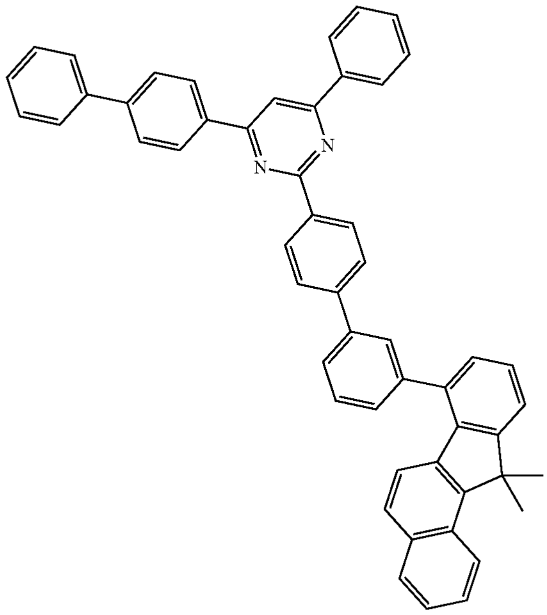
106
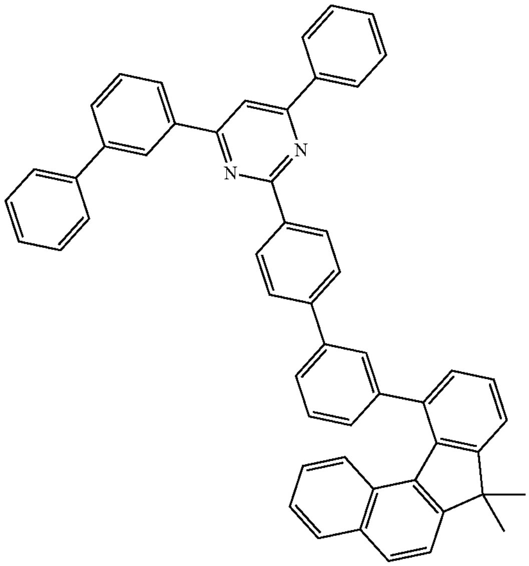

-continued
107
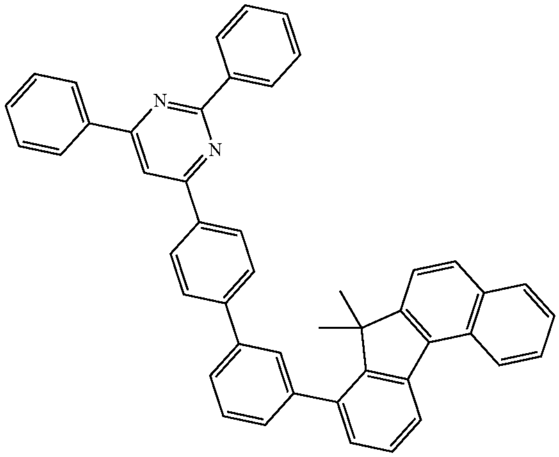
108
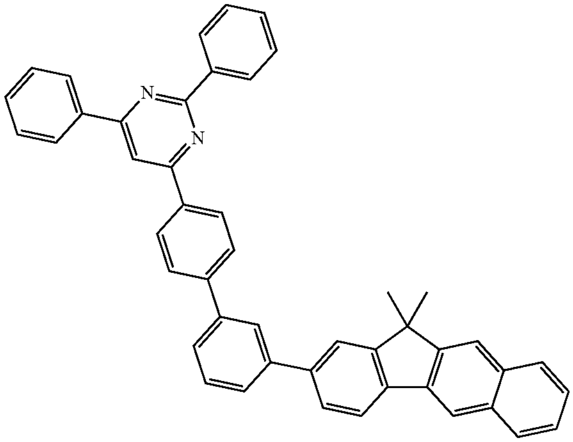
109
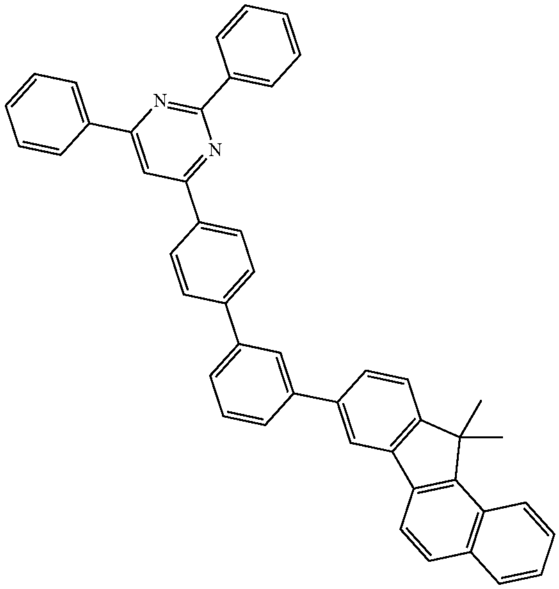
-continued
110
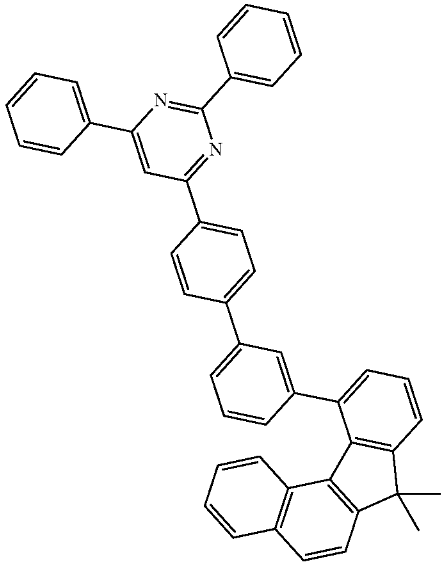
111
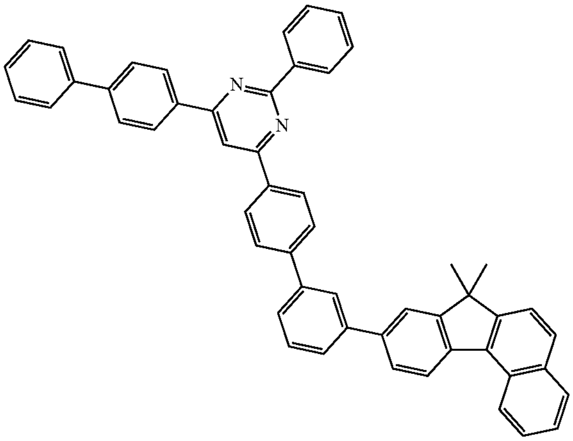
112
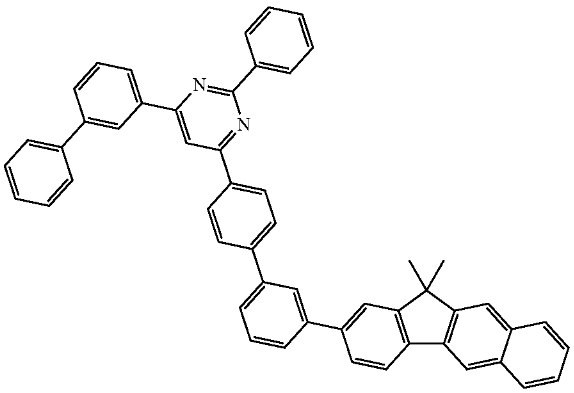

-continued
113
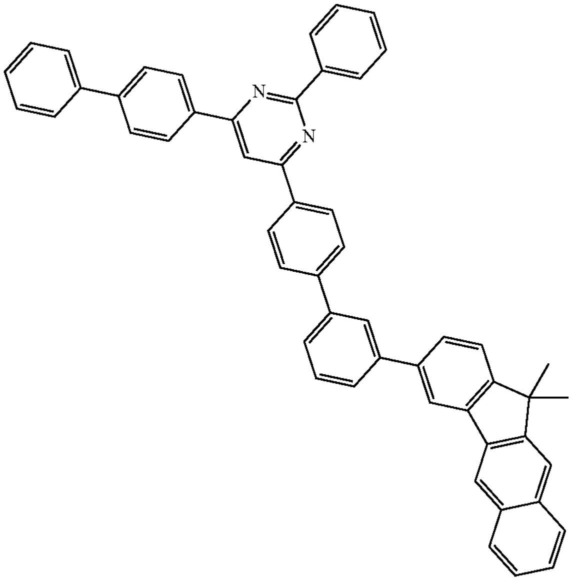
114
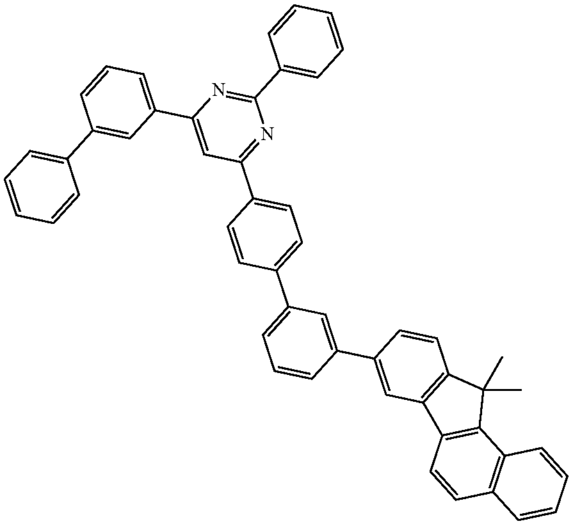
-continued
115
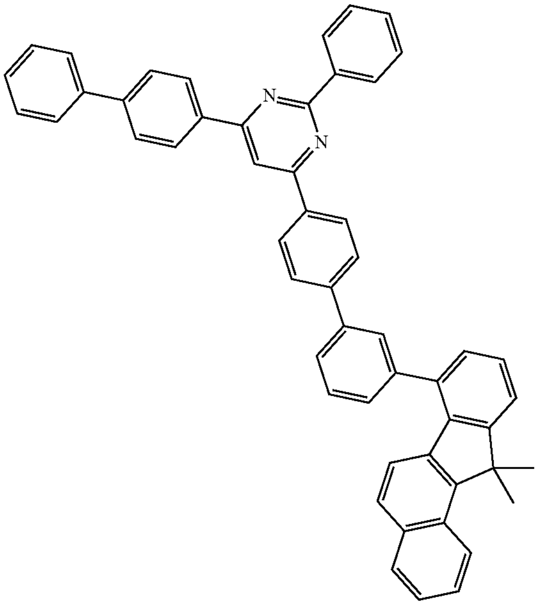
116
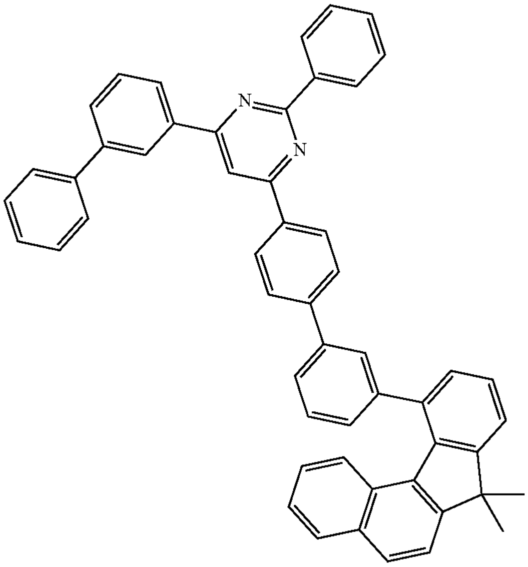
117
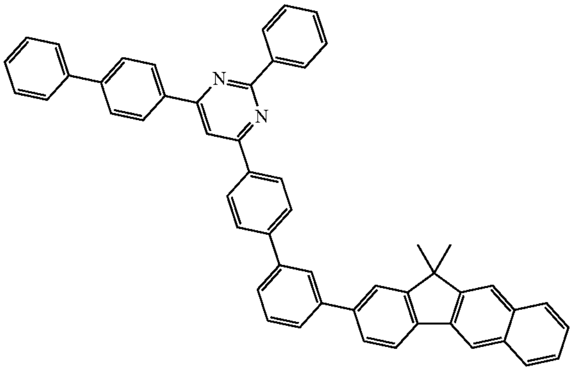

-continued
118
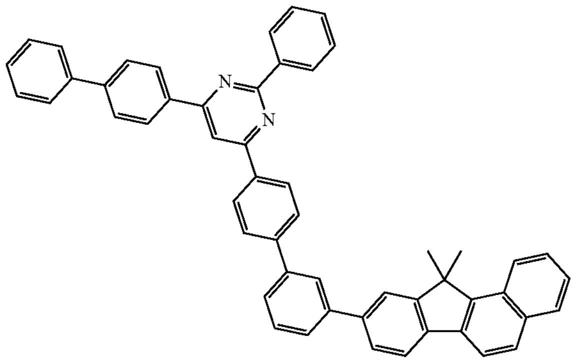
119
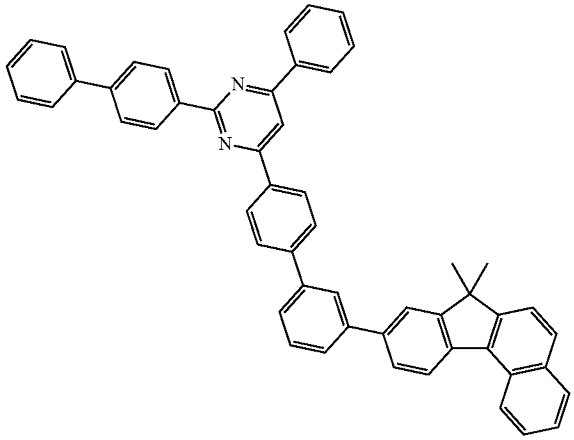
120
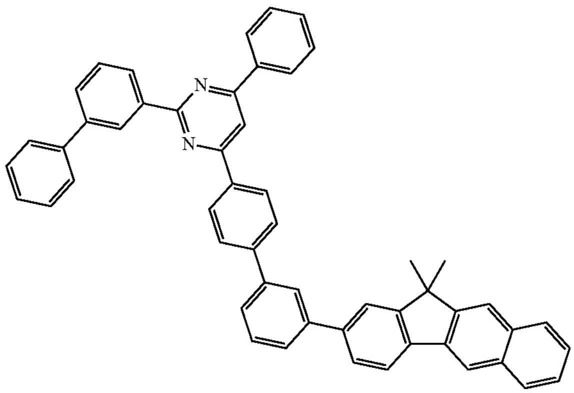
-continued
121
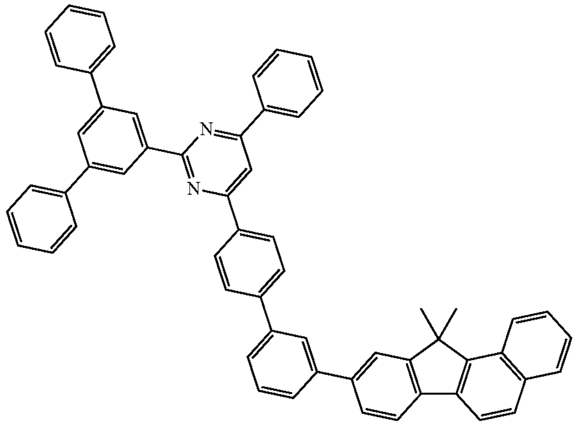
122
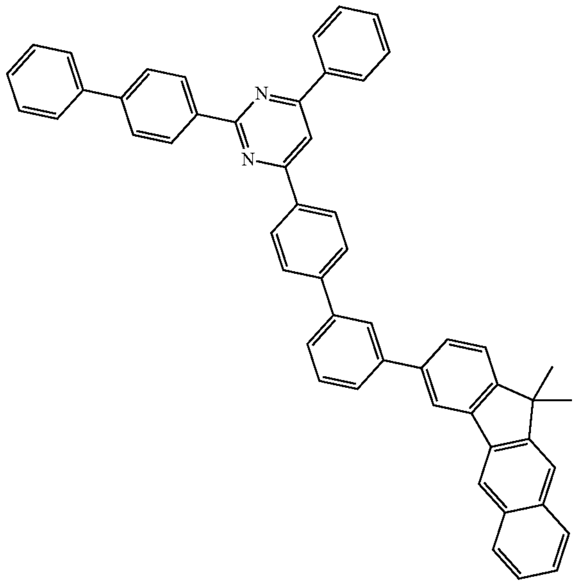
123
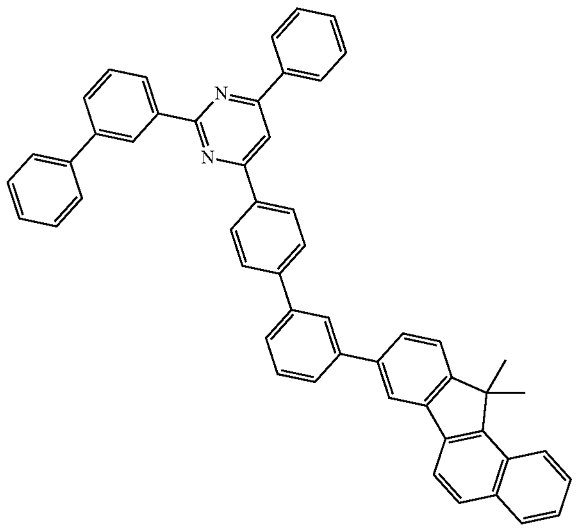

-continued
124
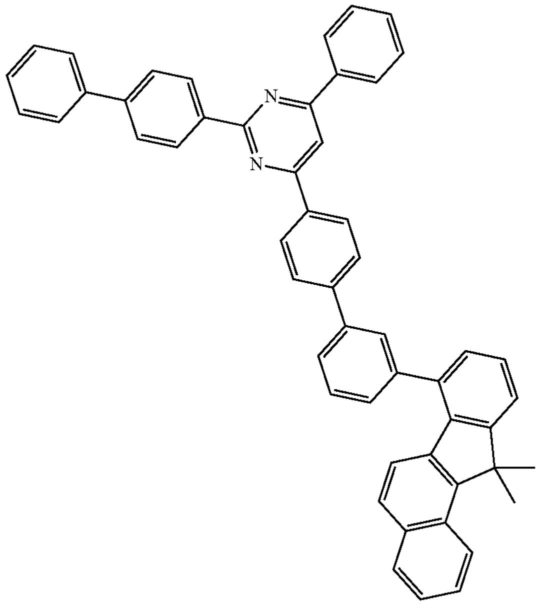
125
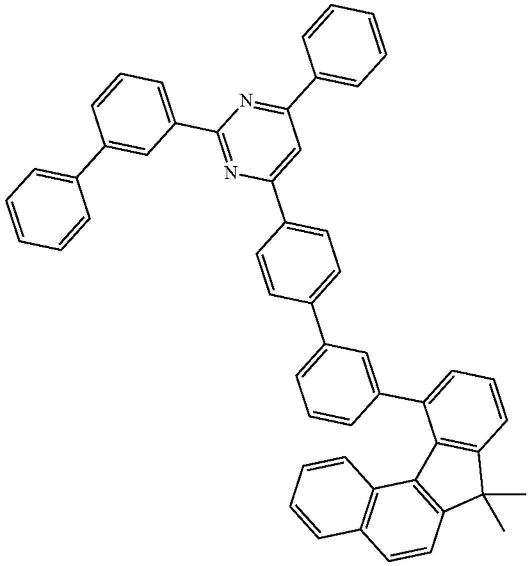
226
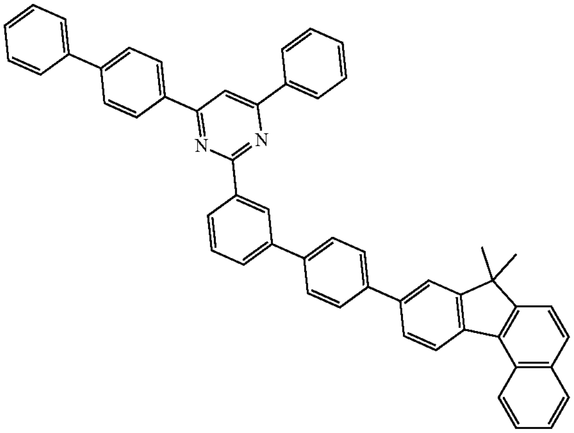
-continued
227
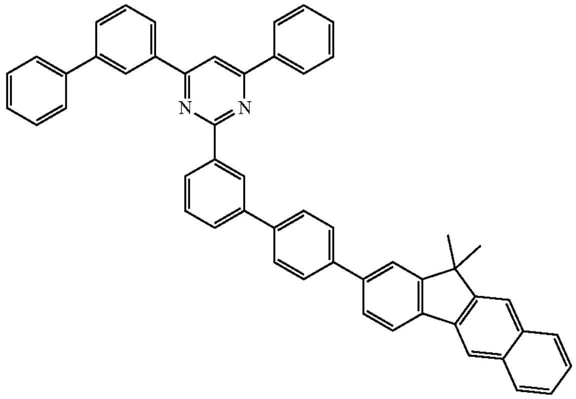
228
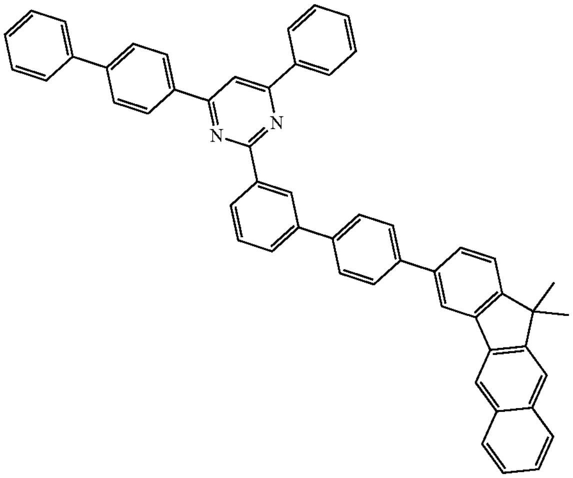
229
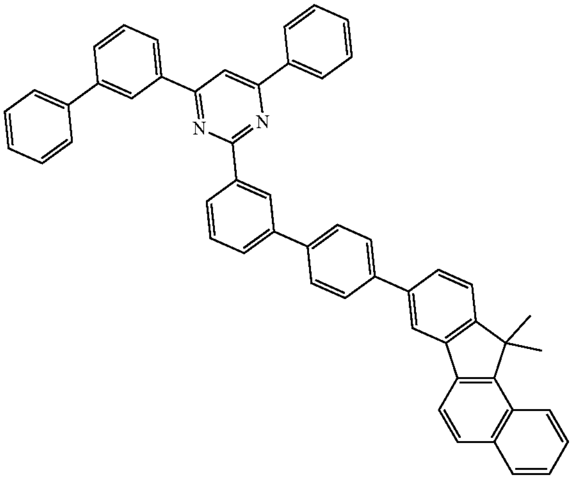

-continued
230
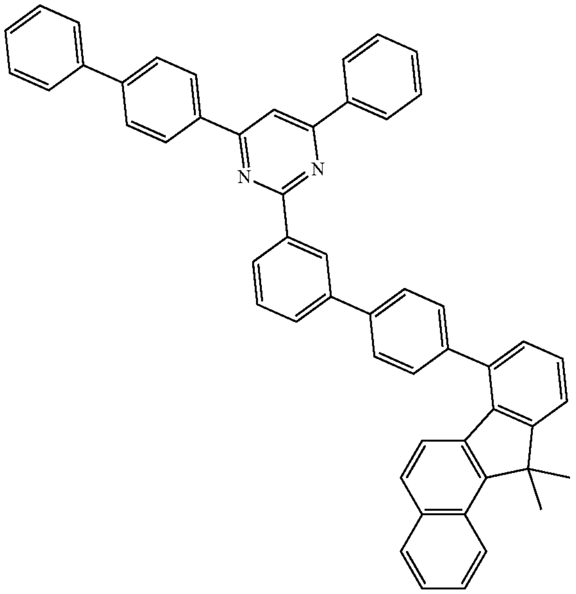
231
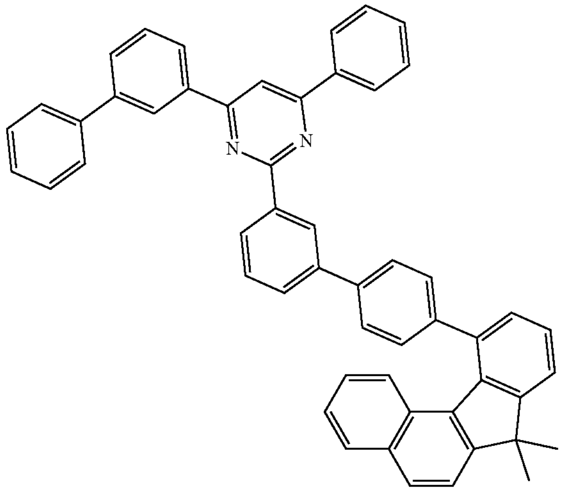
232
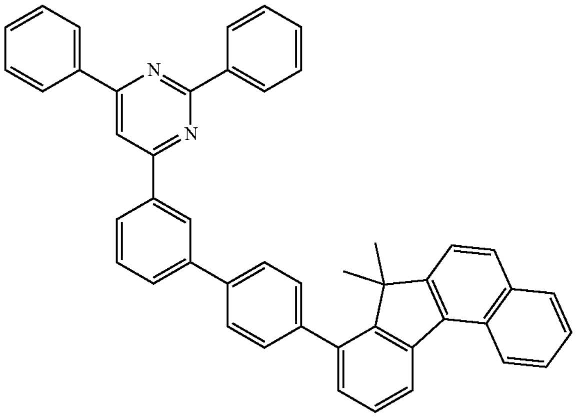
-continued
233
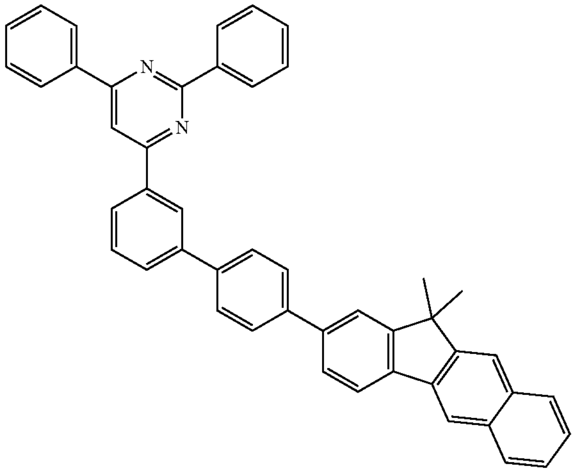
234
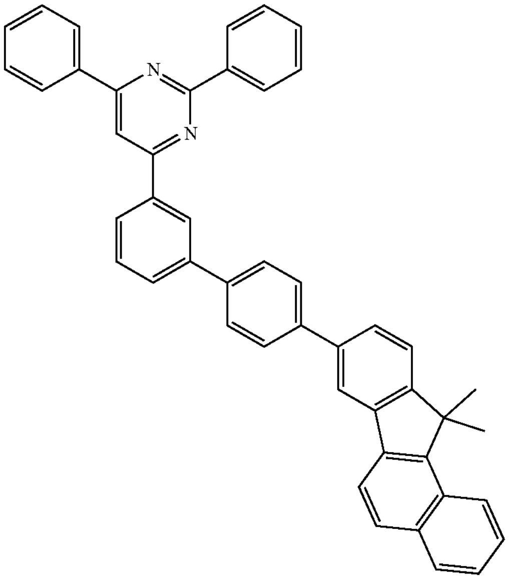
235
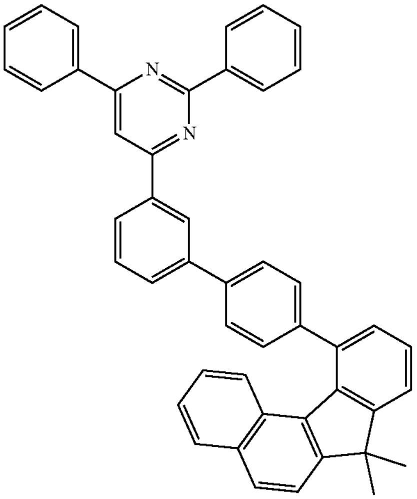

-continued
236
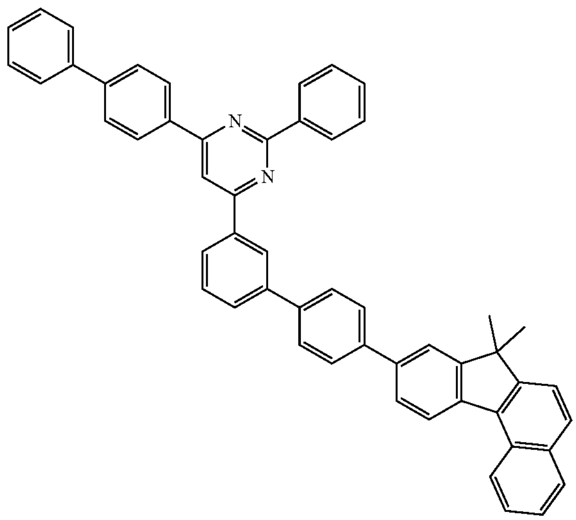
237
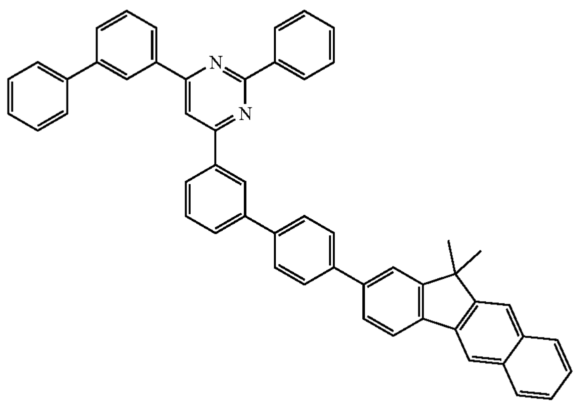
238
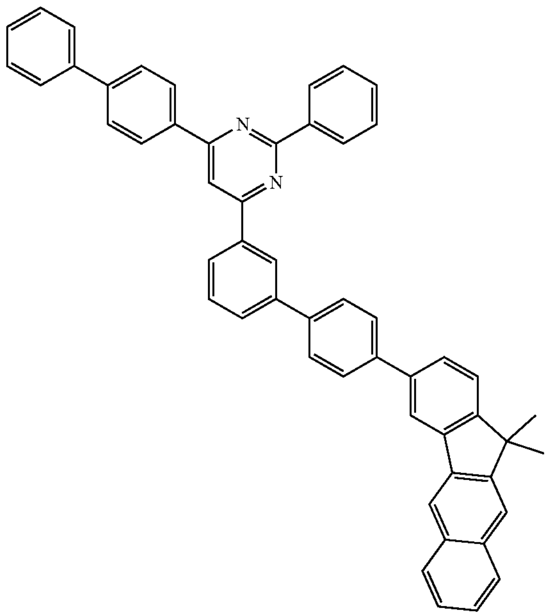
-continued
239
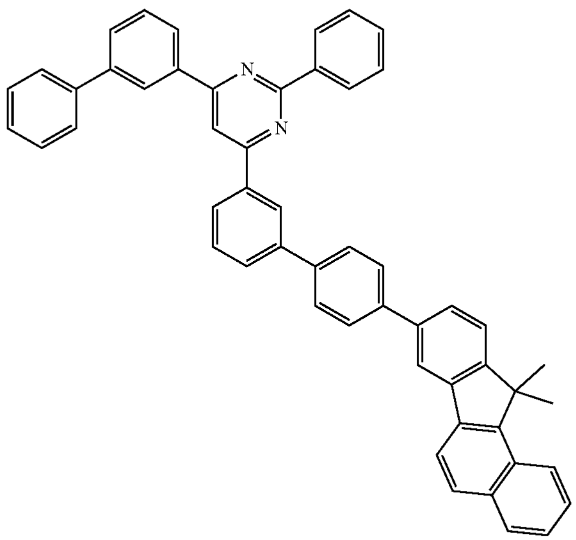
240
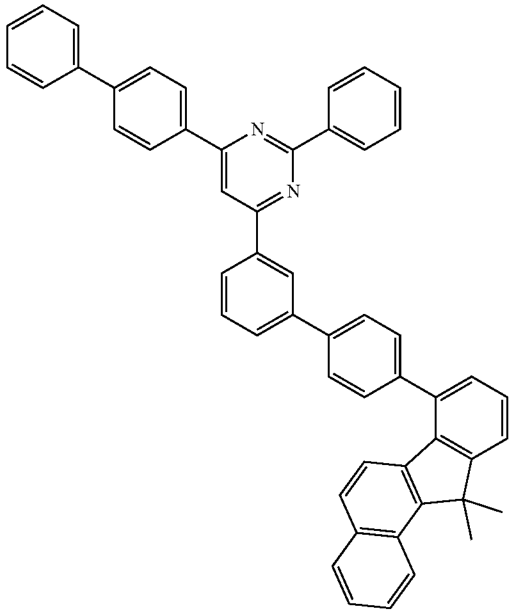

-continued
241
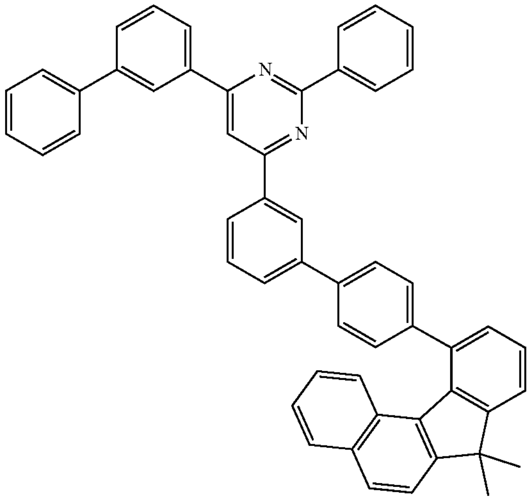
242
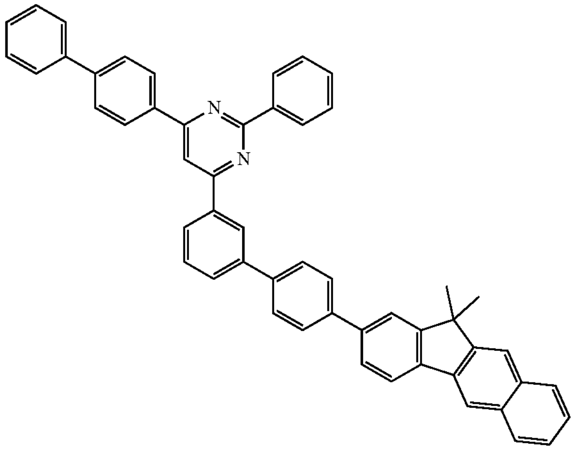
243
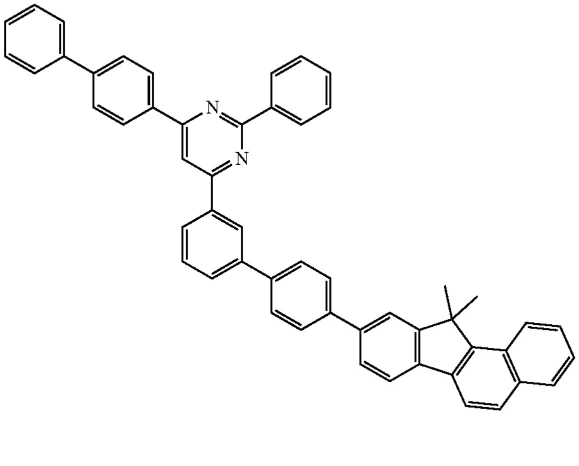
244
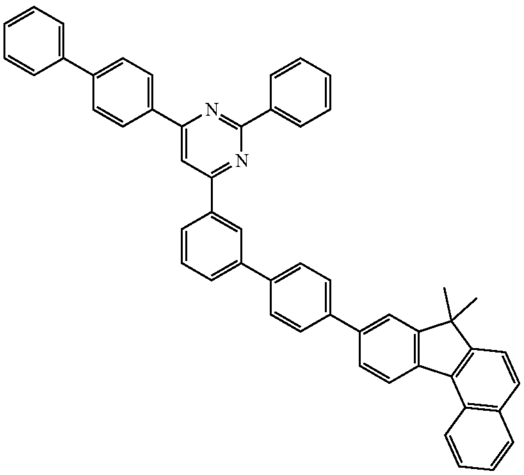
245
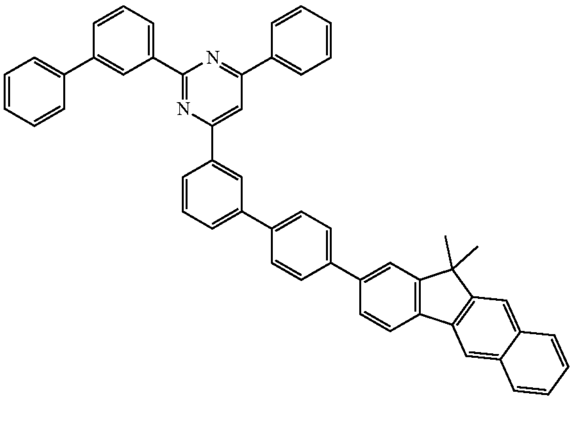
246
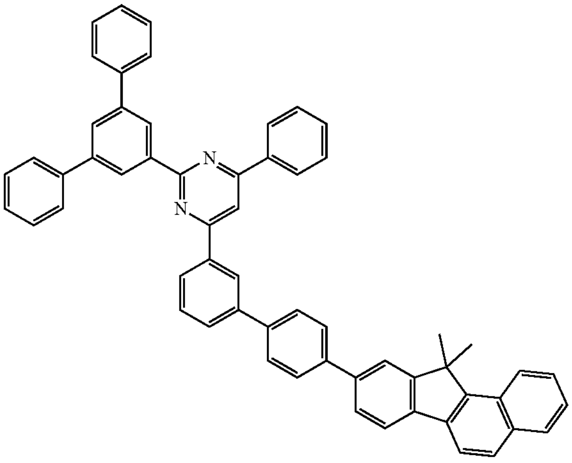

-continued
247
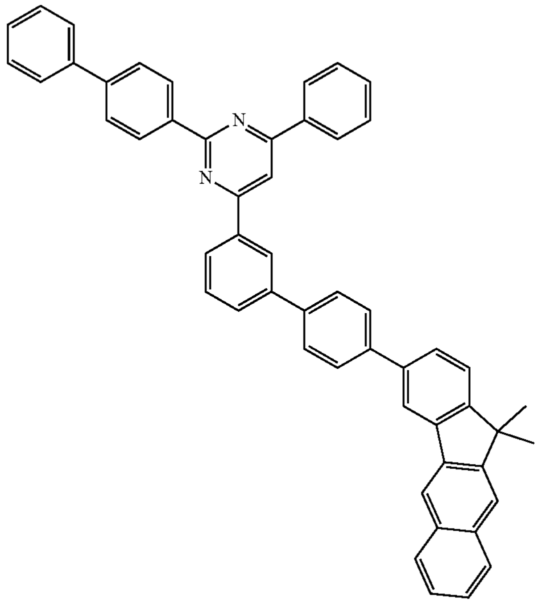
248
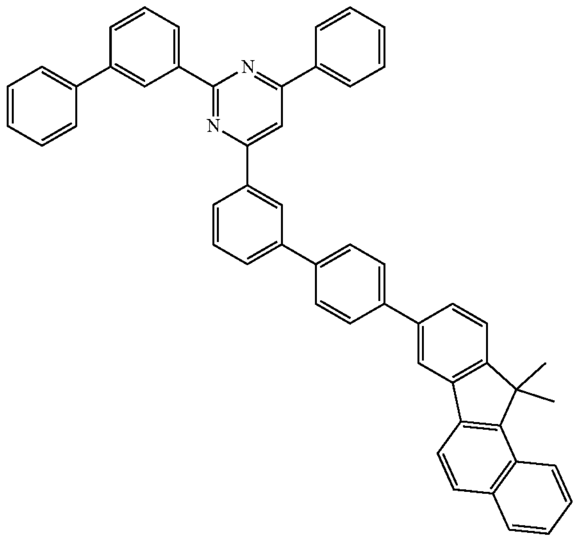
-continued
249
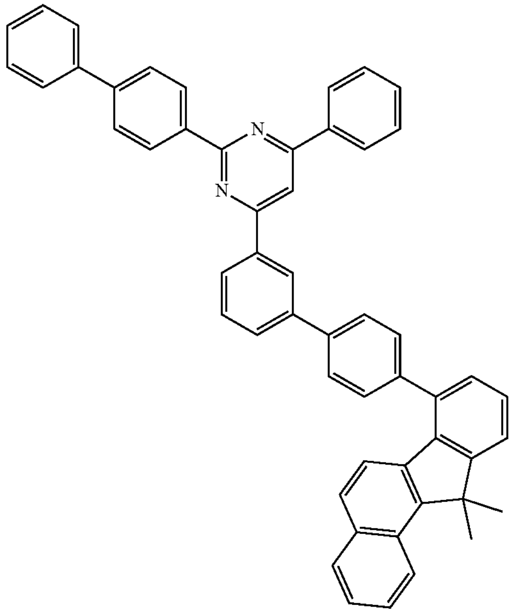
250
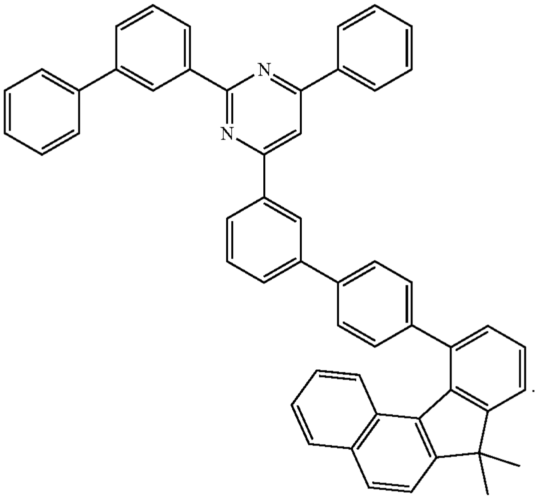
6. An electroluminescent device comprising: an anode, a cathode, and one or more organic layer disposed between the anode and the cathode,
wherein at least one of the one or more organic layer comprises a compound of the following Chemical Formula 1 or 2:
[Chemical Formula 1]
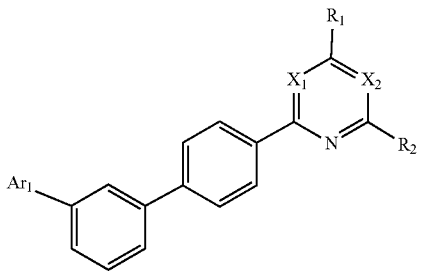

-continued

[Chemical Formula 2]

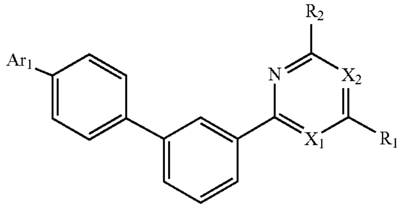

wherein $X_1$ and $X_2$ are different from each other and are $CR_3$ or N, wherein one of $X_1$ and $X_2$ is N and the other is $CR_3$, $R_1$ and $R_2$ are the same as or different from each other, each independently being selected from: a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphin oxide group, and a $C_6$ to $C_{60}$ arylamine group, $Ar_1$ is a substituent of any one of the following Chemical Formulas F2 to F4:

F2

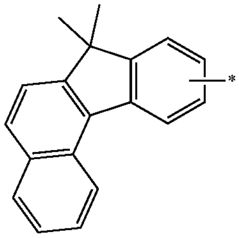

F3

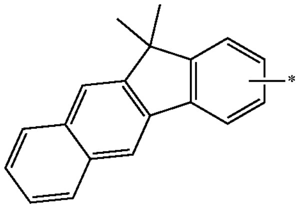

F4

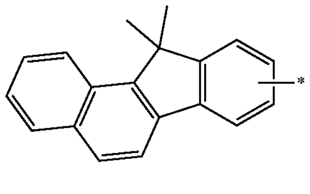

$R_3$ is selected from: hydrogen, deuterium, halogen, a cyano group, a $C_1$ to $C_{40}$ alkyl group, a $C_6$ to $C_{60}$ aryl group, a heteroaryl group having 5 to 60 nuclear atoms, the alkyl group, the aryl group, and the heteroaryl group of $R_3$ are each independently unsubstituted or substituted with one or more substituents of: deuterium, halogen, a cyano group, a nitro group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and when the substituents are plural in number, the substituents are the same as or different from each other, and the alkenyl group, the alkynyl group, the cycloalkyl group, the heterocycloalkyl group, the alkyl group, the aryl group, the alkyloxy group, the aryloxy group, the alkylsilyl group, the arylsilyl group, the alkylboron group, the arylboron group, the arylphosphine group, the arylphosphine oxide group and the arylamine group of $R_1$ and $R_2$ are each independently substituted or unsubstituted with one or more substituents of: deuterium, halogen, a cyano group, a nitro group, a $C_2$ to $C_{40}$ alkenyl group, a $C_2$ to $C_{40}$ alkynyl group, a $C_3$ to $C_{40}$ cycloalkyl group, a $C_1$ to $C_{40}$ alkyl group, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group, and when the substituents are plural in number, the substituents are the same as or different from each other, provided that when $R_1$ is aryl, $R_2$ is aryl, or both $R_1$ and $R_2$ are aryl, said aryl is not substituted with a heteroaryl group.

7. The electroluminescent device of claim 6, wherein the organic layer comprising the compound is an electron transport layer or an electron transport auxiliary layer.

8. The electroluminescent device of claim 6, wherein $R_1$ and $R_2$ are different from each other.

9. The electroluminescent device of claim 8, wherein any one of $R_1$ and $R_2$ is a biphenyl group or a terphenyl group, and the other is a phenyl group.

10. The electroluminescent device of claim 6 wherein $X_1$ is $CR_3$, $X_2$ is N, and $R_3$ is as defined in claim 8.

11. The electroluminescent device of claim 6, wherein the compound of Chemical Formula 1 or 2 is selected from the following Compounds 101 to 125 and 226 to 250:

101

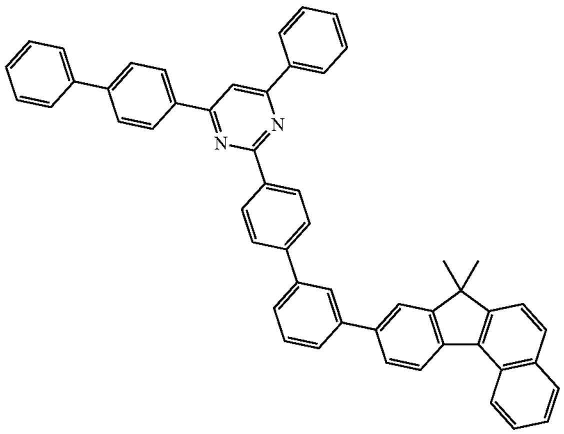

102
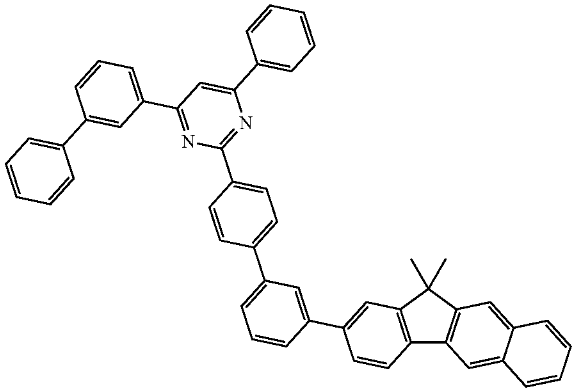
103
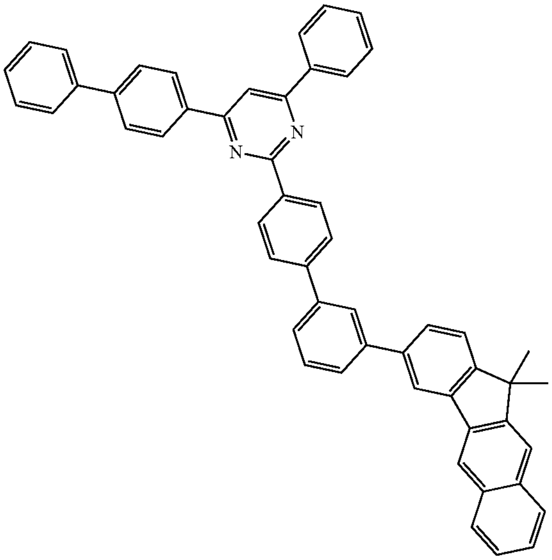
104
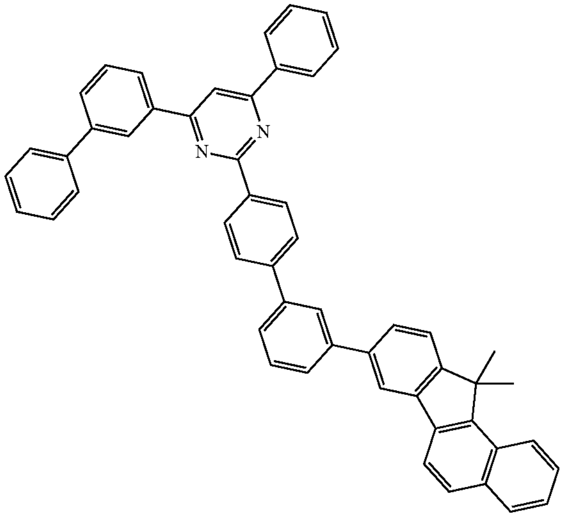
105
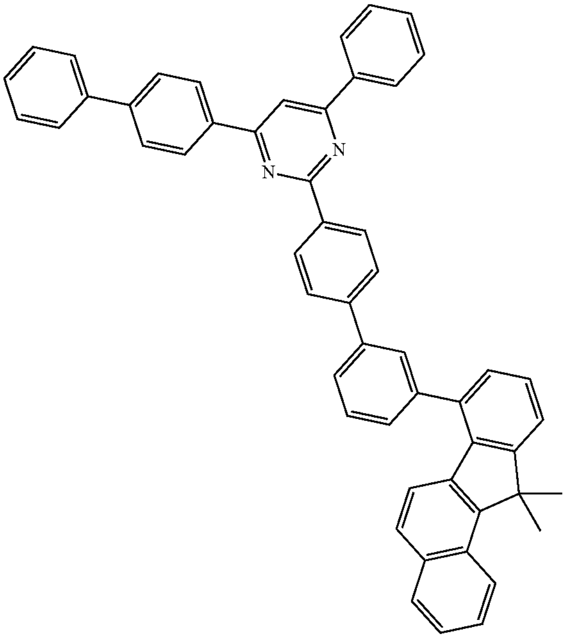
106
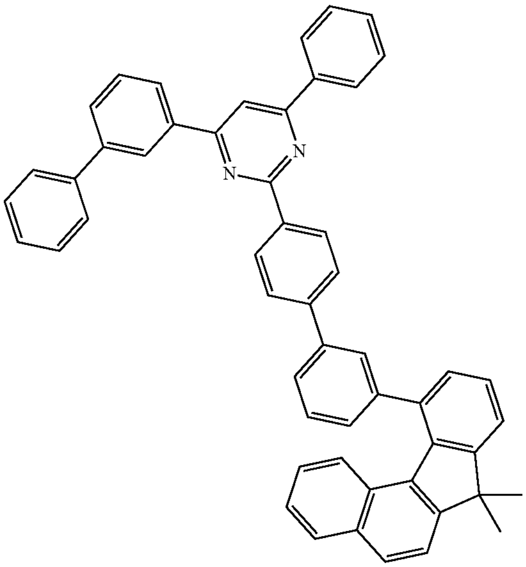

107
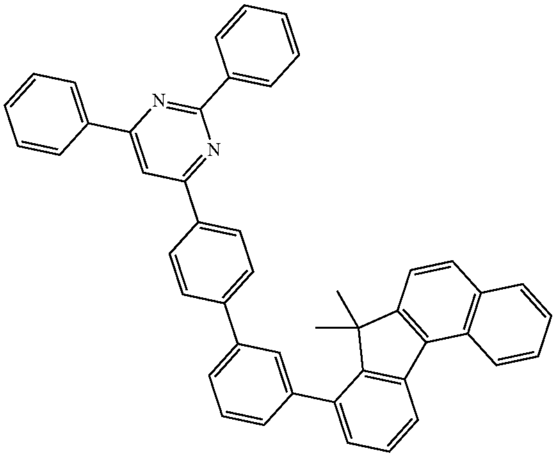
108
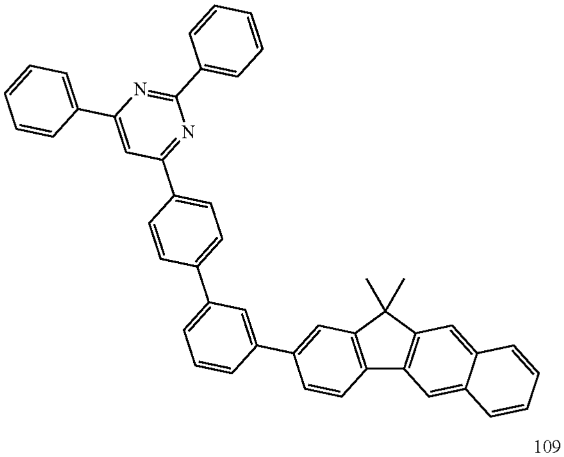
109
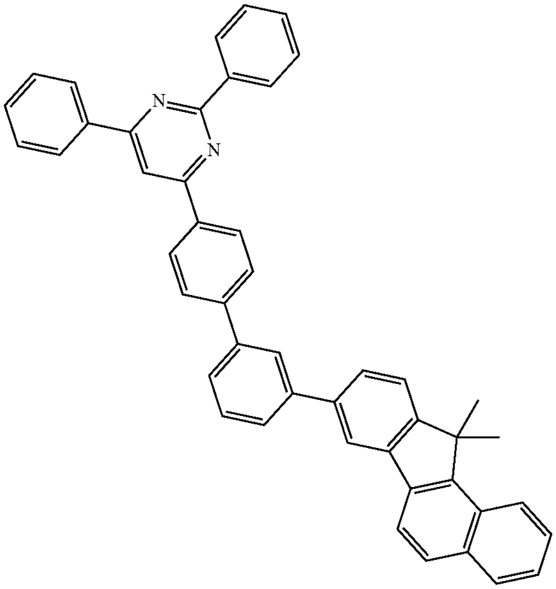
110
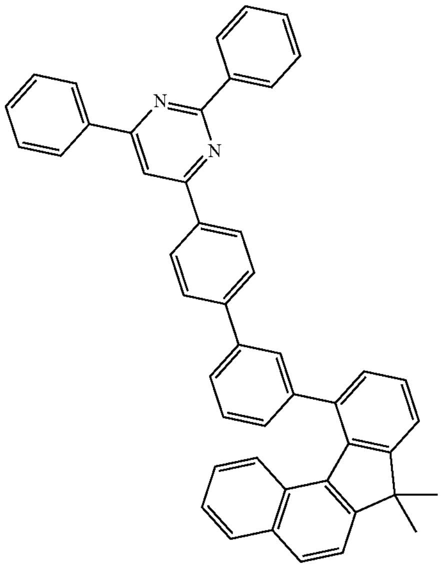
111
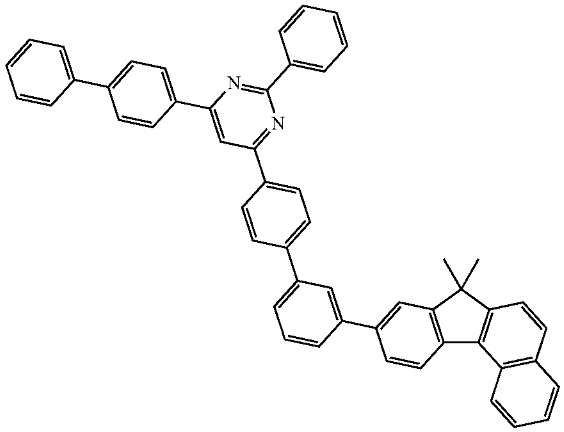
112
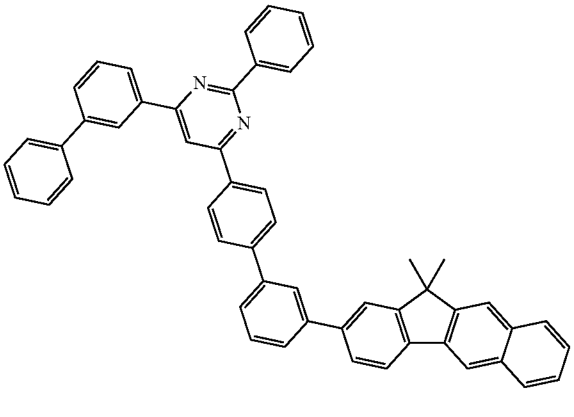

-continued
113
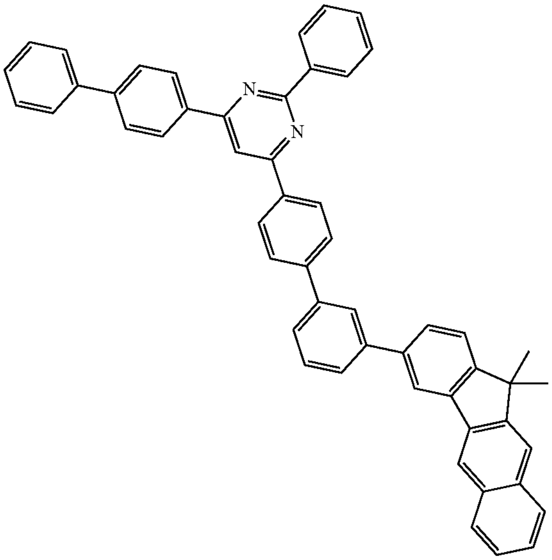
114
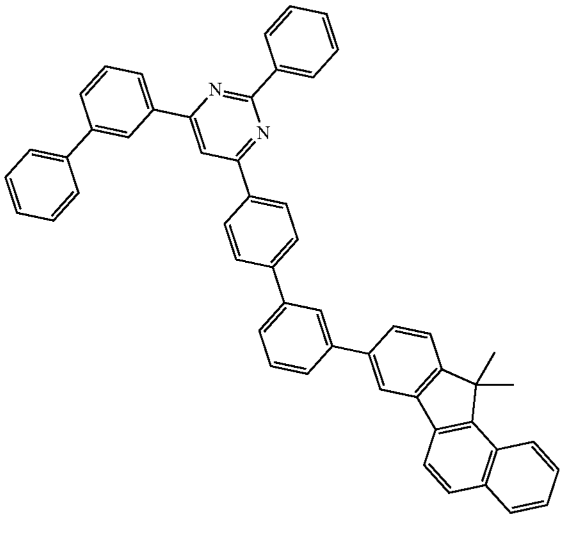
-continued
115
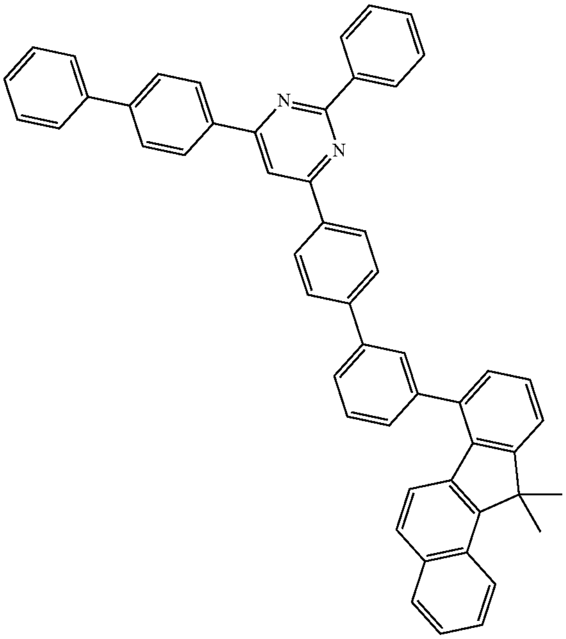
116
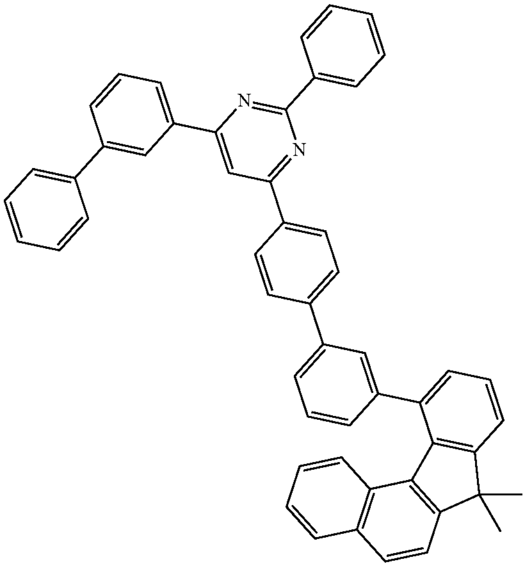
117
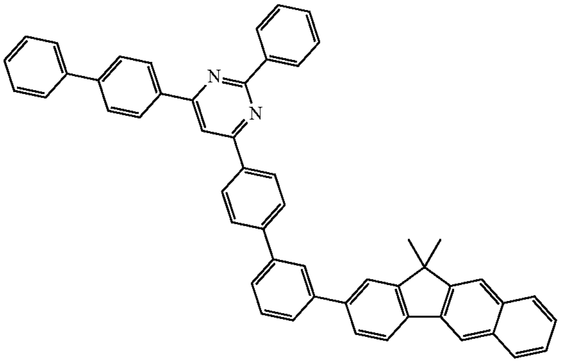

-continued
118
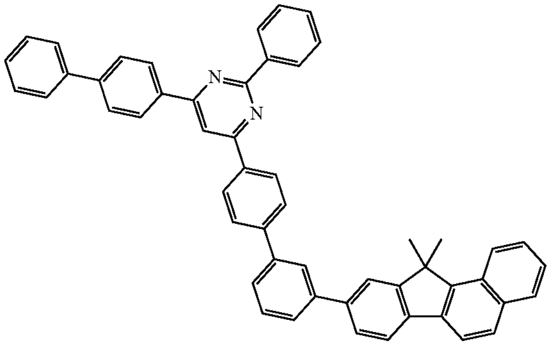
119
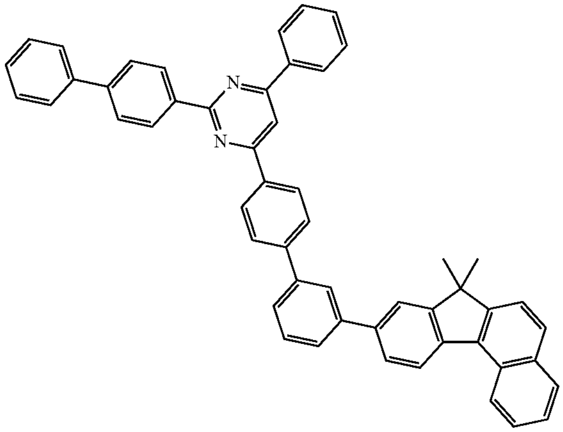
120
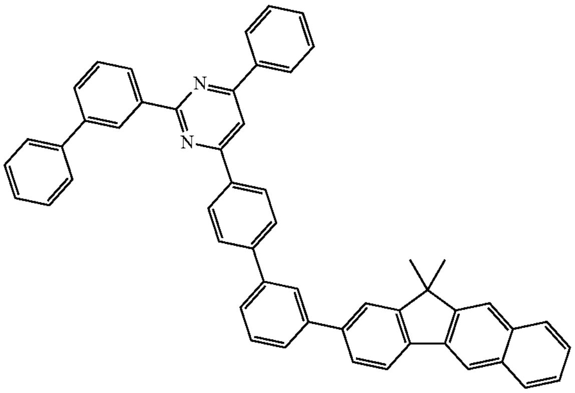
-continued
121
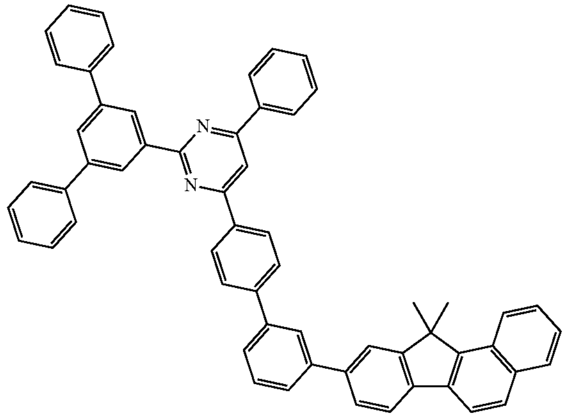
122
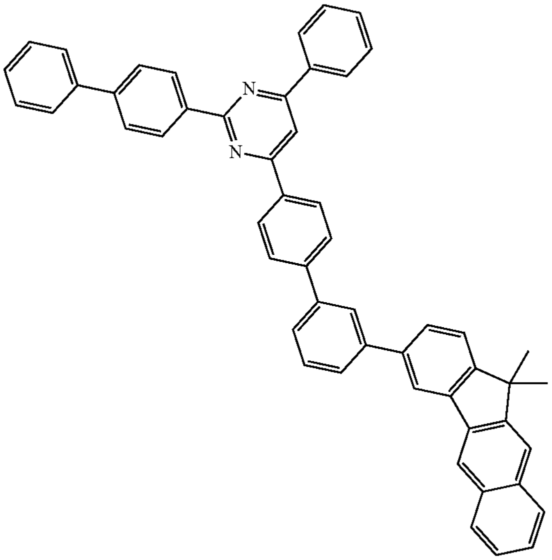
123
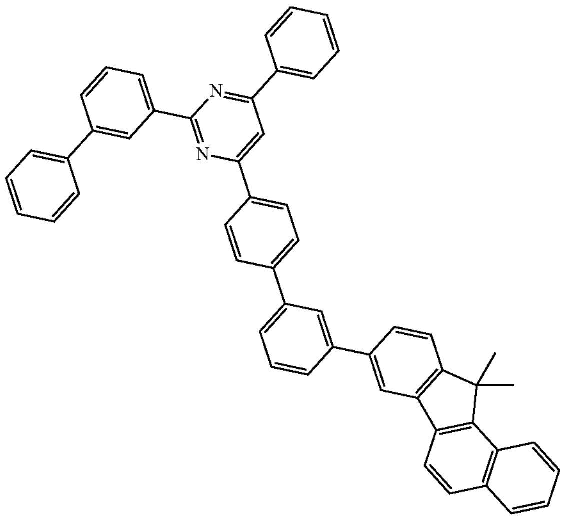

-continued
124
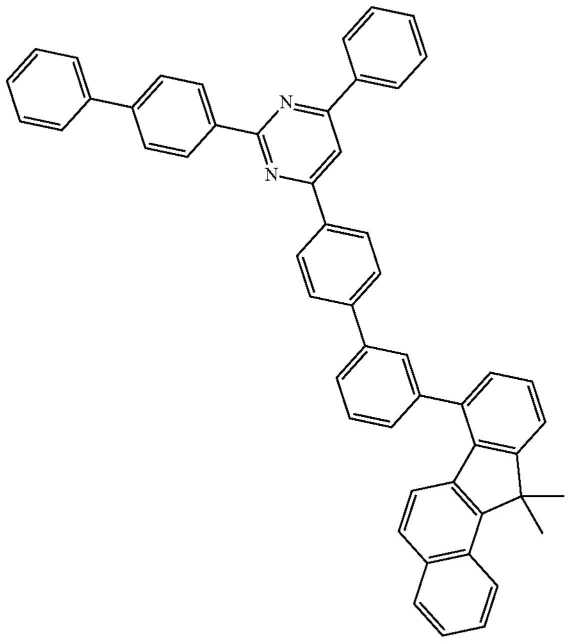
125
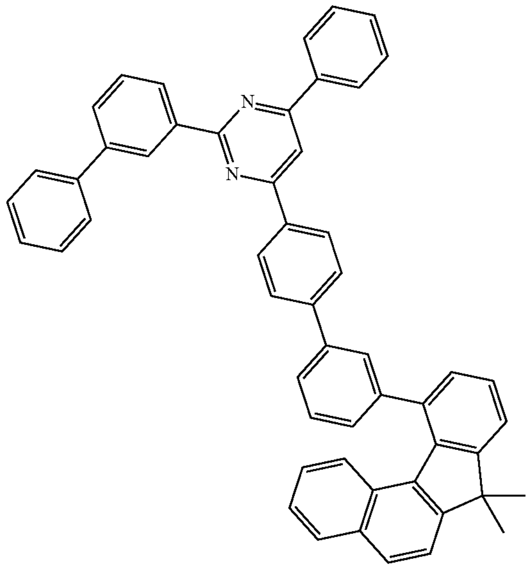
-continued
226
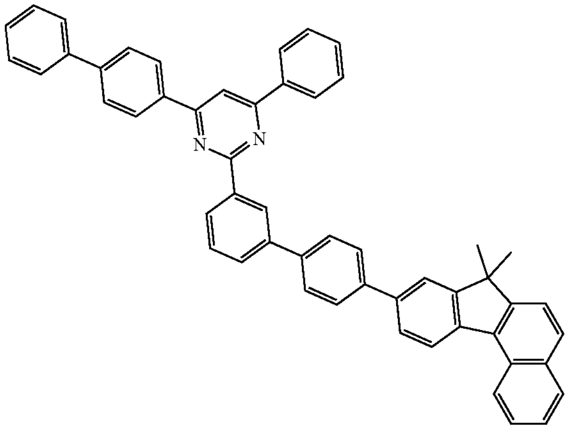
227
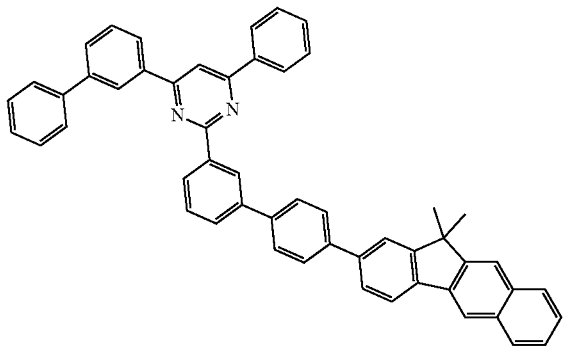
228
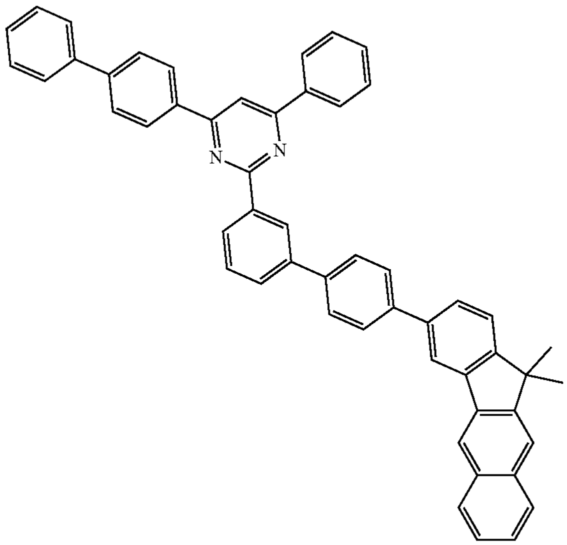

-continued
229
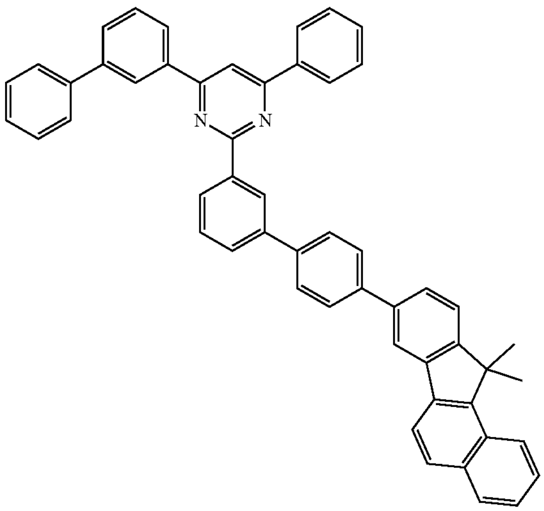
230
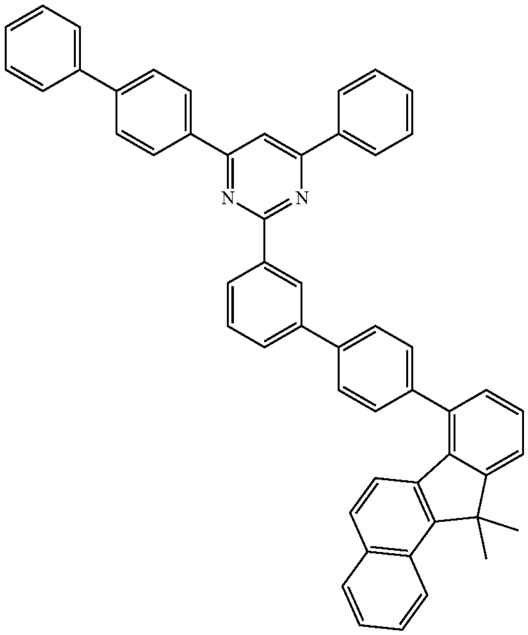
231
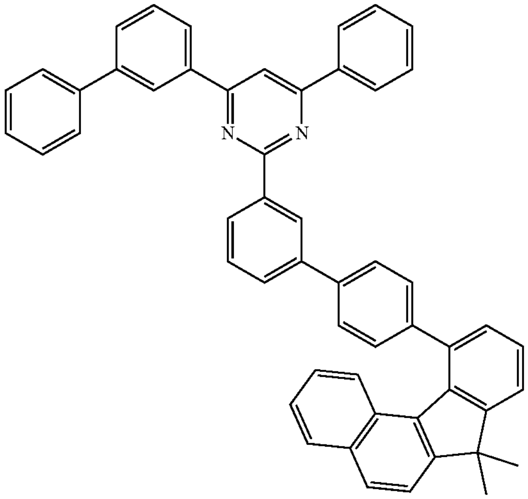
-continued
232
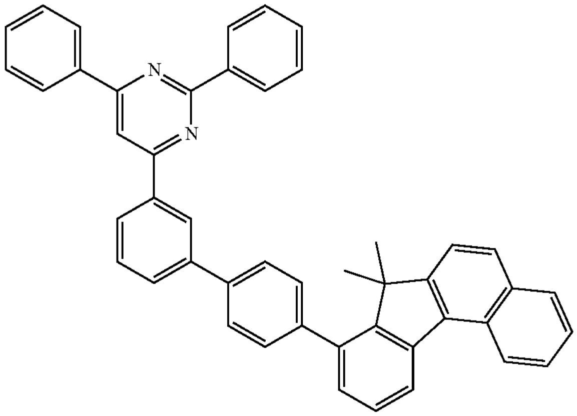
233
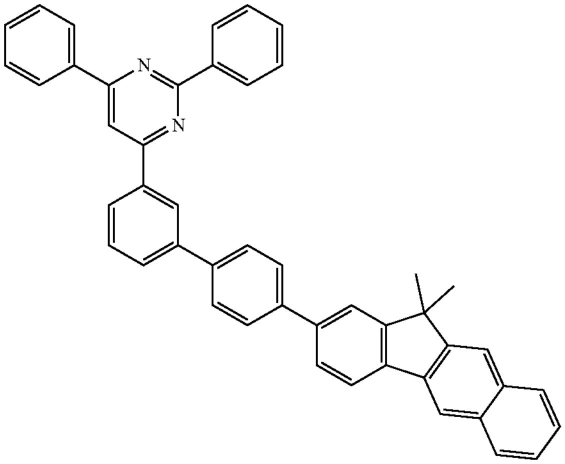
234
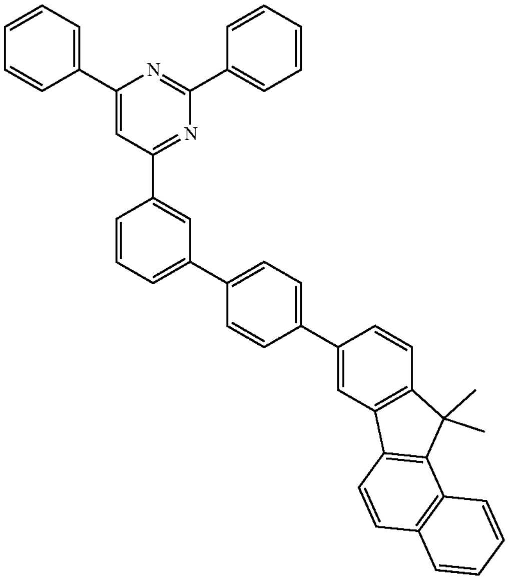

-continued
235
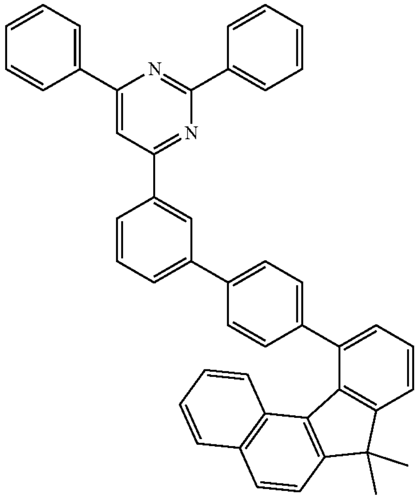
236
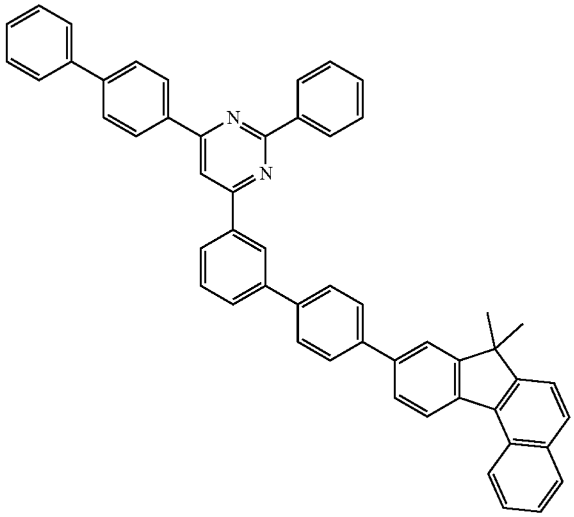
237
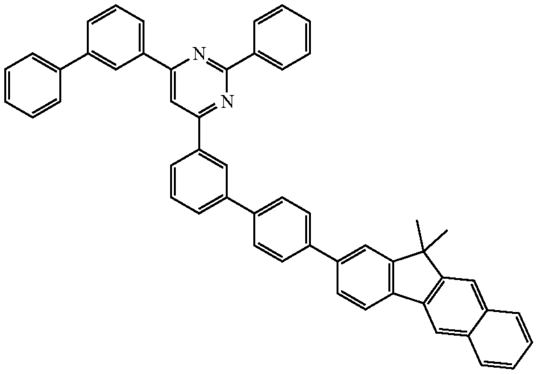
-continued
238
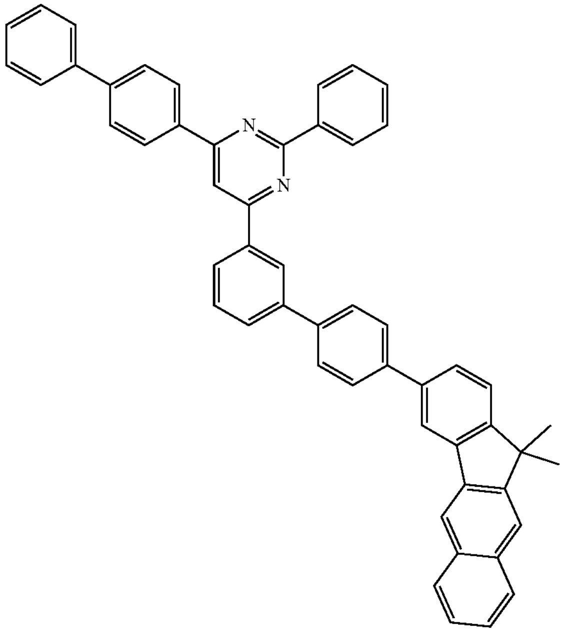
239
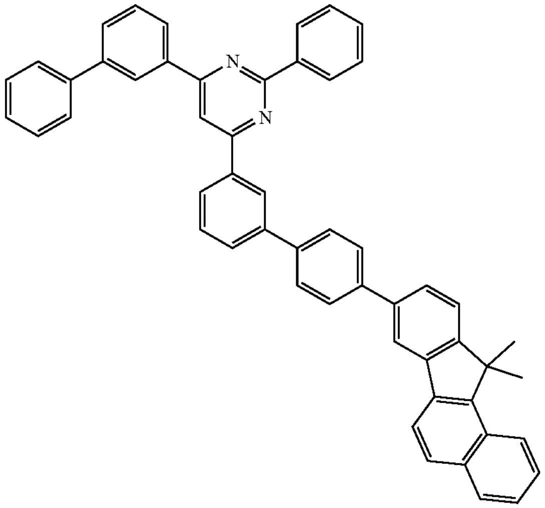

-continued
240
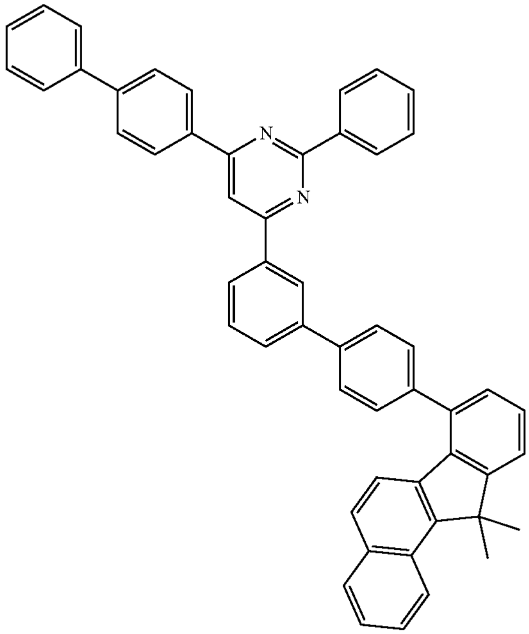
241
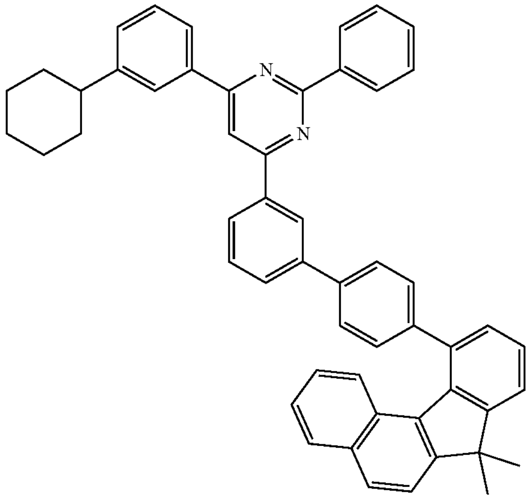
242
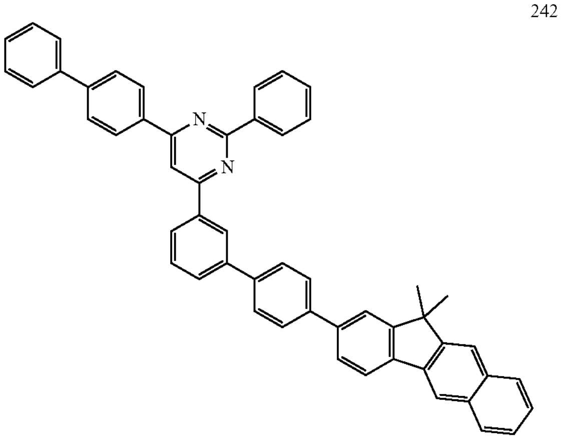
-continued
243
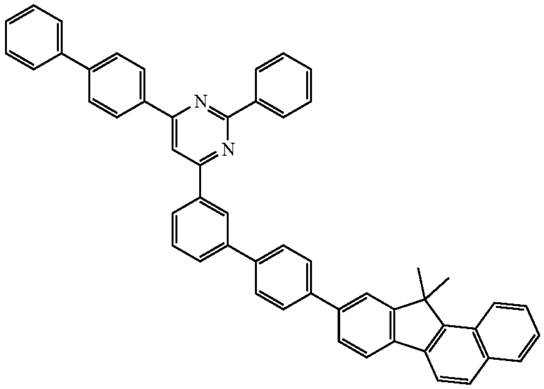
244
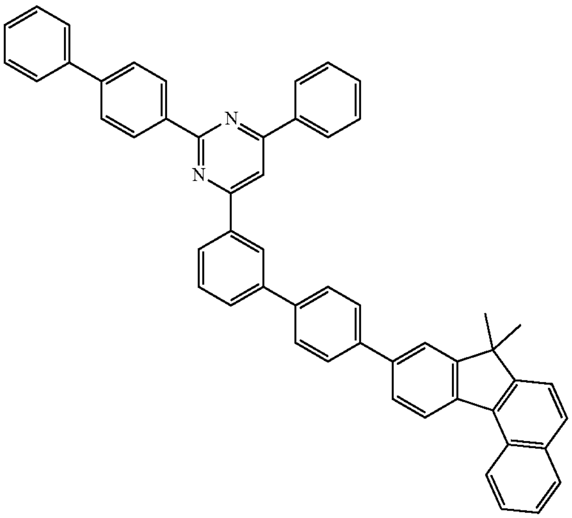
245
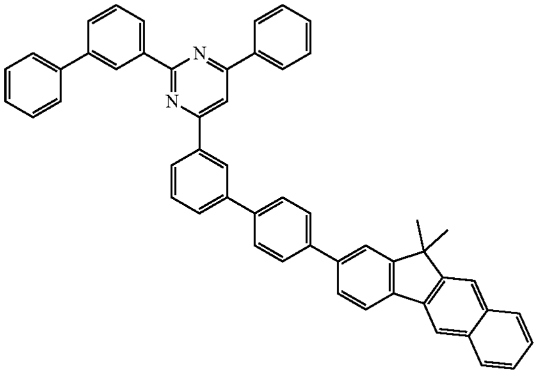

-continued
246
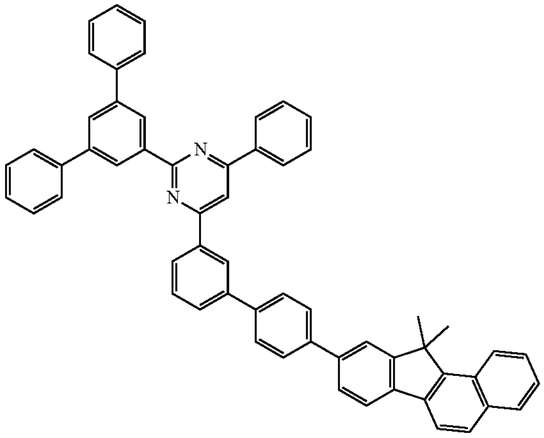
247
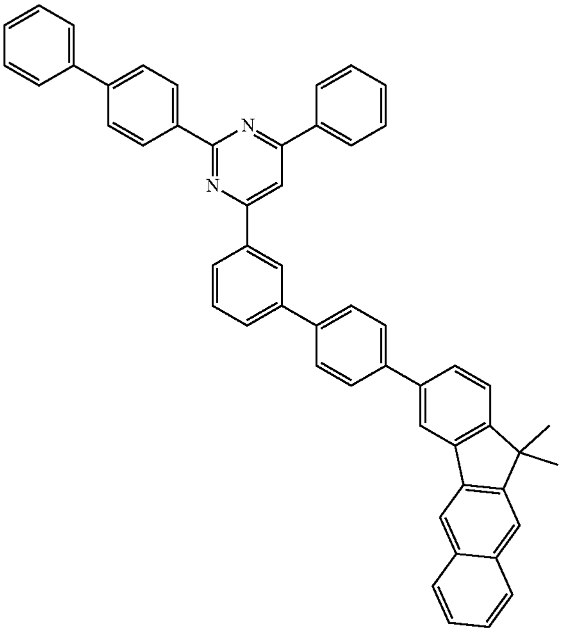
248
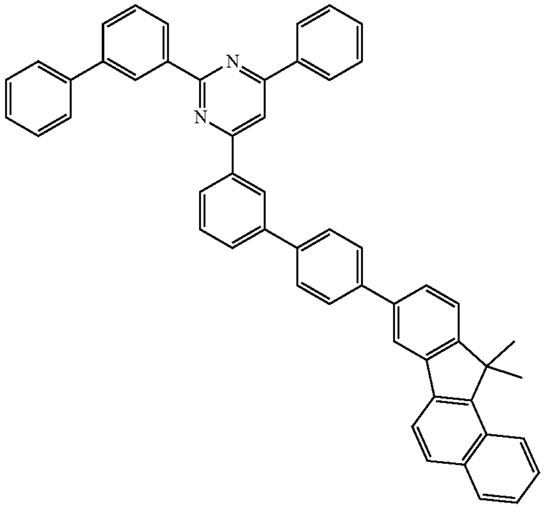
-continued
249
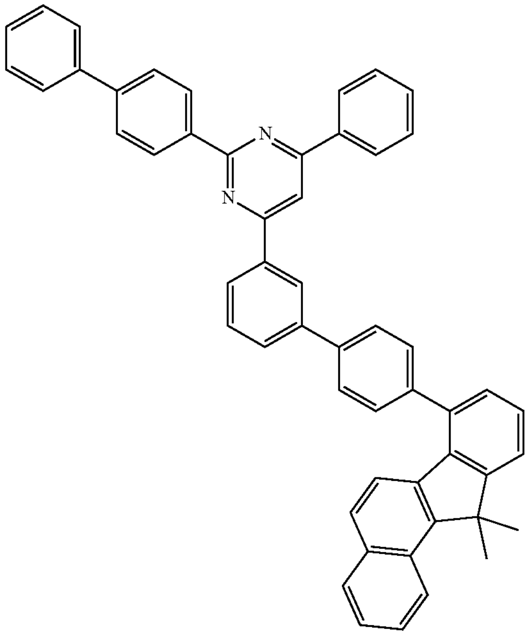
250
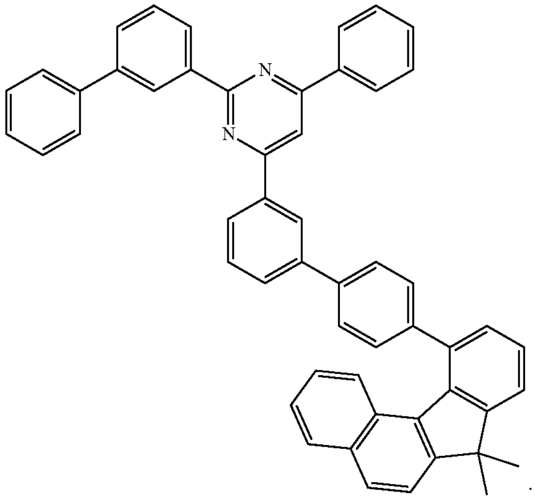
* * * * *